(12) United States Patent
Ferrie et al.

(10) Patent No.: US 11,639,489 B2
(45) Date of Patent: *May 2, 2023

(54) PACKED-BED BIOREACTOR SYSTEMS AND METHODS OF USING THE SAME

(71) Applicant: CORNING INCORPORATED, Corning, NY (US)

(72) Inventors: Ann MeeJin Ferrie, Salem, NH (US); Vasiliy Nikolaevich Goral, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,334

(22) Filed: Jul. 20, 2022

(65) Prior Publication Data

US 2022/0364031 A1 Nov. 17, 2022

Related U.S. Application Data

(63) Continuation of application No. 17/402,078, filed on Aug. 13, 2021, now Pat. No. 11,401,493, which is a
(Continued)

(51) Int. Cl.
*C12M 1/12* (2006.01)
*C12M 1/00* (2006.01)
(Continued)

(52) U.S. Cl.
CPC ............ *C12M 25/14* (2013.01); *C12M 23/02* (2013.01); *C12M 23/20* (2013.01); *C12M 23/44* (2013.01);
(Continued)

(58) Field of Classification Search
CPC ...... C12M 25/02; C12M 25/14; C12M 23/44; C12M 23/20; C12M 23/02; C12M 29/10; C12M 29/26
See application file for complete search history.

(56) References Cited

U.S. PATENT DOCUMENTS 3,853,712 A 12/1974 House et al.
4,201,845 A 5/1980 Feder et al.
(Continued)

FOREIGN PATENT DOCUMENTS

CN 200940147 Y 8/2007
CN 101605460 A 12/2009
(Continued)

OTHER PUBLICATIONS

Andersen et al., "Ionically Gelled Alginate Foams: Physical Properties Controlled by Operational and Macromolecular Parameter", American Chemical Society, Biomacromolecules, vol. 13, 2012, pp. 3703-3710.
(Continued)

*Primary Examiner* — Michael L Hobbs
(74) *Attorney, Agent, or Firm* — F. Brock Riggs

(57) ABSTRACT

A packed-bed bioreactor system is provided, the system including a cell culture vessel having a first end, a second end, and a reservoir between the first and second ends; and a cell culture matrix disposed in the reservoir. The cell culture matrix includes a structurally defined substrate with a plurality of interwoven fibers having surfaces for adhering cells thereto. The substrate is disposed within the reservoir in a wound configuration creating a plurality of layers of substrate in the wound configuration, and none of the plurality of layers of substrate are separated by a spacer material.

24 Claims, 34 Drawing Sheets

Related U.S. Application Data continuation of application No. 17/039,218, filed on Sep. 30, 2020, now Pat. No. 11,111,470, which is a continuation of application No. 16/781,723, filed on Feb. 4, 2020.

(60) Provisional application No. 62/910,696, filed on Oct. 4, 2019, provisional application No. 62/801,325, filed on Feb. 5, 2019.

(51) Int. Cl.
    *C12M 1/34* (2006.01)
    *C12M 3/00* (2006.01)
    *C12N 5/00* (2006.01)
    *C12N 5/071* (2010.01)

(52) U.S. Cl.
    CPC ............ *C12M 25/04* (2013.01); *C12M 29/10* (2013.01); *C12M 29/26* (2013.01); *C12M 41/26* (2013.01); *C12M 25/02* (2013.01); *C12N 5/0068* (2013.01); *C12N 5/0602* (2013.01); *C12N 2513/00* (2013.01); *C12N 2533/30* (2013.01); *C12N 2533/40* (2013.01); *C12N 2533/90* (2013.01); *C12N 2535/00* (2013.01)

(56) References Cited

U.S. PATENT DOCUMENTS

| | | |
|---|---|---|
| 4,755,281 A | 7/1988 | Penick |
| 4,833,083 A | 5/1989 | Saxena |
| 4,994,388 A | 2/1991 | Hillegas et al. |
| 5,012,503 A | 4/1991 | Nambu et al. |
| 5,079,168 A | 1/1992 | Amiot |
| 5,266,476 A | 11/1993 | Sussman et al. |
| 5,501,971 A | 3/1996 | Freedman et al. |
| 5,510,262 A | 4/1996 | Stephanopoulos et al. |
| 5,759,830 A | 6/1998 | Vacanti et al. |
| 5,840,777 A | 11/1998 | Eagles et al. |
| 5,998,184 A | 12/1999 | Shi |
| 6,054,142 A | 4/2000 | Li et al. |
| 6,130,080 A | 10/2000 | Fuller |
| 6,150,159 A | 11/2000 | Fry |
| 6,284,284 B1 | 9/2001 | Naughton |
| 6,334,968 B1 | 1/2002 | Shapiro et al. |
| 6,875,605 B1 | 4/2005 | Ma |
| 6,995,013 B2 | 2/2006 | Connelly et al. |
| 7,122,371 B1 | 10/2006 | Ma |
| 7,449,331 B2 | 11/2008 | Whitley |
| 7,524,513 B2 | 4/2009 | Hai-Quan et al. |
| 7,674,837 B2 | 3/2010 | Gaserod et al. |
| 7,700,747 B2 | 4/2010 | Sato |
| 7,968,050 B2 | 6/2011 | Vogt et al. |
| 8,137,959 B2 | 3/2012 | Castillo Fernandez |
| 8,198,080 B2 | 6/2012 | Bayon et al. |
| 8,507,263 B2 | 8/2013 | Asnaghi et al. |
| 8,597,939 B2 | 12/2013 | Castillo Fernandez |
| 8,653,319 B2 | 2/2014 | Amery et al. |
| 8,721,963 B2 | 5/2014 | Matthews et al. |
| 8,951,574 B2 | 2/2015 | Gehri et al. |
| 8,951,784 B2 | 2/2015 | Gould et al. |
| 9,089,117 B2 | 7/2015 | Grande et al. |
| 9,175,259 B2 | 11/2015 | Nankervis |
| 9,198,997 B2 | 12/2015 | Myntti et al. |
| 9,217,129 B2 | 12/2015 | Moretti et al. |
| 9,220,810 B2 | 12/2015 | Ma et al. |
| 9,228,579 B2 | 1/2016 | Stobbe |
| 9,273,278 B2 | 3/2016 | Lee et al. |
| 9,617,506 B2 | 4/2017 | Jones et al. |
| 9,657,266 B2 | 5/2017 | Kasuto |
| 9,677,038 B2 | 6/2017 | Stobbe |
| 9,694,037 B2 | 7/2017 | Nataraj et al. |
| 9,766,228 B2 | 9/2017 | Puschmann et al. |
| 10,077,420 B2 | 9/2018 | Blahut |
| 10,494,421 B2 | 12/2019 | Castillo |
| 11,111,470 B2 | 9/2021 | Ferrie et al. |
| 2002/0155594 A1 | 10/2002 | Hsieh et al. |
| 2004/0211747 A1 | 10/2004 | Whitley |
| 2005/0014774 A1 | 1/2005 | Storer et al. |
| 2008/0206735 A1 | 8/2008 | Asgari |
| 2009/0076530 A1 | 3/2009 | Fukutomi et al. |
| 2009/0196901 A1 | 8/2009 | Guilak et al. |
| 2009/0239298 A1 | 9/2009 | Gerecht et al. |
| 2009/0263601 A1 | 10/2009 | Renn |
| 2010/0196963 A1 | 8/2010 | Naughton et al. |
| 2010/0203638 A1 | 8/2010 | Adachi et al. |
| 2010/0216229 A1 | 8/2010 | Kenney et al. |
| 2011/0040226 A1 | 2/2011 | Amery et al. |
| 2011/0212493 A1 | 9/2011 | Hirschel et al. |
| 2011/0236256 A1 | 9/2011 | Matthews et al. |
| 2011/0250679 A1 | 10/2011 | Chang |
| 2011/0263021 A1 | 10/2011 | Stobbe |
| 2011/0275056 A1 | 11/2011 | Antwiler |
| 2012/0129257 A1 | 5/2012 | Yu et al. |
| 2012/0253071 A1 | 10/2012 | Rau et al. |
| 2013/0116571 A1 | 5/2013 | Cox et al. |
| 2013/0171710 A1 | 7/2013 | Prebble |
| 2014/0030805 A1 | 1/2014 | Kasuto et al. |
| 2014/0193901 A1 | 7/2014 | Lee et al. |
| 2014/0227769 A1 | 8/2014 | Strobbe |
| 2014/0243995 A1 | 8/2014 | Kolewe et al. |
| 2015/0299634 A1 | 10/2015 | Drugmand et al. |
| 2015/0322399 A1 | 11/2015 | Purushothaman et al. |
| 2016/0145567 A1 | 5/2016 | Henry et al. |
| 2016/0281045 A1 | 9/2016 | McCall et al. |
| 2016/0304832 A1 | 10/2016 | Hariri et al. |
| 2017/0166859 A1 | 6/2017 | Wang et al. |
| 2017/0321178 A1 | 11/2017 | Ling et al. |
| 2018/0016547 A1 | 1/2018 | Hagihara et al. |
| 2018/0044622 A1 | 2/2018 | Poon et al. |
| 2018/0187139 A1 | 7/2018 | Patel |
| 2018/0187141 A1 | 7/2018 | Cox et al. |
| 2018/0195048 A1 | 7/2018 | Rao |
| 2018/0273891 A1 | 9/2018 | Tanabe et al. |
| 2018/0282678 A1 | 10/2018 | Castillo et al. |
| 2019/0062683 A1 | 2/2019 | Nankervis et al. |
| 2019/0134271 A1 | 5/2019 | Seo et al. |
| 2019/0275519 A1 | 9/2019 | Castillo et al. |
| 2019/0382709 A1 | 12/2019 | Vang et al. |
| 2020/0157493 A1* | 5/2020 | Ginn .................. D03D 15/50 |
| 2020/0248121 A1 | 8/2020 | Ferrie et al. |
| 2020/0248122 A1 | 8/2020 | Ferrie et al. |
| 2020/0248123 A1* | 8/2020 | Ferrie .................. C12M 41/26 |
| 2020/0248124 A1 | 8/2020 | Ferrie et al. |
| 2020/0255783 A1 | 8/2020 | Ferrie et al. |
| 2021/0024868 A1 | 1/2021 | Ferrie et al. |
| 2021/0115378 A1 | 4/2021 | Fahmy |
| 2021/0130761 A1 | 5/2021 | Ferrie et al. |

FOREIGN PATENT DOCUMENTS

| | | |
|---|---|---|
| CN | 102250390 A | 11/2011 |
| CN | 103113627 A | 5/2013 |
| CN | 105492595 A | 4/2016 |
| CN | 108315258 A | 7/2018 |
| DE | 3536349 A1 | 4/1987 |
| EP | 0044624 A1 | 1/1982 |
| EP | 0300666 A1 | 1/1989 |
| EP | 0967273 A1 | 12/1999 |
| EP | 1245670 A2 | 10/2002 |
| EP | 2154241 A2 | 2/2010 |
| EP | 2553860 A1 | 2/2013 |
| EP | 2566950 A1 | 3/2013 |
| EP | 3452575 A1 | 3/2019 |
| JP | 05-179381 A | 7/1993 |
| JP | 2001-120255 A | 5/2001 |
| JP | 2013-063283 A | 4/2013 |
| WO | 88/00235 A1 | 1/1988 |
| WO | 98/50522 A1 | 11/1998 |
| WO | 00/05257 A1 | 2/2000 |
| WO | 01/03750 A1 | 1/2001 |
| WO | 2005/014774 A1 | 2/2005 |
| WO | 2005/023323 A1 | 3/2005 |

(56) References Cited

FOREIGN PATENT DOCUMENTS

| | | |
|---|---|---|
| WO | 2006/088029 A1 | 8/2006 |
| WO | 2011/123805 A1 | 10/2011 |
| WO | 2011/139957 A1 | 11/2011 |
| WO | 2012/140519 A2 | 10/2012 |
| WO | 2014/093444 A1 | 6/2014 |
| WO | 2014/133805 A1 | 9/2014 |
| WO | 2014/209856 A1 | 12/2014 |
| WO | 2014/209865 A1 | 12/2014 |
| WO | 2016/200888 A1 | 12/2016 |
| WO | 2017/193075 A1 | 11/2017 |
| WO | 2017/204563 A1 | 11/2017 |
| WO | 2018/187808 A1 | 10/2018 |
| WO | 2019/090211 A1 | 5/2019 |
| WO | 2019/104069 A1 | 5/2019 |
| WO | 2019/175442 A1 | 9/2019 |
| WO | 2019/206902 A1 | 10/2019 |
| WO | 2021/108072 A1 | 6/2021 |

OTHER PUBLICATIONS

Arboleya et al., "Competitive Adsorption of Proteins With Methylcellulose and Hydroxypropyl Methylcellulose", Food Hydrocolloids, vol. 19, No. 3, May 2005, pp. 485-491.

Baker et al., "Deconstructing The Third Dimension—How 3D Culture Microenvironments Alter Cellular Cues", Journal of Cell Science, vol. 125, 2012, pp. 3015-3024.

Barbetta et al., "Porous Alginate Hydrogels: Synthetic Methods for Tailoring the Porous Texture", Biomacromolecules, vol. 10, 2009, pp. 2328-2337.

Baylon et al; "Past, Present and Future of Surgical Meshes: A Review"; Membranes 2017, 47, 17; 23 pages doi:10.3390/membranes7030047.

Bokhari et al., "Emulsion-templated Porous Polymers as Scaffolds for Three Dimensional Cell Culture: Effect of Synthesis Parameters on Scaffold Formation and Homogeneity", Journal of Materials Chemistry, vol. 17, Jul. 2007, pp. 4088-4094.

Champagne et al. "Effect of Immobilization in Alginate on the Stability of Freeze-Dried Bffidobacterium longum", Bioscience Microflora, 1996, vol. 15(1), pp. 9-15.

Da Violante et al; "Evaluation of the Cytotoxicity Effect of Dimethyl Sulfoxide (DMSO) on Caco2/TC7 Colon Tumor Cell Cultures"; Biol. Pharm. Bull. 25 (12) pp. 1600-1603 (2002.

Dickinson, Eric, "Hydrocolloids at Interfaces and The Influence on The Properties of Dispersed Systems", Food Hydrocolloids, vol. 17, No. 1, Jan. 2003, pp. 25-39.

Emmerling et al; "Rational Plasmid Design and Bioprocess Optimization to Enhance Recombinant Adeno-Associated Virus (AAV) Productivity in Mammalian Cells"; Biotechnol. J. 2016, 11, (2)290297.

Fang, Y. et al., "Rehydration of Dried Alginate Gel Beads: Effect of the Presence of Gelatin and Gum Arabic." Carbohydrate Polymers, vol. 86, pp. 1145-1150, Jun. 13, 2011.

Galvao et al; "Unexpected Low-Dose Toxicity of The Universal Solvent DMSO"; The FASEB Journal, Research Communication, vol. 28, (2014); pp. 1-14.

Gong et al; "The Physical and Chemical Properties of Alginate and its Application in Tissue Engineering Research and Clinical Application"; China Tissue Engineering Research and Clinical Rehabilitation, vol. 11, No. 18 pp. 3613-3615 (Abstract), 2007.

Gunter et al. "Swelling and morphology of calcium pectinate gel beads obtained from Silene vulgaris callus modified pectins", Carbohydrate Polymers, 2014, vol. 103, pp. 550-557.

Huang et al., "Research Trypsin-Induced Proteome Alteration During Cell Subculture in Mammalian Cells", Huang et al. Journal of Biomedical Science, vol. 17, No. 36, 2010, pp. 1-10.

Hwang et al., "Fabrication of Three-Dimensional Porous Cell-Laden Hydrogel for Tissue Engineering", IOP Publishing, Biofabrication, vol. 2,035003, 2010, pp. 1-12.

Kuo et al., "Ionically Crosslinked Alginate Hydrogels as Scalolds for Tissue Engineering: Part 1. Structure, Gelation Rate and Mechanical Properties", Biomaterials, vol. 22, 2001, pp. 511-521.

Lawrence, Benjamin J., "Mass Transfer in Porous Tissue Engineering Scaffolds", Oklahoma State University, 2008, 193 pages.

Lee et al., "Optimization of Calcium Pectinate Gel Beads for Sustained-Release of Catechin Using Response Surface Methodology", International Journal of Biological Macromolecules, vol. 42, No. 4, Jan. 18, 2008, pp. 340-347.

Lee et al; "Toxicity Evaluation of Ethanol Treatment During in Vitro Maturation of Procine Oocytes and Subsequent Embroyonic Development Following Parthenogenetic Activation and in Vitro Fertilization"; International Journal of Molecular Medicine; 34; pp. 1372-138 (2014.

Leo et al. "Effects of Sterilization Treatments on Some Properties of Alginate Solutions and Gels", Biotechnol. Prog., 1990, vol. 6, pp. 51-53.

Liu et al., "Effect of 3D Scaffold and Dynamic Culture Condition on The Global Gene Expression Profile of Mouse Embryonic Stem Cells", Biomaterials; vol. 27, No. 36, Dec. 2006, pp. 5978-5989.

Lonza, "Protocol for Performing a Trypan Blue Viability Test Technical Reference Guide", Available Online at <https://web.archive.org/web/20180921014905/http://www.lonzabio.jp/catalog/pdf/ri/T204.pdf>, BioResearch, Sep. 21, 2018, 2 pages.

Mseka et al., "ADF/Cofilin Family Proteins Control Formation of Oriented Actin-filament Bundles in The Cell Body to Trigger Fibroblast Polarization", Journal of Cell Science, vol. 120, 2007, pp. 4332-4344.

Munarin et al. "Sterilization treatments on polysaccharides: Effects and side effects on pectin", Food Hydrocolloids, 2013, vol. 31, pp. 74-84.

Nasatto et al., "Methylcellulose, a Cellulose Derivative with Original Physical Properties and Extended Applications", Polymers, vol. 7, 2015, pp. 777-803.

Neethu et al., "Pectin/carboxymethyl cellulose/microfibrillated cellulose composite scaffolds for tissue engineering", Carbohydrate Polymers, vol. 98, No. 1, Jul. 7, 2013, pp. 877-885.

Oberdoerster et al; "Differential Effect of Ethanol on PC12 Cell Death"; The Journal of Pharmacology and Experimental Therapeutics; vol. 287, No. 1; pp. 359-365 (1998.

Rainger et al; "A Novel System for Investigating the Ability of Smooth Muscle Cells and Fibroblasts to Regulate Adhesion of Flowing Leukocytes to Endothelial Cells"; Journal of Immimmunological Methods; 255 (2001) 73-82.

Santagapita, P. et al., "Formulation and Drying of Alginate Beads for Controlled Release and Stabilization of Invertase." Biomacromolecules vol. 12, pp. 3147-3155, Aug. 18, 2011.

Srivastava et al., "Development of a Novel Polygalacturonic Acid-Gelatin Blend Scaffold Fabrication and Biocompatibility Studies for Tissue-Engineering Applications", International Journal of Polymeric Materials, vol. 61, No. 9, 2012, pp. 679-698.

Stanley et al., "Texture-Structure Relationships in Foamed Dairy Emulsions", Food Research International, vol. 29, No. 1, 1996, pp. 1-13.

Tapani et al; "Toxicity of Ethanol in Low Concentrations"; Acta Radiologica; 37:6; pp. 923-926; (1996).

Tsai et al., "Expansion of Human Mesenchymal Stem Cells in Fibrous Bed Bioreactor",Biochemical Engineering Journal, 2015, pp. 1-7.

Vreeker, R. et al., "Drying and Rehydration of Calcium Alginate Gels." Food Biophysics, vol. 3, pp. 361-369, Jun. 26, 2008.

Zmora et al., "Tailoring The Pore Architecture in 3-d Alginate Scaffolds by Controlling The Freezing Regime During Fabrication", Biomaterials, vol. 23, 2002, pp. 4087-4094.

\* cited by examiner

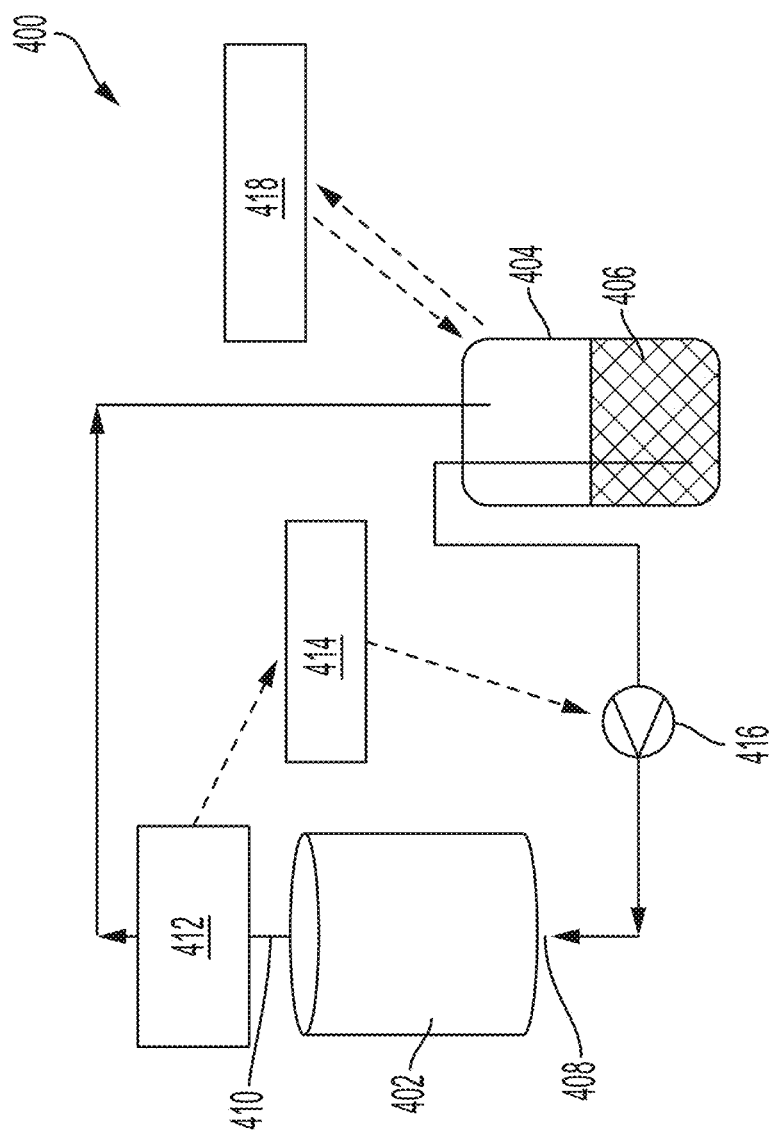

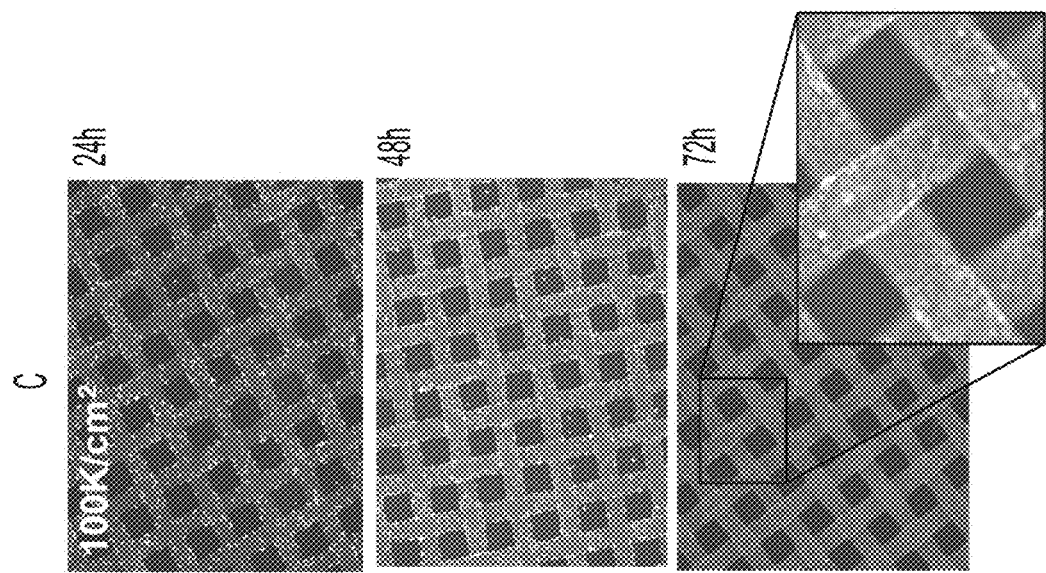
FIGURE 12C
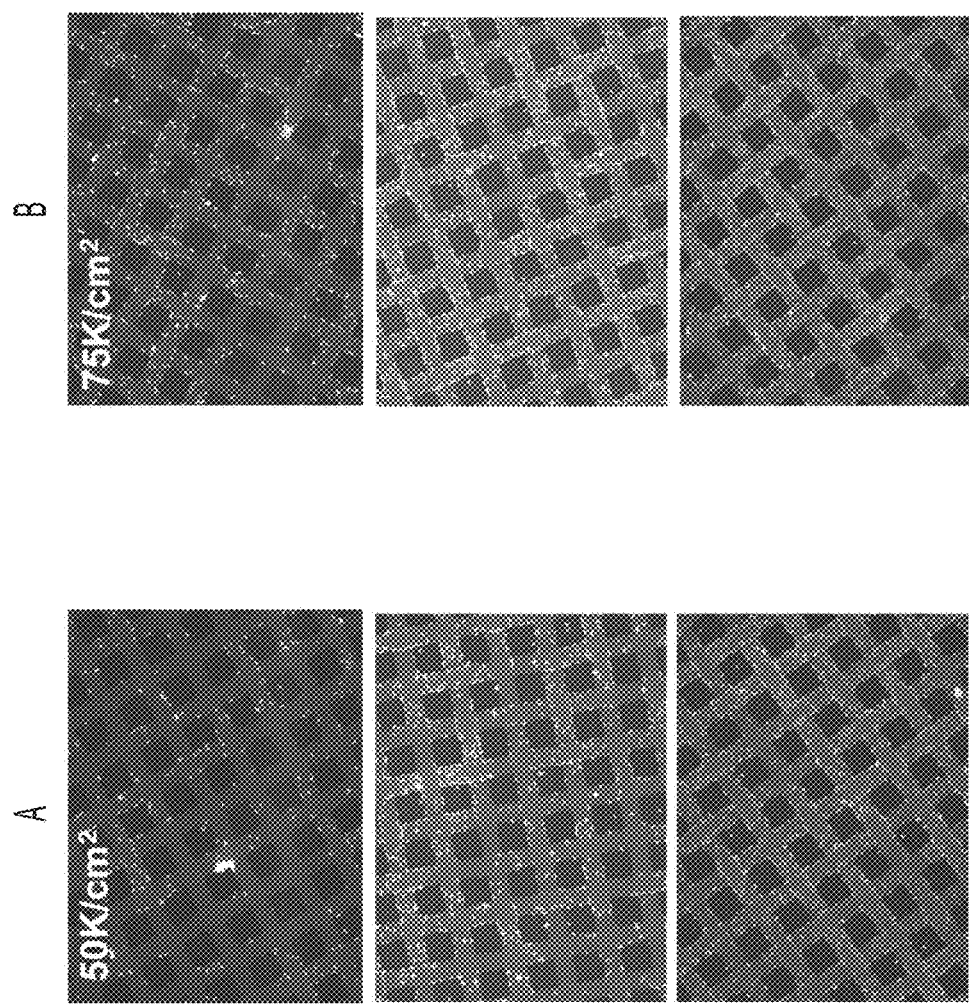
FIGURE 12B
FIGURE 12A

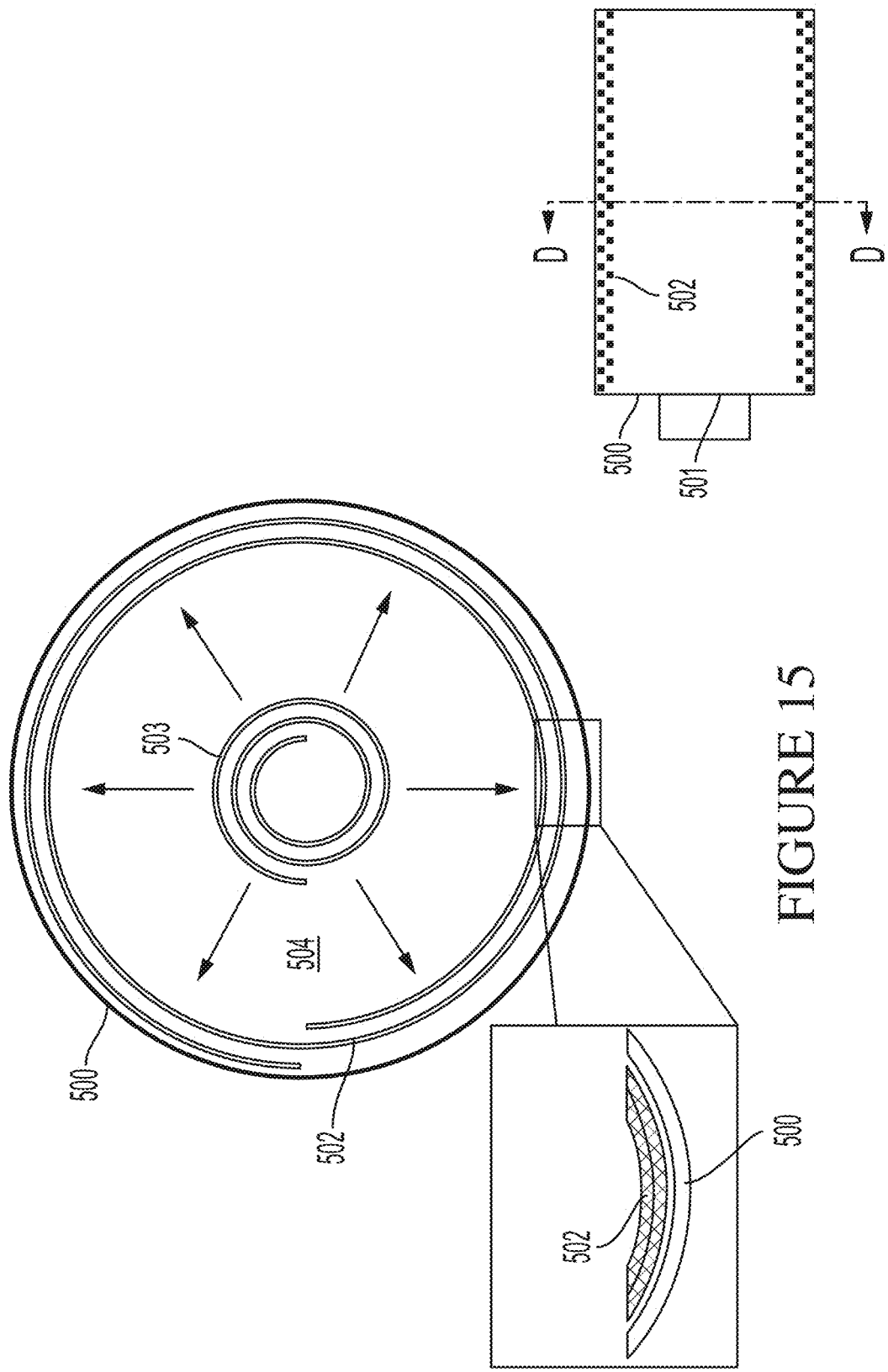

PACKED-BED BIOREACTOR SYSTEMS AND METHODS OF USING THE SAME

CROSS-REFERENCE TO RELATED APPLICATIONS

This application is a continuation of U.S. patent application Ser. No. 17/402,078 filed on Aug. 13, 2021 and granted as U.S. Pat. No. 11,401,493 on Aug. 2, 2022, which is a continuation of and claims the benefit of priority to U.S. patent application Ser. No. 17/039,218 filed on Sep. 30, 2020 and granted as U.S. Pat. No. 11,111,470 on Sep. 7, 2021, which is a continuation of and claims the benefit of priority to U.S. patent application Ser. No. 16/781,723 filed on Feb. 4, 2020, which claims the benefit of priority under 35 U.S.C § 120 of U.S. Provisional Application Ser. No. 62/910,696 filed on Oct. 4, 2019 and U.S. Provisional Application Ser. No. 62/801,325 filed on Feb. 5, 2019, the contents of which are relied upon and incorporated herein by reference in their entireties.

FIELD OF THE DISCLOSURE

This disclosure general relates to substrates for culturing cells, as well as systems and methods for culturing cells. In particular, the present disclosure relates to cell culturing substrates, bioreactor systems incorporating such substrates, and methods of culturing cells using such substrates.

BACKGROUND

In the bioprocessing industry, large-scale cultivation of cells is performed for purposes of the production of hormones, enzymes, antibodies, vaccines, and cell therapies. Cell and gene therapy markets are growing rapidly, with promising treatments moving into clinical trials and quickly toward commercialization. However, one cell therapy dose can require billions of cells or trillions of viruses. As such, being able to provide a large quantity of cell products in a short amount of time is critical for clinical success.

A significant portion of the cells used in bioprocessing are anchorage dependent, meaning the cells need a surface to adhere to for growth and functioning. Traditionally, the culturing of adherent cells is performed on two-dimensional (2D) cell-adherent surfaces incorporated in one of a number of vessel formats, such as T-flasks, petri dishes, cell factories, cell stack vessels, roller bottles, and HYPERStack® vessels. These approaches can have significant drawbacks, including the difficulty in achieving cellular density high enough to make it feasible for large scale production of therapies or cells.

Alternative methods have been suggested to increase volumetric density of cultured cells. These include microcarrier cultures performed in stir tanks. In this approach, cells that are attached to the surface of microcarriers are subject to constant shear stress, resulting in a significant impact on proliferation and culture performance. Another example of a high-density cell culture system is a hollow fiber bioreactor, in which cells may form large three-dimensional aggregates as they proliferate in the interspatial fiber space. However, the cells growth and performance are significantly inhibited by the lack nutrients. To mitigate this problem, these bioreactors are made small and are not suitable for large scale manufacturing Another example of a high-density culture system for anchorage dependent cells is a packed-bed bioreactor system. In this this type of bioreactor, a cell substrate is used to provide a surface for the attachment of adherent cells. Medium is perfused along the surface or through the semiporous substrate to provide nutrients and oxygen needed for the cell growth. For example, packed bed bioreactor systems that contain a packed bed of support or matrix systems to entrap the cells have been previously disclosed U.S. Pat. Nos. 4,833,083; 5,501,971; and 5,510,262. Packed bed matrices usually are made of porous particles as substrates or non-woven microfibers of polymer. Such bioreactors function as recirculation flow-through bioreactors. One of the significant issues with such bioreactors is the non-uniformity of cell distribution inside the packed bed. For example, the packed bed functions as depth filter with cells predominantly trapped at the inlet regions, resulting in a gradient of cell distribution during the inoculation step. In addition, due to random fiber packaging, flow resistance and cell trapping efficiency of cross sections of the packed bed are not uniform. For example, medium flows fast though the regions with low cell packing density and flows slowly through the regions where resistance is higher due to higher number of entrapped cells. This creates a channeling effect where nutrients and oxygen are delivered more efficiently to regions with lower volumetric cells densities and regions with higher cell densities are being maintained in suboptimal culture conditions.

Another significant drawback of packed bed systems disclosed in a prior art is the inability to efficiently harvest intact viable cells at the end of culture process. Harvesting of cells is important if the end product is cells, or if the bioreactor is being used as part of a "seed train," where a cell population is grown in one vessel and then transferred to another vessel for further population growth. U.S. Pat. No. 9,273,278 discloses a bioreactor design to improve the efficiency of cell recovery from the packed bed during cells harvesting step. It is based on loosening the packed bed matrix and agitation or stirring of packed bed particles to allow porous matrices to collide and thus detach the cells. However, this approach is laborious and may cause significant cells damage, thus reducing overall cell viability.

An example of a packed-bed bioreactor currently on the market is the iCellis® by produced by Pall Corporation. The iCellis uses small strips of cell substrate material consisting of randomly oriented fibers in a non-woven arrangement. These strips are packed into a vessel to create a packed bed. However, as with similar solutions on the market, there are drawbacks to this type of packed-bed substrate. Specifically, non-uniform packing of the substrate strips creates visible channels within the packed bed, leading to preferential and non-uniform media flow and nutrient distribution through the packed bed. Studies of the iCellis® have noted a "systemic inhomogeneous distribution of cells, with their number increasing from top to bottom of fixed bed," as well as a "nutrient gradient . . . leading to restricted cell growth and production," all of which lead to the "unequal distribution of cells [that] may impair transfection efficiency." (Rational plasmid design and bioprocess optimization to enhance recombinant adeno-associated virus (AAV) productivity in mammalian cells. *Biotechnol. J.* 2016, 11, 290-297). Studies have noted that agitation of the packed bed may improve dispersion, but would have other drawbacks (i.e., "necessary agitation for better dispersion during inoculation and transfection would induce increased shear stress, in turn leading to reduced cell viability." Id.). Another study noted of the iCellis® that the uneven distribution of cells makes monitoring of the cell population using biomass sensors difficult (" . . . if the cells are unevenly distributed, the biomass signal from the cells on the top carriers may not show the general view of the entire bioreactor." Process Development of Adenoviral Vector Production in Fixed Bed Bioreactor: From Bench to Commercial Scale. *Human Gene Therapy, Vol.* 26, No. 8, 2015).

In addition, because of the random arrangement of fibers in the substrate strips and the variation in packing of strips between one packed bed and another of the iCellis®, it can be difficult for customers to predict cell culture performance, since the substrate varies between cultures. Furthermore, the packed substrate of the iCellis® makes efficiently harvesting cells very difficult or impossible, as it is believed that cells are entrapped by the packed bed.

Roller bottles have several advantages such as ease of handling, and ability to monitor cells on the attachment surface. However, from a production standpoint, the main disadvantage is the low surface area to volume ratio while the roller bottle configuration occupies a large area of manufacturing floor space. Various approaches have been used to increase the surface area available for adherent cells in a roller bottle format. Some solutions have been implemented in commercially available products, but there remains room for improvement to increase roller bottle productivity even further. Traditionally, a roller bottle is produced as a single structure by a blow-molding process. Such manufacturing simplicity enables economic viability of roller bottles in bioprocessing industry. Some roller bottle modifications to increase the available surface area for cell culturing can be achieved without changing manufacturing process, however only marginal increase of modified roller bottle surface area is obtained. Other modifications of the roller bottle design add significant complexity to manufacturing processes making it economically unviable in the bioprocessing industry. It is desirable therefore to provide roller bottle with increased surface area and bioprocessing productivity, while using the same blow-molding process for its manufacturing.

While manufacturing of viral vectors for early-phase clinical trials is possible with existing platforms, there is a need for a platform that can produce high-quality product in greater numbers in order to reach late-stage commercial manufacturing scale.

There is a need for cell culture matrices, systems, and methods that enable culturing of cells in a high-density format, with uniform cell distribution, and easily attainable and increased harvesting yields.

SUMMARY

According to an embodiment of this disclosure, a packed-bed bioreactor system for culturing cells is provided. The system includes: a cell culture vessel with at least one interior reservoir, an inlet fluidly connected to the reservoir, and an outlet fluidly connected to the reservoir; and a packed-bed cell culture matrix disposed in the reservoir. The cell culture matrix includes a plurality structurally defined substrate layers for adhering cells thereto, and each of the substrate layers has a physical structure and a porosity that are regular and uniform. Some aspects of embodiments include the packed-bed cell culture matrix having a uniform porosity and/or the packed-bed cell culture matrix being configured for uniform fluid flow therethrough. As an additional aspect, the plurality of the structurally defined substrates includes a stack of substrate disks disposed in the reservoir. In a further aspect, the structurally defined substrate includes a plurality of openings defining the porosity, the plurality of openings being arrayed in a regular or uniform pattern in each substrate disk.

According to an embodiment of this disclosure, a cell culture matrix is provided. The cell culture matrix includes a substrate having a first side, a second side opposite the first side, a thickness separating the first side and the second side, and a plurality of openings formed in the substrate and passing through the thickness of the substrate. The plurality of openings is configured to allow flow of at least one of cell culture media, cells, or cell products through the thickness of the substrate. The substrate can be at least one of a molded polymer lattice sheet, a 3D-printed lattice sheet, and a woven mesh sheet. The substrate has a regular, ordered structure and provides a surface for cell adhesion, growth, and eventual cell release.

According to an embodiment of this disclosure, a bioreactor system for cell culture is provided, the system includes a cell culture vessel having at least one reservoir; and a cell culture matrix disposed in the at least one reservoir, the cell culture matrix including a woven substrate having a plurality of interwoven fibers with surfaces configured for adhering cells thereto.

According to one or more embodiments, a cell culture system is provided, the system includes a bioreactor vessel; and a cell culture matrix disposed in the bioreactor vessel and configured to culture cells. The cell culture matrix includes a substrate comprising a first side, a second side opposite the first side, a thickness separating the first and second sides, and a plurality of openings formed in the substrate and passing through the thickness of the substrate, and the plurality of openings is configured to allow flow of at least one of cell culture media, cells, or cell products through the thickness of the substrate.

According to one or more embodiments, a bioreactor system for culturing cells is provided. The system includes: a cell culture vessel having a first end, a second end, and at least one reservoir between the first and second ends; and a cell culture matrix disposed in the at least one reservoir. The cell culture matrix has a plurality of woven substrates each including a plurality of interwoven fibers with surfaces configured for adhering cells thereto. The bioreactor system is configured to flow material through the at least one reservoir in a flow direction from the first end to the second end, and the substrates of the plurality of woven substrates are stacked such that each woven substrate is substantially parallel to each of the other woven substrates and is substantially perpendicular to the flow direction.

According to one or more embodiments, a bioreactor system for culturing cells is provided. The system includes: a cell culture vessel having a first end, a second end, and at least one reservoir between the first and second ends; and a cell culture matrix disposed in the at least one reservoir, the cell culture matrix including a plurality of woven substrates each having a plurality of interwoven fibers with surfaces configured for adhering cells thereto. The bioreactor system is configured to flow material through the at least one reservoir in a flow direction from the first end to the second end, and the substrates of the plurality of woven substrates are stacked such that each woven substrate is substantially parallel to each of the other woven substrates and is substantially parallel to the flow direction.

According to one or more embodiments, a bioreactor system for culturing cells is provided. The system includes cell culture vessel having a first end, a second end, and at least one reservoir between the first and second ends; and a cell culture matrix disposed in the at least one reservoir. The cell culture matrix includes a woven substrate comprising a plurality of interwoven fibers with surfaces configured for adhering cells thereto, and the woven substrate is disposed within the at least one reservoir in a wound configuration to provide a cylindrical cell culture matrix with a surface of the woven substrate being parallel to a longitudinal axis of the cylindrical cell culture matrix.

According to another embodiment, a method of culturing cells in a bioreactor is provided. The method includes providing a bioreactor vessel having a cell culture chamber within the bioreactor vessel, and a cell culture matrix disposed in the cell culture chamber. The cell culture matrix is provided for culturing cells thereon. The cell culture matrix includes a substrate having a first side, a second side opposite the first side, a thickness separating the first side and the second side, and a plurality of openings formed in the substrate and passing through the thickness of the substrate. The method further includes seeding cells on the cell culture matrix; culturing the cells on the cell culture matrix; and harvesting a product of the culturing of the cells. The plurality of openings in the substrate allow flow of at least one of cell culture media, cells, or cell products through the thickness of the substrate.

BRIEF DESCRIPTION OF THE DRAWINGS

FIG. 10A is a schematic representation of a cell culture system, according to one or more embodiments.

FIG. 12A is a micrograph of stained HEK293T cells on a cell culture substrate, where the cells were seeded at a first cell seeding density, according to one or more embodiments.

FIG. 12B is a micrograph of stained HEK293T cells on a cell culture substrate, where the cells were seeded at a second cell seeding density, according to one or more embodiments.

FIG. 12C is a micrograph of stained HEK293T cells on a cell culture substrate, where the cells were seeded at a third cell seeding density, according to one or more embodiments.

FIG. 15 is a cross-section schematic of a cell-culture system with an expanding cell culture substrate, according to one or more embodiments.

FIG. 16 is a cross-section view of a roller-bottle style cell culture vessel with a multi-layer cell culture substrate, according to one or more embodiments.

DETAILED DESCRIPTION

Figure 1A:
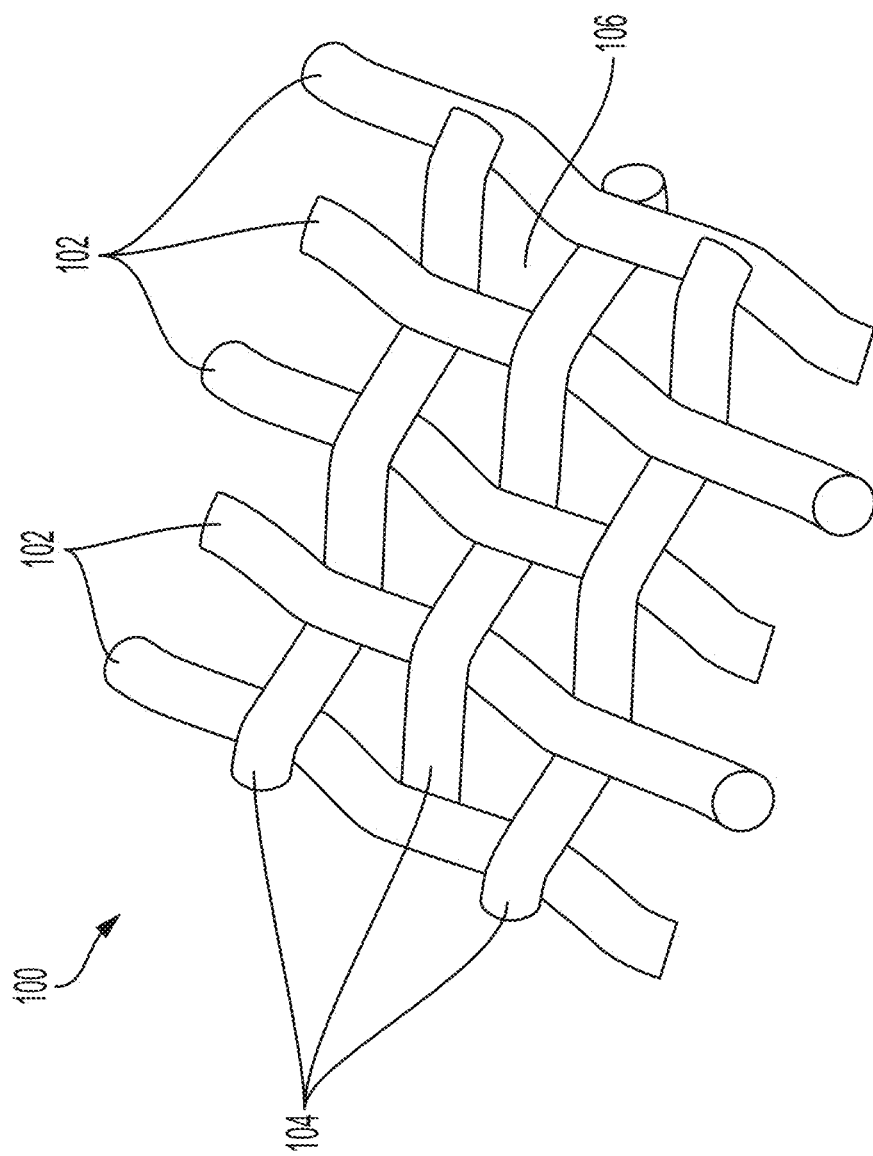
FIG. 1A shows a perspective view of a three-dimensional model of a cell culture substrate, according to one or more embodiments of this disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

Embodiments of this disclosure a cell culture substrate, as well as cell culture or bioreactor systems incorporating such a substrate, and methods of culturing cells using such a substrate and bioreactor systems.

In conventional large-scale cell culture bioreactors, different types of packed bed bioreactors have been used. Usually these packed beds contain porous matrices to retain adherent or suspension cells, and to support growth and proliferation. Packed-bed matrices provide high surface area to volume ratios, so cell density can be higher than in the other systems. However, the packed bed often functions as a depth filter, where cells are physically trapped or entangled in fibers of the matrix. Thus, because of linear flow of the cell inoculum through the packed bed, cells are subject to heterogeneous distribution inside the packed-bed, leading to variations in cell density through the depth or width of the packed bed. For example, cell density may be higher at the inlet region of a bioreactor and significantly lower nearer to the outlet of the bioreactor. This non-uniform distribution of the cells inside of the packed-bed significantly hinders scalability and predictability of such bioreactors in bioprocess manufacturing, and can even lead to reduced efficiency in terms of growth of cells or viral vector production per unit surface area or volume of the packed bed.

Another problem encountered in packed bed bioreactors disclosed in prior art is the channeling effect. Due to random nature of packed nonwoven fibers, the local fiber density at any given cross section of the packed bed is not uniform. Medium flows quickly in the regions with low fiber density (high bed permeability) and much slower in the regions of high fiber density (lower bed permeability). The resulting non-uniform media perfusion across the packed bed creates the channeling effect, which manifests itself as significant nutrient and metabolite gradients that negatively impact overall cell culture and bioreactor performance. Cells located in the regions of low media perfusion will starve and very often die from the lack of nutrients or metabolite poisoning. Cell harvesting is yet another problem encountered when bioreactors packed with non-woven fibrous scaffolds are used. Due to packed-bed functions as depth filter, cells that are released at the end of cell culture process are entrapped inside the packed bed, and cell recovery is very low. This significantly limits utilization of such bioreactors in bioprocesses where live cells are the products. Thus, the non-uniformity leads to areas with different exposure to flow and shear, effectively reducing the usable cell culture area, causing non-uniform culture, and interfering with transfection efficiency and cell release.

To address these and other problems of existing cell culture solutions, embodiments of the present disclosure provide cell growth substrates, matrices of such substrates, and/or packed-bed systems using such substrates that enable efficient and high-yield cell culturing for anchorage-dependent cells and production of cell products (e.g., proteins, antibodies, viral particles). Embodiments include a porous cell-culture matrix made from an ordered and regular array of porous substrate material that enables uniform cell seeding and media/nutrient perfusion, as well as efficient cell harvesting. Embodiments also enable scalable cell-culture solutions with substrates and bioreactors capable of seeding and growing cells and/or harvesting cell products from a process development scale to a full production size scale, without sacrificing the uniform performance of the embodiments. For example, in some embodiments, a bioreactor can be easily scaled from process development scale to product scale with comparable viral genome per unit surface area of substrate (VG/cm$^2$) across the production scale. The harvestability and scalability of the embodiments herein enable their use in efficient seed trains for growing cell populations at multiple scales on the same cell substrate. In addition, the embodiments herein provide a cell culture matrix having a high surface area that, in combination with the other features described, enables a high yield cell culture solution. In some embodiments, for example, the cell culture substrate and/or bioreactors discussed herein can produce $10^{16}$ to $10^{18}$ viral genomes (VG) per batch.

In one embodiment, a matrix is provided with a structurally defined surface area for adherent cells to attach and proliferate that has good mechanical strength and forms a highly uniform multiplicity of interconnected fluidic networks when assembled in a packed bed or other bioreactor. In particular embodiments, a mechanically stable, non-degradable woven mesh can be used as the substrate to support adherent cell production. The cell culture matrix disclosed herein supports attachment and proliferation of anchorage dependent cells in a high volumetric density format. Uniform cell seeding of such a matrix is achievable, as well as efficient harvesting of cells or other products of the bioreactor. In addition, the embodiments of this disclosure support cell culturing to provide uniform cell distribution during the inoculation step and achieve a confluent monolayer or multilayer of adherent cells on the disclosed matrix, and can avoid formation of large and/or uncontrollable 3D cellular aggregates with limited nutrient diffusion and increased metabolite concentrations. Thus, the matrix eliminates diffusional limitations during operation of the bioreactor. In addition, the matrix enables easy and efficient cell harvest from the bioreactor. The structurally defined matrix of one or more embodiments enables complete cell recovery and consistent cell harvesting from the packed bed of the bioreactor.

According to some embodiments, a method of cell culturing is also provided using bioreactors with the matrix for bioprocessing production of therapeutic proteins, antibodies, viral vaccines, or viral vectors.

In contrast to existing cell culture substrates used in cell culture bioreactors (i.e., non-woven substrates of randomly ordered fibers), embodiments of this disclosure include a cell culture substrate having a defined and ordered structure. The defined and order structure allows for consistent and predictable cell culture results. In addition, the substrate has an open porous structure that prevents cell entrapment and enables uniform flow through the packed bed. This construction enables improved cell seeding, nutrient delivery, cell growth, and cell harvesting. According to one or more particular embodiments, the matrix is formed with a substrate material having a thin, sheet-like construction having first and second sides separated by a relatively small thickness, such that the thickness of the sheet is small relative to the width and/or length of the first and second sides of the substrate. In addition, a plurality of holes or openings are formed through the thickness of the substrate. The substrate material between the openings is of a size and geometry that allows cells to adhere to the surface of the substrate material as if it were approximately a two-dimensional (2D) surface, while also allowing adequate fluid flow around the substrate material and through the openings. In some embodiments, the substrate is a polymer-based material, and can be formed as a molded polymer sheet; a polymer sheet with openings punched through the thickness; a number of filaments that are fused into a mesh-like layer; a 3D-printed substrate; or a plurality of filaments that are woven into a mesh layer. The physical structure of the matrix has a high surface-to-volume ratio for culturing anchorage dependent cells. According to various embodiments, the matrix can be arranged or packed in a bioreactor in certain ways discussed here for uniform cell seeding and growth, uniform media perfusion, and efficient cell harvest.

Embodiments of this disclosure can achieve viral vector platforms of a practical size that can produce viral genomes on the scale of greater than about $10^{14}$ viral genomes per batch, greater than about $10^{15}$ viral genomes per batch, greater than about $10^{16}$ viral genomes per batch, greater than about $10^{17}$ viral genomes per batch, or up to or greater than about g $10^{16}$ viral genomes per batch. In some embodiments, productions is about $10^{15}$ to about $10^{18}$ or more viral genomes per batch. For example, in some embodiments, the viral genome yield can be about $10^{15}$ to about $10^{16}$ viral genomes or batch, or about $10^{16}$ to about $10^{19}$ viral genomes per batch, or about $10^{16}$-$10^{18}$ viral genomes per batch, or about $10^{17}$ to about $10^{19}$ viral genomes per batch, or about $10^{18}$ to about $10^{19}$ viral genomes per batch, or about $10^{18}$ or more viral genomes per batch.

In addition, the embodiments disclosed herein enable not only cell attachment and growth to a cell culture substrate, but also the viable harvest of cultured cells. The inability to harvest viable cells is a significant drawback in current platforms, and it leads to difficulty in building and sustaining a sufficient number of cells for production capacity. According to an aspect of embodiments of this disclosure, it is possible to harvest viable cells from the cell culture substrate, including between 80% to 100% viable, or about 85% to about 99% viable, or about 90% to about 99% viable. For example, of the cells that are harvested, at least 80% are viable, at least 85% are viable, at least 90% are viable, at least 91% are viable, at least 92% are viable, at least 93% are viable, at least 94% are viable, at least 95% are viable, at least 96% are viable, at least 97% are viable, at least 98% are viable, or at least 99% are viable. Cells may be released from the cell culture substrate using, for example, trypsin, TrypLE, or Accutase.

Figure 1B:
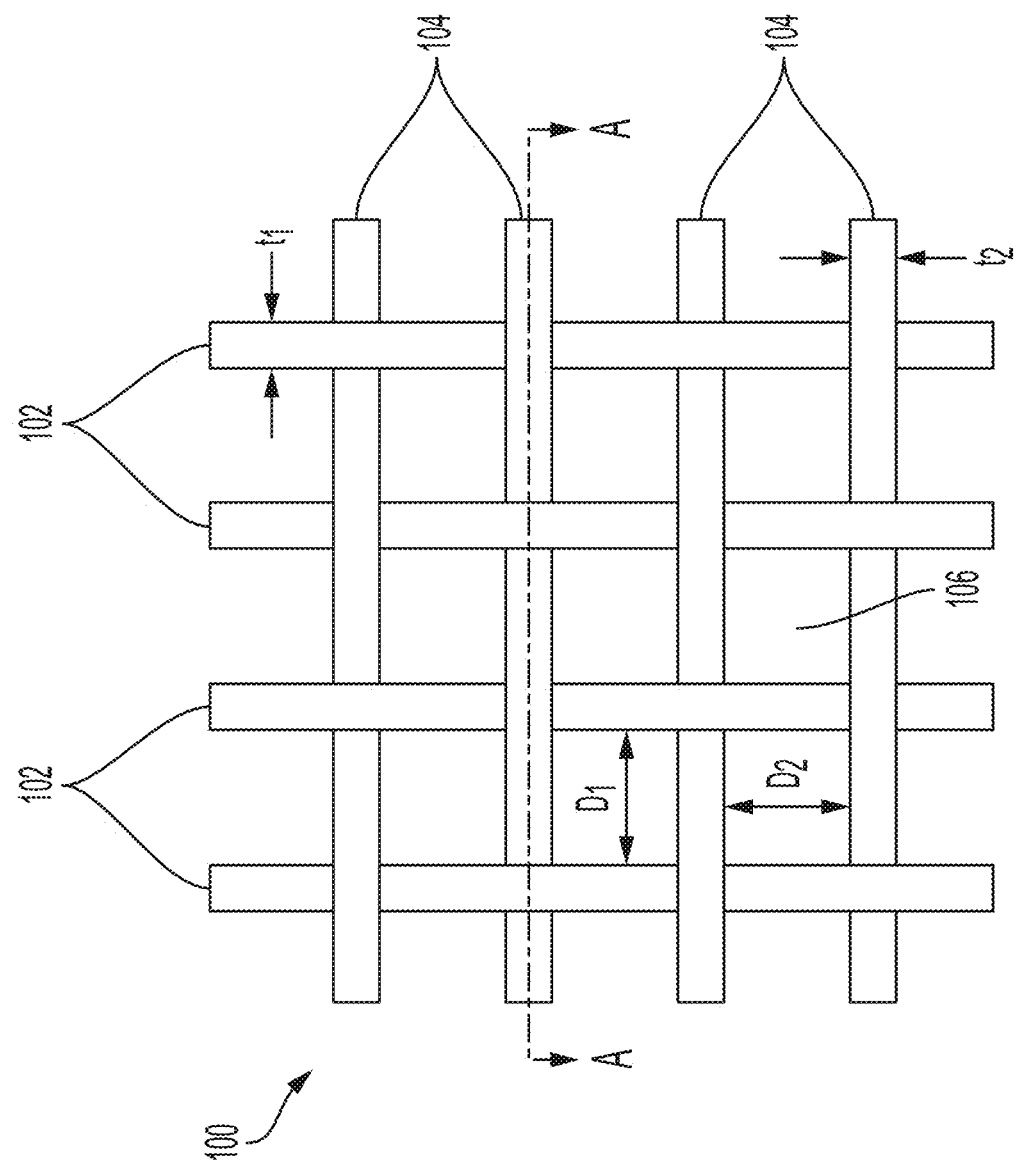
FIG. 1B is a two-dimensional plan view of the substrate of FIG. 1A.
Figure 1C:
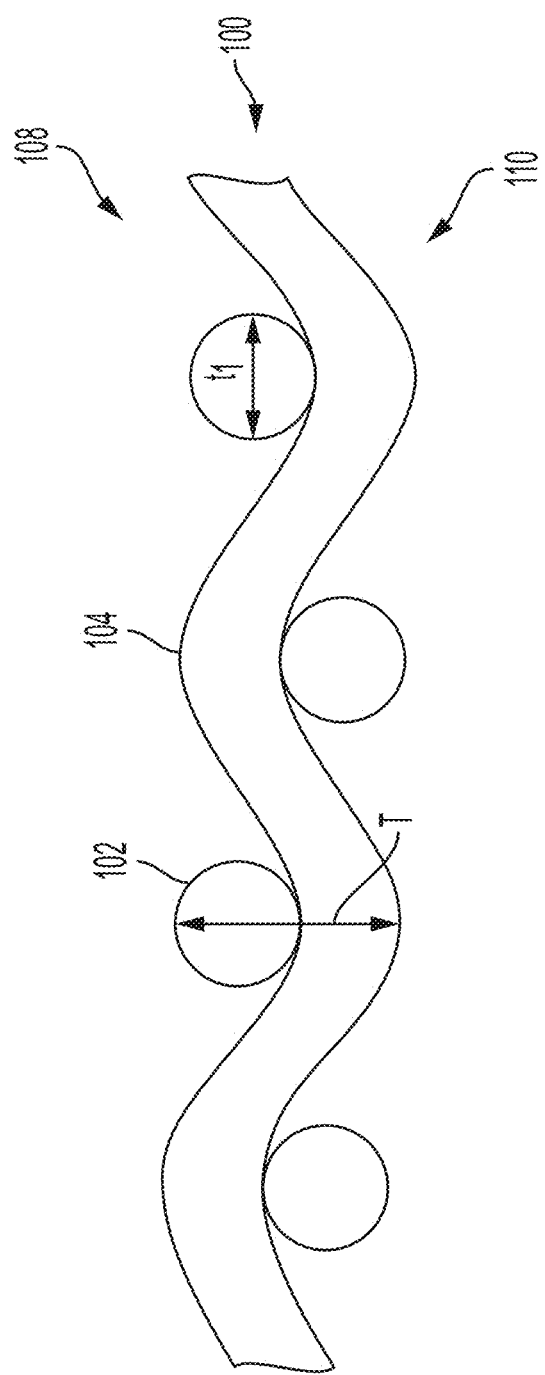
FIG. 1C is a cross-section along line A-A of the substrate in FIG. 1B.

FIGS. 1A and 1B show a three-dimensional (3D) perspective view and a two-dimensional (2D) plan view, respectively, of a cell culture substrate 100, according to an example of one or more embodiments of this disclosure. The cell culture substrate 100 is a woven mesh layer made of a first plurality of fibers 102 running in a first direction and a second plurality of fibers 104 running in a second direction. The woven fibers of the substrate 100 form a plurality of openings 106, which can be defined by one or more widths or diameters (e.g., $D_1$, $D_2$). The size and shape of the openings can vary based on the type of weave (e.g., number, shape and size of filaments; angle between intersecting filaments, etc.). A woven mesh may be characterized as, on a macro-scale, a two-dimensional sheet or layer. However, a close inspection of a woven mesh reveals a three-dimensional structure due to the rising and falling of intersecting fibers of the mesh. Thus, as shown in FIG. 1C, a thickness T of the woven mesh 100 may be thicker than the thickness of a single fiber (e.g., $t_1$). As used herein, the thickness T is the maximum thickness between a first side 108 and a second side 110 of the woven mesh. Without wishing to be bound by theory, it is believed that the three-dimensional structure of the substrate 100 is advantageous as it provides a large surface area for culturing adherent cells, and the structural rigidity of the mesh can provide a consistent and predictable cell culture matrix structure that enables uniform fluid flow.

In FIG. 1B, the openings 106 have a diameter $D_1$, defined as a distance between opposite fibers 102, and a diameter $D_2$, defined as a distance between opposite fibers 104. $D_1$ and $D_2$ can be equal or unequal, depending on the weave geometry. Where $D_1$ and $D_2$ are unequal, the larger can be referred to as the major diameter, and the smaller as the minor diameter. In some embodiments, the diameter of an opening may refer to the widest part of the opening. Unless otherwise specified, the opening diameter, as used herein, will refer to a distance between parallel fibers on opposite sides of an opening.

A given fiber of the plurality of fibers 102 has a thickness $t_1$, and a given fiber of the plurality of fibers 104 has a thickness $t_2$. In the case of fibers of round cross-section, as shown in FIG. 1A, or other three-dimensional cross-sections, the thicknesses $t_1$ and $t_2$ are the maximum diameters or thicknesses of the fiber cross-section. According to some embodiments, the plurality of fibers 102 all have the same thickness $t_1$, and the plurality of fiber 104 all have the same thickness $t_2$. In addition, $t_1$ and $t_2$ may be equal. However, in one or more embodiments, $t_1$ and $t_2$ are not equal such as when the plurality of fibers 102 are different from the plurality of fiber 104. In addition, each of the plurality of fibers 102 and plurality of fibers 104 may contain fibers of two or more different thicknesses (e.g., $t_{1a}$, $t_{1b}$ etc., and $t_{2a}$, $t_{2b}$, etc.). According to embodiments, the thicknesses $t_1$ and $t_2$ are large relative to the size of the cells cultured thereon, so that the fibers provide an approximation of a flat surface from the perspective of the cell, which can enable better cell attachment and growth as compared to some other solutions in which the fiber size is small (e.g., on the scale of the cell diameter). Due to three-dimensional nature of woven mesh, as shown in FIGS. 1A-1C, the 2D surface area of the fibers available for cell attachment and proliferation exceeds the surface area for attachment on an equivalent planar 2D surface.

In one or more embodiments, a fiber may have a diameter in a range of about 50 µm to about 1000 µm; about 100 µm to about 750 µm; about 125 µm to about 600 µm; about 150 µm to about 500 µm; about 200 µm to about 400 µm; about 200 µm to about 300 µm; or about 150 µm to about 300 µm. On a microscale level, due to the scale of the fiber compared to the cells (e.g., the fiber diameters being larger than the cells), the surface of monofilament fiber is presented as an approximation of a 2D surface for adherent cells to attach and proliferate. Fibers can be woven into a mesh with openings ranging from about 100 µm×100 µm to about 1000 µm×1000 µm. In some embodiments, the opening may have a diameter o about 50 µm to about 1000 µm; about 100 µm to about 750 µm; about 125 µm to about 600 µm; about 150 µm to about 500 µm; about 200 µm to about 400 µm; or about 200 µm to about 300 µm. These ranges of the filament diameters and opening diameters are examples of some embodiments, but are not intended to limit the possible feature sizes of the mesh according to all embodiments. The combination of fiber diameter and opening diameter is chosen to provide efficient and uniform fluid flow through the substrate when, for example, the cell culture matrix is comprises a number of adjacent mesh layers (e.g., a stack of individual layers or a rolled mesh layer).

Factors such as the fiber diameter, opening diameter, and weave type/pattern will determine the surface area available for cell attachment and growth. In addition, when the cell culture matrix includes a stack, roll, or other arrangement of overlapping substrate, the packing density of the cell culture matrix will impact the surface area of the packed bed matrix. Packing density can vary with the packing thickness of the substrate material (e.g., the space needed for a layer of the substrate). For example, if a stack of cell culture matrix has a certain height, each layer of the stack can be said to have a packing thickness determined by dividing the total height of the stack by the number of layers in the stack. The packing thickness will vary based on fiber diameter and weave, but can also vary based the alignment of adjacent layers in the stack. For instance, due to the three-dimensional nature of a woven layer, there is a certain amount of interlocking or overlapping that adjacent layers can accommodate based on their alignment with one another. In a first alignment, the adjacent layers can be tightly nestled together, but in a second alignment, the adjacent layers can have zero overlap, such as when the lower-most point of the upper layer is in direct contact with the upper-most point of the lower layer. It may be desirable for certain applications to provide a cell culture matrix with a lower density packing of layers (e.g., when higher permeability is a priority) or a higher density of packing (e.g., when maximizing substrate surface area is a priority). According to one or more embodiments, the packing thickness can be from about 50 µm to about 1000 µm; about 100 µm to about 750 µm; about 125 µm to about 600 µm; about 150 µm to about 500 µm; about 200 µm to about 400 µm; about 200 µm to about 300 µm.

The above structural factors can determine the surface area of a cell culture matrix, whether of a single layer of cell culture substrate or of a cell culture matrix having multiple layers of substrate). For example, in a particular embodiment, a single layer of woven mesh substrate having a circular shape and diameter of 6 cm can have an effective surface area of about 68 $cm^2$. The "effective surface area," as used herein, is the total surface area of fibers in a portion of substrate material that is available for cell attachment and growth. Unless stated otherwise, references to "surface area" refer to this effective surface area. According to one or more embodiments, a single woven mesh substrate layer with a diameter of 6 cm may have an effective surface area of about 50 $cm^2$ to about 90 $cm^2$; about 53 $cm^2$ to about 81 $cm^2$; about 68 $cm^2$; about 75 $cm^2$; or about 81 $cm^2$. These ranges of effective surface area are provided for example only, and some embodiments may have different effective surface areas. The cell culture matrix can also be characterized in terms of porosity, as discussed in the Examples herein.

The substrate mesh can be fabricated from monofilament or multifilament fibers of polymeric materials compatible in cell culture applications, including, for example, polystyrene, polyethylene terephthalate, polycarbonate, polyvinylpyrrolidone, polybutadiene, polyvinylchloride, polyethylene oxide, polypyrroles, and polypropylene oxide. Mesh substrates may have a different patterns or weaves, including, for example knitted, warp-knitted, or woven (e.g., plain weave, twilled weave, dutch weave, five needle weave).

The surface chemistry of the mesh filaments may need to be modified to provide desired cell adhesion properties. Such modifications can be made through the chemical treatment of the polymer material of the mesh or by grafting cell adhesion molecules to the filament surface. Alternatively, meshes can be coated with thin layer of biocompatible hydrogels that demonstrate cell adherence properties, including, for example, collagen or Matrigel®. Alternatively, surfaces of filament fibers of the mesh can be rendered with cell adhesive properties through the treatment processes with various types of plasmas, process gases, and/or chemicals known in the industry. In one or more embodiments, however, the mesh is capable of providing an efficient cell growth surface without surface treatment.

Figure 2B:
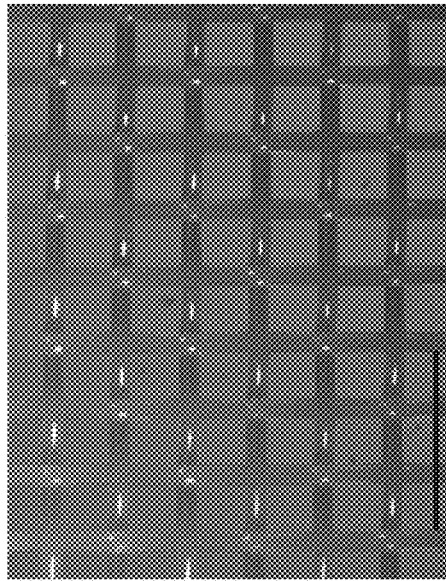
FIG. 2B shows an example of a cell culture substrate, according to some embodiments.
Figure 2C:
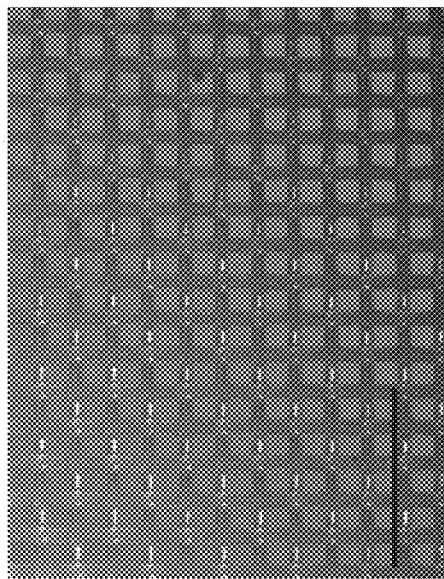
FIG. 2C shows an example of a cell culture substrate, according to some embodiments.
Figure 2A:
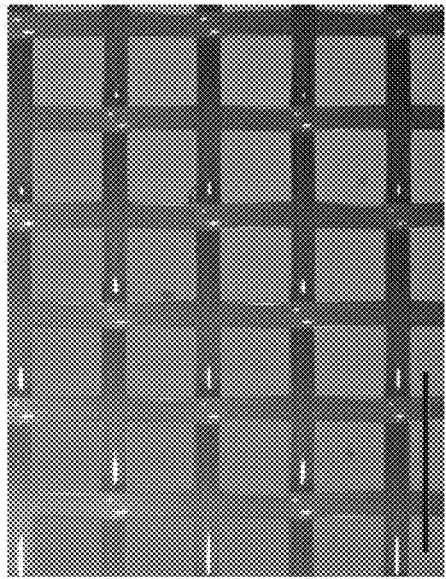
FIG. 2A shows an example of a cell culture substrate, according to some embodiments.

FIGS. 2A-2C show different examples of woven mesh according to some contemplated embodiments of this disclosure. The fiber diameter and opening size of these meshes are summarized in Table 1 below, as well as the approximate magnitude of increase in cell culture surface area provided by a single layer of the respective meshes relative to a comparable 2D surface. In Table 1, Mesh A refers to the mesh of FIG. 2A, Mesh B to the mesh of FIG. 2B, and Mesh C to the mesh of FIG. 2C. The three mesh geometries of Table 1 are examples only, and embodiments of this disclosure are not limited to these specific examples. Because Mesh C offers the highest surface area, it may be advantageous in achieving a high density in cell adhesion and proliferation, and thus provide the most efficient substrate for cell culturing. However, in some embodiments, it may be advantageous for the cell culture matrix to include a mesh with lower surface area, such as Mesh A or Mesh B, or a combination of meshes of different surface areas, to achieve a desired cell distribution or flow characteristics within the culture chamber, for example.

TABLE 1

Comparison of meshes in FIGS. 2A-2C, and the resulting increase in cell culture surface area as compared to a 2D surface.

|  | Mesh A | Mesh B | Mesh C |
|---|---|---|---|
| Fiber diameter | 273 ± 3 μm | 218 ± 3 μm | 158 ± 3 μm |
| Mesh opening | 790 × 790 μm | 523 × 523 μm | 244 × 244 μm |
| Surface area increase of one layer of mesh compared to 2D surface | ×1.6 | ×1.8 | ×2.5 |

As shown by the above table, the three-dimensional quality of the meshes provides increased surface area for cell attachment and proliferation compared to a planar 2D surface of comparable size. This increased surface area aids in the scalable performance achieved by embodiments of this disclosure. For process development and process validation studies, small-scale bioreactors are often required to save on reagent cost and increase experimental throughput Embodiments of this disclosure are applicable to such small-scale studies, but can be scaled-up to industrial or production scale, as well. For example, if 100 layers of Mesh C in the form of 2.2 cm diameter circles are packed into a cylindrical packed bed with a 2.2 cm internal diameter, the total surface area available for cells to attach and proliferate is equal to about 935 cm². To scale such bioreactor ten times, one could use a similar setup of a cylindrical packed bed with 7 cm internal diameter and 100 layers of the same mesh. In such a case, the total surface area would be equal 9,350 cm². In some embodiments, the available surface area is about 99,000 cm²/L or more. Because of the plug-type perfusion flow in a packed bed, the same flow rate expressed in ml/min/cm² of cross-sectioned packed bed surface area can be used in smaller-scale and larger-scale versions of the bioreactor. A larger surface area allows for higher seeding density and higher cell growth density. According to one or more embodiments, the cell culture substrate described herein has demonstrated cell seeding densities of up to 22,000 cells/cm² or more. For reference, the Corning HyperFlask® has a seeding density on the order of 20,000 cells/cm² on a two-dimensional surface.

Another advantage of the higher surface areas and high cell seeding or growing densities is that the cost of the embodiments disclosed herein can be the same or less than competing solution. Specifically, the cost per cellular product (e.g., per cell or per viral genome) can be equal to or less than other packed bed bioreactors.

In a further embodiment of the present disclosure discussed below, a woven mesh substrate can be packed in a cylindrical roll format within the bioreactor (see FIGS. 8 and 9). In such an embodiment, the scalability of the packed bed bioreactor can be achieved by increasing the overall length of the mesh strip and its height. The amount of mesh used in this cylindrical roll configuration can vary based on the desired packing density of the packed bed. For example, the cylindrical rolls can be densely packed in a tight roll or loosely packed in a loose roll. The density of packing will often be determined by the required cell culture substrate surface area required for a given application or scale. In one embodiment, the required length of the mesh can be calculated from the packed bed bioreactor diameter by using following formula:

$$L = \frac{\pi(R^2 - r^2)}{t} \quad \text{Equation 1}$$

where L is the total length of mesh required to pack the bioreactor (i.e., H in FIG. 8), R is the internal radius of packed bed culture chamber, r is the radius of an inner support (support 366 in FIG. 9) around which mesh is rolled, and t is the thickness of one layer of the mesh. In such a configuration, scalability of the bioreactor can be achieved by increasing diameter or width (i.e., W in FIG. 8) of the packed bed cylindrical roll and/or increasing the height H of the packed bed cylindrical roll, thus providing more substrate surface area for seeding and growing adherent cells.

By using a structurally defined culture matrix of sufficient rigidity, high-flow-resistance uniformity across the matrix or packed bed is achieved. According to various embodiments, the matrix can be deployed in monolayer or multilayer formats. This flexibility eliminates diffusional limitations and provides uniform delivery of nutrients and oxygen to cells attached to the matrix. In addition, the open matrix lacks any cell entrapment regions in the packed bed configuration, allowing for complete cell harvest with high viability at the end of culturing. The matrix also delivers packaging uniformity for the packed bed, and enables direct scalability from process development units to large-scale industrial bioprocessing unit. The ability to directly harvest cells from the packed bed eliminates the need of resuspending a matrix in a stirred or mechanically shaken vessel, which would add complexity and can inflict harmful shear stresses on the cells. Further, the high packing density of the cell culture matrix yields high bioprocess productivity in volumes manageable at the industrial scale.

Figure 3B:
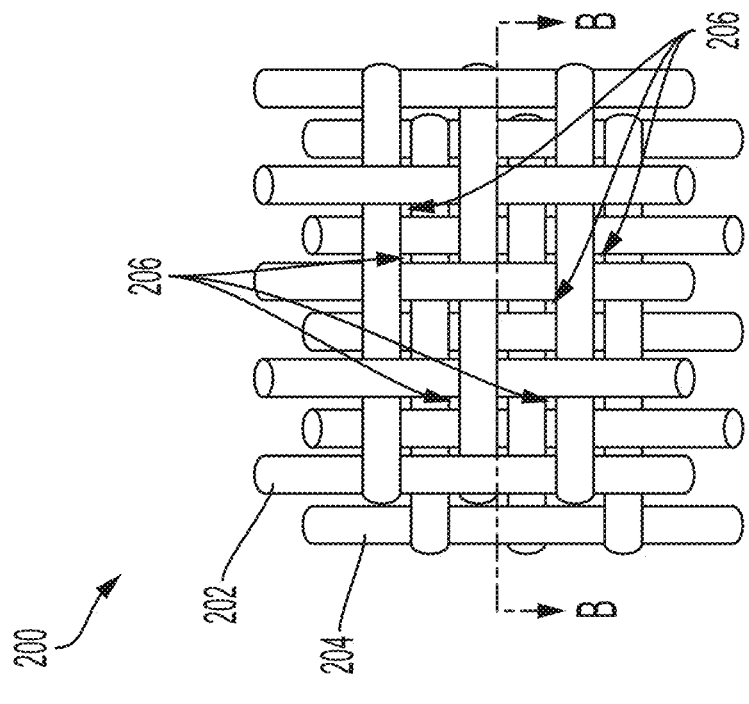
FIG. 3B shows a plan view of a multilayer cell culture substrate, according to one or more embodiments.
Figure 3A:
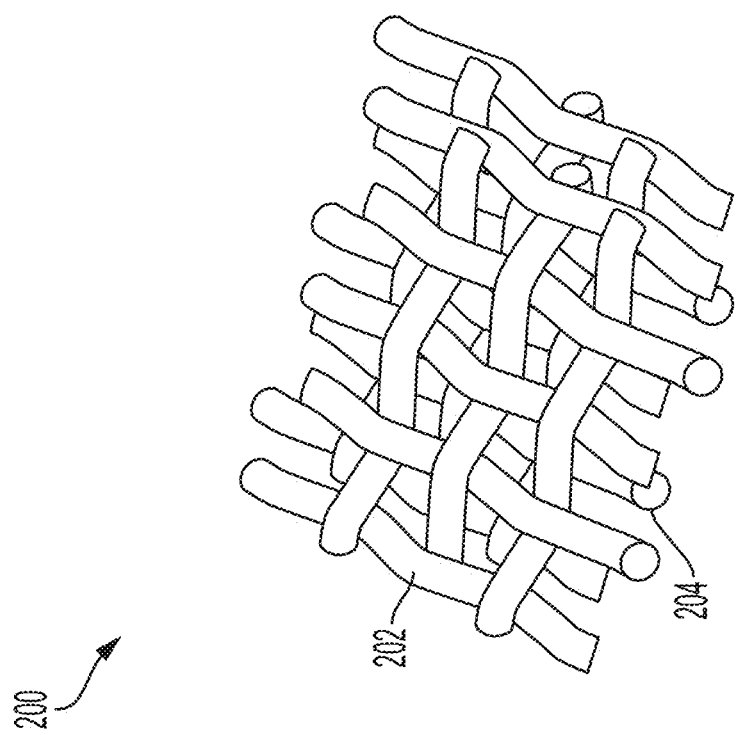
FIG. 3A shows a perspective view of a multilayer cell culture substrate, according to one or more embodiments.

FIG. 3A shows an embodiment of the matrix with a multilayer substrate 200, and FIG. 3B is a plan view of the same multilayer substrate 200. The multilayer substrate 200 includes a first mesh substrate layer 202 and a second mesh substrate layer 204. Despite the overlapping of the first and second substrate layers 202 and 204, the mesh geometries (e.g., ratio of opening diameters to fiber diameters) is such that the openings of the first and second substrate layers 202 and 204 overlap and provide paths for fluid to flow through the total thickness of the multilayer substrate 200, as shown by the filament-free openings 206 in FIG. 3B.

Figure 4:
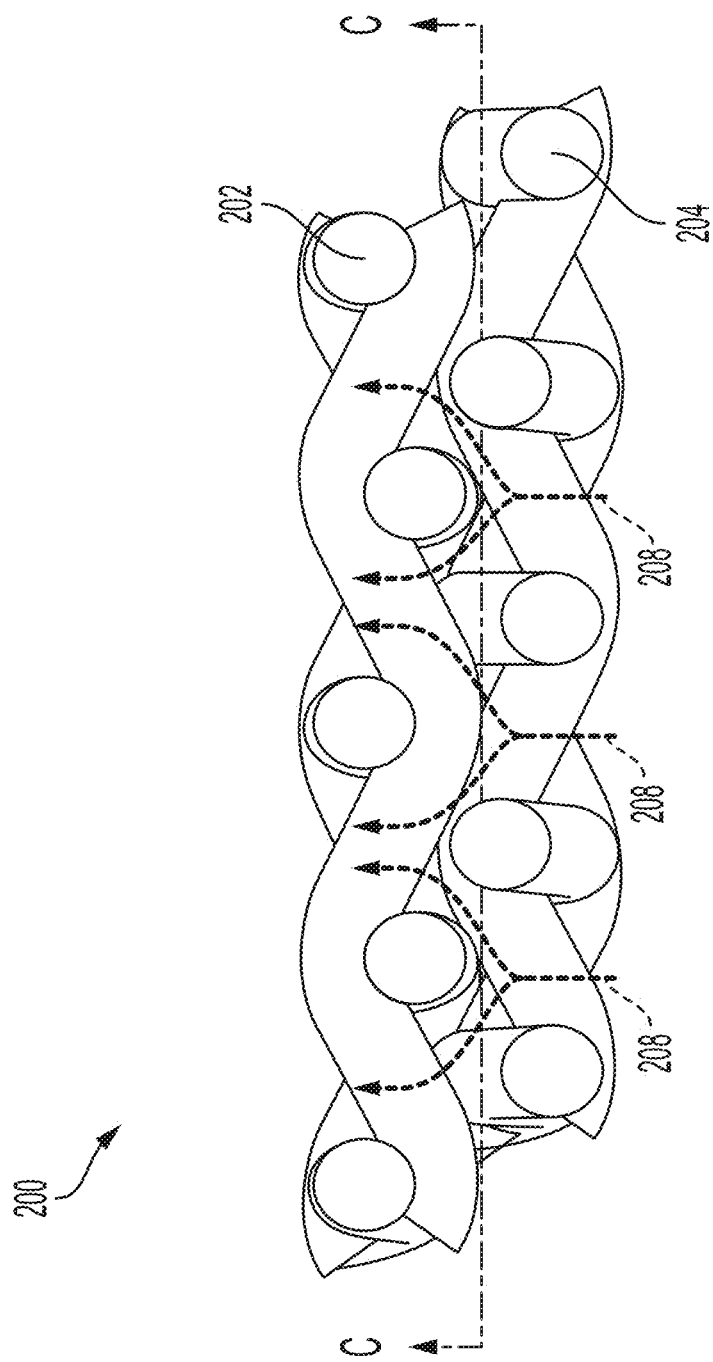
FIG. 4 shows a cross-section view along line B-B of the multilayer cell culture substrate of FIG. 3B, according to one or more embodiments.
Figure 5:
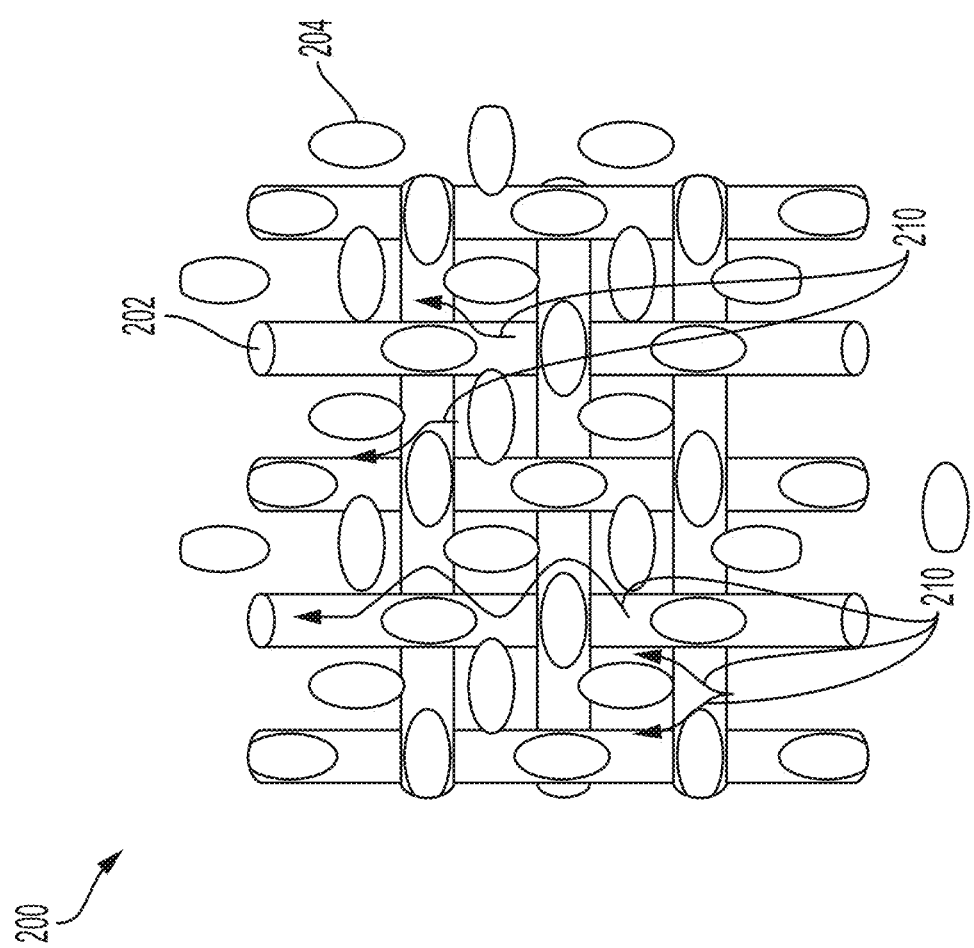
FIG. 5 shows a cross-section view along line C-C of the multilayer cell culture substrate of FIG. 4, according to one or more embodiments.

FIG. 4 shows a cross section view of the multilayer substrate 200 at line B-B in FIG. 3B. The arrows 208 show the possible fluid flow paths through openings in the second substrate layer 204 and then around filaments in the first substrate layer 202. The geometry of the mesh substrate layers is designed to allow efficient and uniform flow through one or multiple substrate layers. In addition, the structure of the matrix 200 can accommodate fluid flow through the matrix in multiple orientations. For example, as shown in FIG. 4, the direction of bulk fluid flow (as shown by arrows 208) is perpendicular to the major side surfaces of the first and second substrate layers 202 and 204. However, the matrix can also be oriented with respect to the flow such that the sides of the substrate layers are parallel to the bulk flow direction. FIG. 5 shows a cross section view of the multilayer substrate 200 along line C-C in FIG. 4, and the structure of matrix 200 allows for fluid flow (arrows 210)

through fluid pathways in the multilayer substrate 200. In addition to fluid flow being perpendicular or parallel to the first and second sides of the mesh layers, the matrix can be arranged with multiple pieces of substrate at intermediate angles, or even in random arrangements with respect to fluid flow. This flexibility in orientation is enabled by the essentially isotropic flow behavior of the woven substrate. In contrast, substrates for adherent cells in existing bioreactors do not exhibit this behavior and instead their packed beds tend to create preferential flow channels and have substrate materials with anisotropic permeability. The flexibility of the matrix of the current disclosure allows for its use in various applications and bioreactor or container designs while enabling better and more uniform permeability throughout the bioreactor vessel.

As discussed herein, the cell culture substrate can be used within a bioreactor vessel, according to one or more embodiments. For example, the substrate can be used in a packed bed bioreactor configuration, or in other configurations within a three-dimensional culture chamber. However, embodiments are not limited to a three-dimensional culture space, and it is contemplated that the substrate can be used in what may be considered a two-dimensional culture surface configuration, where the one or more layers of the substrate lay flat, such as within a flat-bottomed culture dish, to provide a culture substrate for cells. Due to contamination concerns, the vessel can be a single-use vessel that can be disposed of after use.

Figure 6:
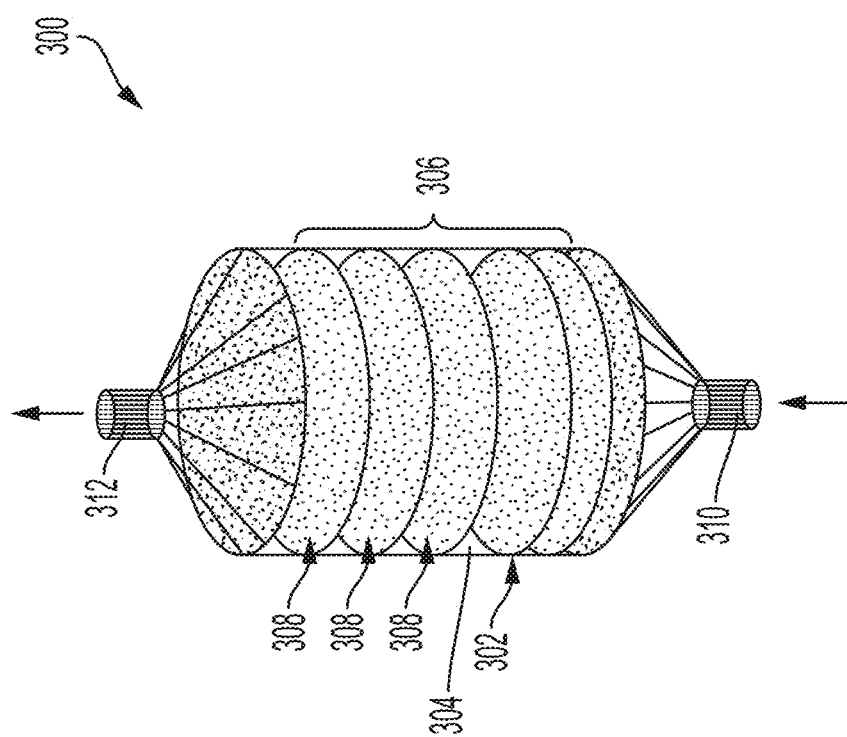
FIG. 6 shows a schematic view of a cell culture system, according to one or more embodiments.

A cell culture system is provided, according to one or more embodiments, in which the cell culture matrix is used within a culture chamber of a bioreactor vessel. FIG. 6 shows an example of a cell culture system 300 that includes a bioreactor vessel 302 having a cell culture chamber 304 in the interior of the bioreactor vessel 302. Within the cell culture chamber 304 is a cell culture matrix 306 that is made from a stack of substrate layers 308. The substrate layers 308 are stacked with the first or second side of a substrate layer facing a first or second side of an adjacent substrate layer. The bioreactor vessel 300 has an inlet 310 at one end for the input of media, cells, and/or nutrients into the culture chamber 304, and an outlet 312 at the opposite end for removing media, cells, or cell products from the culture chamber 304. By allowing stacking of substrate layers in this way, the system can be easily scaled up without negative impacts on cell attachment and proliferation, due to the defined structure and efficient fluid flow through the stacked substrates. While the vessel 300 may generally be described as having an inlet 310 and an outlet 312, some embodiments may use one or both of the inlet 310 and outlet 312 for flowing media, cells, or other contents both into and out of the culture chamber 304. For example, inlet 310 may be used for flowing media or cells into the culture chamber 304 during cell seeding, perfusion, or culturing phases, but may also be used for removing one or more of media, cells, or cell products through the inlet 310 in a harvesting phase. Thus, the terms "inlet" and "outlet" are not intended to restrict the function of those openings.

In one or more embodiments, flow resistance and volumetric density of the packed bed can be controlled by interleaving substrate layers of different geometries. In particular, mesh size and geometry (e.g., fiber diameter, opening diameter, and/or opening geometry) define the fluid flow resistance in packed bed format. By interlaying meshes of different sizes and geometries, flow resistance can be controlled or varied in one or more specific portions of the bioreactor. This will enable better uniformity of liquid perfusion in the packed bed. For example, 10 layers of Mesh A (Table 1) followed by 10 layers of Mesh B (Table 1) and followed by 10 layers of Mesh C (Table 1) can be stacked to achieve a desired packed bed characteristic. As another example, the packed bed may start with 10 layers of Mesh B, followed by 50 layers of Mesh C, followed by 10 layers of Mesh B. Such repetition pattern may continue until the full bioreactor is packed with mesh. These are examples only, and used for illustrative purposes without intending to be limiting on the possible combinations. Indeed, various combinations of meshes of different sizes are possible to obtain different profiles of volumetric density of cells growth surface and flow resistance. For example, a packed bed column with zones of varying volumetric cells densities (e.g., a series of zones creating a pattern of low/high/low/high, etc. densities) can be assembled by interleaving meshes of different sizes.

Figure 7:
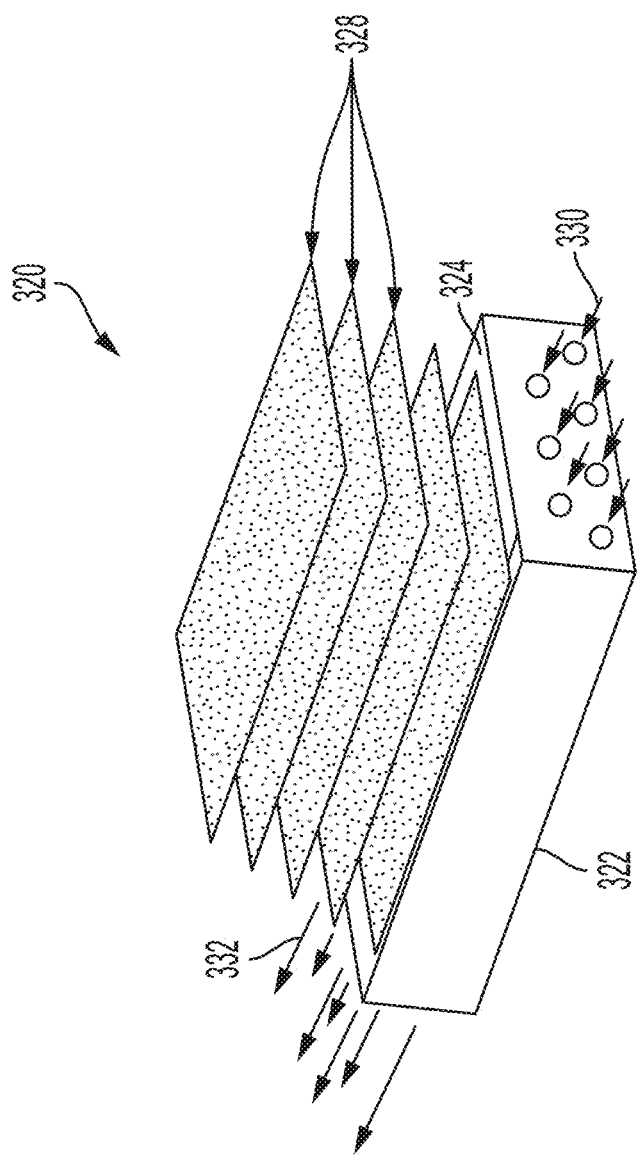
FIG. 7 shows a schematic view of a cell culture system, according to one or more embodiments.

In FIG. 6, the bulk flow direction is in a direction from the inlet 310 to the outlet 312, and, in this example, the first and second major sides of the substrate layers 308 are perpendicular to the bulk flow direction. In contrast, the example shown in FIG. 7 is of an embodiment in which the system 320 includes a bioreactor vessel 322 and stack of substrates 328 within the culture space 324 that have first and second sides that are parallel to a bulk flow direction, which corresponds to a direction shown by the flow lines into the inlets 330 and out of the outlets 332. Thus, the matrices of embodiments of this disclosure can be employed in either configuration. In each of systems 300 and 320, the substrates 308, 328 are sized and shaped to fill the interior space defined by the culture chamber 304, 324 so that the culture spaces in each vessel are filled for cell growth surfaces to maximize efficiency in terms of cells per unit volume. Although FIG. 7 shows multiple inlets 330 and multiple outlets 332, it is contemplated that the system 320 may be fed by a single inlet and have a single outlet. However, according to various embodiments herein, distribution plates can be used to help distribute the media, cells, or nutrients across a cross-section of the packed bed and thus improve uniformity of fluid flow through the packed bed. As such, the multiple inlets 330 represent how a distribution plate can be provided with a plurality of holes across the packed-bed cross-section for creating more uniform flow.

Figure 8:
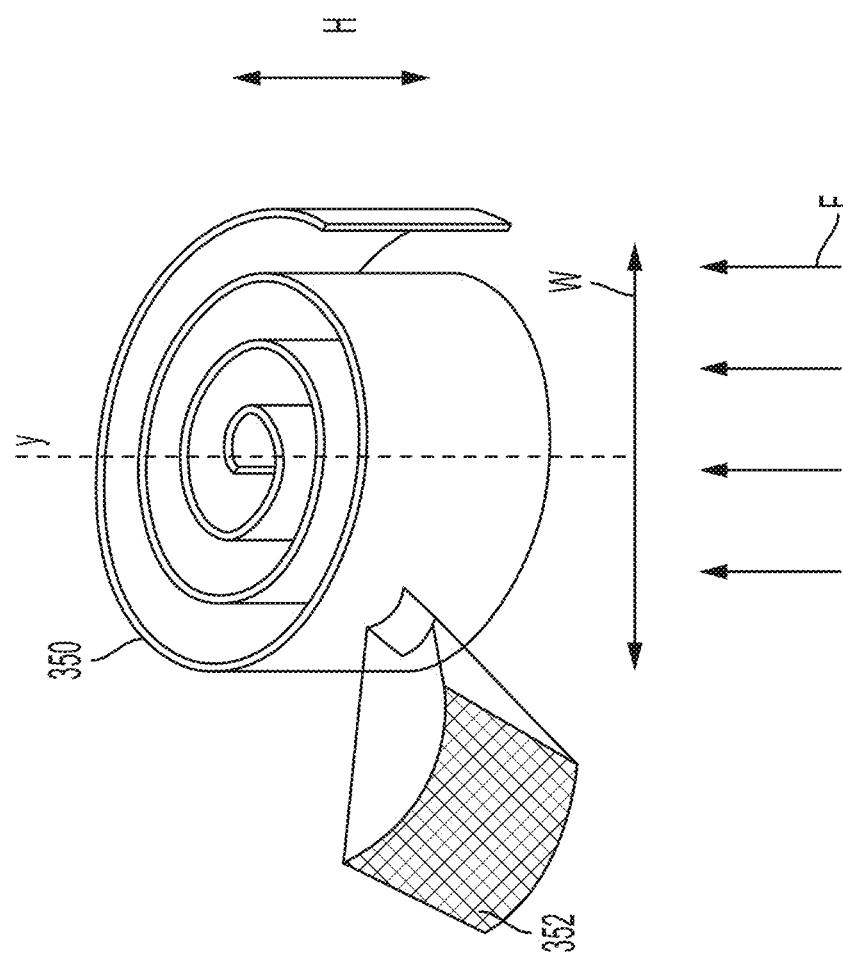
FIG. 8 shows a cell culture matrix in a rolled cylindrical configuration, according to one or more embodiments.
Figure 9:
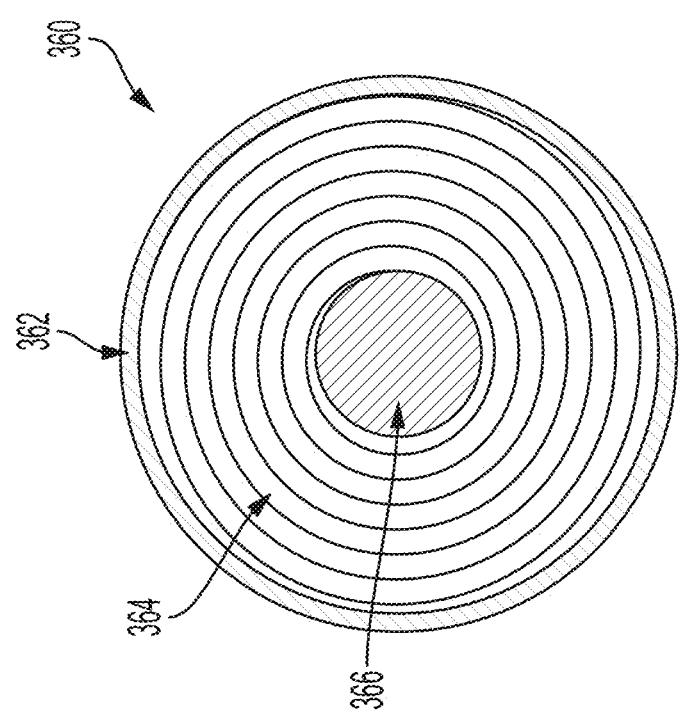
FIG. 9 shows a cell culture system incorporated a rolled cylindrical cell culture matrix, according to one or more embodiments.

FIG. 8 shows an embodiment of the matrix in which the substrate is formed into a cylindrical roll 350. For example, a sheet of a matrix material that includes a mesh substrate 352 is rolled into a cylinder about a central longitudinal axis y. The cylindrical roll 350 has a width W along a dimension perpendicular to the central longitudinal axis y and a height H along a direction perpendicular to the central longitudinal axis y. In one or more preferred embodiments, the cylindrical roll 350 is designed to be within a bioreactor vessel such that the central longitudinal axis y is parallel to a direction of bulk flow F of fluid through the bioreactor or culture chamber that houses the cylindrical roll. FIG. 9 shows a cell culture system 360 having a bioreactor vessel 362 that houses a cell culture matrix 364 in such a cylindrical roll configuration. Like the cylindrical roll 350 in FIG. 8, the cell culture matrix 364 has a central longitudinal axis, which, in FIG. 9, extends into the page. The system 360 further includes a central support member 366 around which the cell culture matrix 364 is position. The central support member 366 can be provided purely for physical support and/or alignment of the cell culture matrix 364, but can also provide other functions, according to some embodiments. For example, the central support member 366 can be provided with one or more openings for supplying media to the cell culture matrix 364 along the length H of the matrix. In other embodiments, the central support member 366 may include one or more attachment sites for holding one or more portions of the cell culture matrix 364 at the inner part of the cylindrical roll. These attachment sites may be hooks, clasps, posts, clamps, or other means of attaching the mesh sheet to the central support member 366.

FIG. 10A shows a cell culture system 400 according to one or more embodiments. The system 400 includes a bioreactor 402 housing the cell culture matrix of one or more embodiments disclosed herein. The bioreactor 402 can be fluidly connected to a media conditioning vessel 404, and the system is capable of supplying a cell culture media 406 within the conditioning vessel 404 to the bioreactor 402. The media conditioning vessel 404 can include sensors and control components found in typical bioreactor used in the bioprocessing industry for a suspension batch, fed-batch or perfusion culture. These include but are not limited to DO oxygen sensors, pH sensors, oxygenator/gas sparging unit, temperature probes, and nutrient addition and base addition ports. A gas mixture supplied to sparging unit can be controlled by a gas flow controller for $N_2$, $O_2$, and $CO_2$ gasses. The media conditioning vessel 404 also contains an impeller for media mixing. All media parameters measured by sensors listed above can be controlled by a media conditioning control unit 418 in communication with the media conditioning vessel 404, and capable of measuring and/or adjusting the conditions of the cell culture media 406 to the desired levels. As shown in FIG. 10A, the media conditioning vessel 404 is provided as a vessel that is separate from the bioreactor vessel 402. This can have advantages in terms of being able to condition the media separate from where the cells are cultured, and then supplying the conditioned media to the cell culture space. However, in some embodiments, media conditioning can be performed within the bioreactor vessel 402.

The media from the media 406 conditioning vessel 404 is delivered to the bioreactor 402 via an inlet 408, which may also include an injection port for cell inoculum to seed and begin culturing of cells. The bioreactor vessel 402 may also include on or more outlets 410 through which the cell culture media 406 exits the vessel 402. In addition, cells or cell products may be output through the outlet 410. To analyze the contents of the outflow from the bioreactor 402, one or more sensors 412 may be provided in the line. In some embodiments, the system 400 includes a flow control unit 414 for controlling the flow into the bioreactor 402. For example, the flow control unit 414 may receive a signal from the one or more sensors 412 (e.g., an $O_2$ sensor) and, based on the signal, adjust the flow into the bioreactor 402 by sending a signal to a pump 416 (e.g., peristaltic pump) upstream of the inlet 408 to the bioreactor 402. Thus, based on one or a combination of factors measured by the sensors 412, the pump 416 can control the flow into the bioreactor 402 to obtain the desired cell culturing conditions.

The media perfusion rate is controlled by the signal processing unit 414 that collects and compares sensors signals from media conditioning vessel 404 and sensors located at the packed bed bioreactor outlet 410. Because of the pack flow nature of media perfusion through the packed bed bioreactor 402, nutrients, pH and oxygen gradients are developed along the packed bed. The perfusion flow rate of the bioreactor can be automatically controlled by the flow control unit 414 operably connected to the peristaltic pump 416, according to the flow chart in FIG. 11.

One or more embodiments of this disclosure offer a cell inoculation step that is different from conventional methods. In conventional methods, a pack bed with a conventional matrix is filled with culture media and concentrated inoculum is injected into the media circulation loop. The cell suspension is pumped through the bioreactor at increased flow rate to reduce nonuniformity of cell seeding via capture on the conventional packed bed matrix. In such conventional methods, the pumping of cells in the circulation loop at an elevated flow rate continues for perhaps several hours until the majority of the cells are captured in packed bed bioreactor. However, because of the nonuniform deep bed filtration nature of conventional packed bed bioreactors, cells are distributed nonuniformly inside the packed bed with the higher cell density at the inlet region of the bioreactor and lower cell density at the outlet region of the bioreactor.

In contrast, according to embodiments of the present disclosure, cell inoculum of equal volume to the void volume of the culture chamber in the bioreactor is directly injected into the packed bed through a cell inoculum injection port at the inlet 408 of the bioreactor 402 (FIG. 10A). The cell suspension is then uniformly distributed inside the packed bed because of uniform and continuous fluidic passages present in the cell culture matrix described herein. To prevent cells sedimentation due to gravity forces at the initial seeding stage, media perfusion can be started immediately after the inoculum injection. The perfusion flow rate is maintained below a preprogrammed threshold to balance the force of gravity and to avoid cells being washed from the packed bed bioreactor. Thus, at the initial cell attachment stage, cells are gently tumbled inside the packed bed and uniform cells distribution and attachment on available substrate surface is achieved.

Figure 10B:
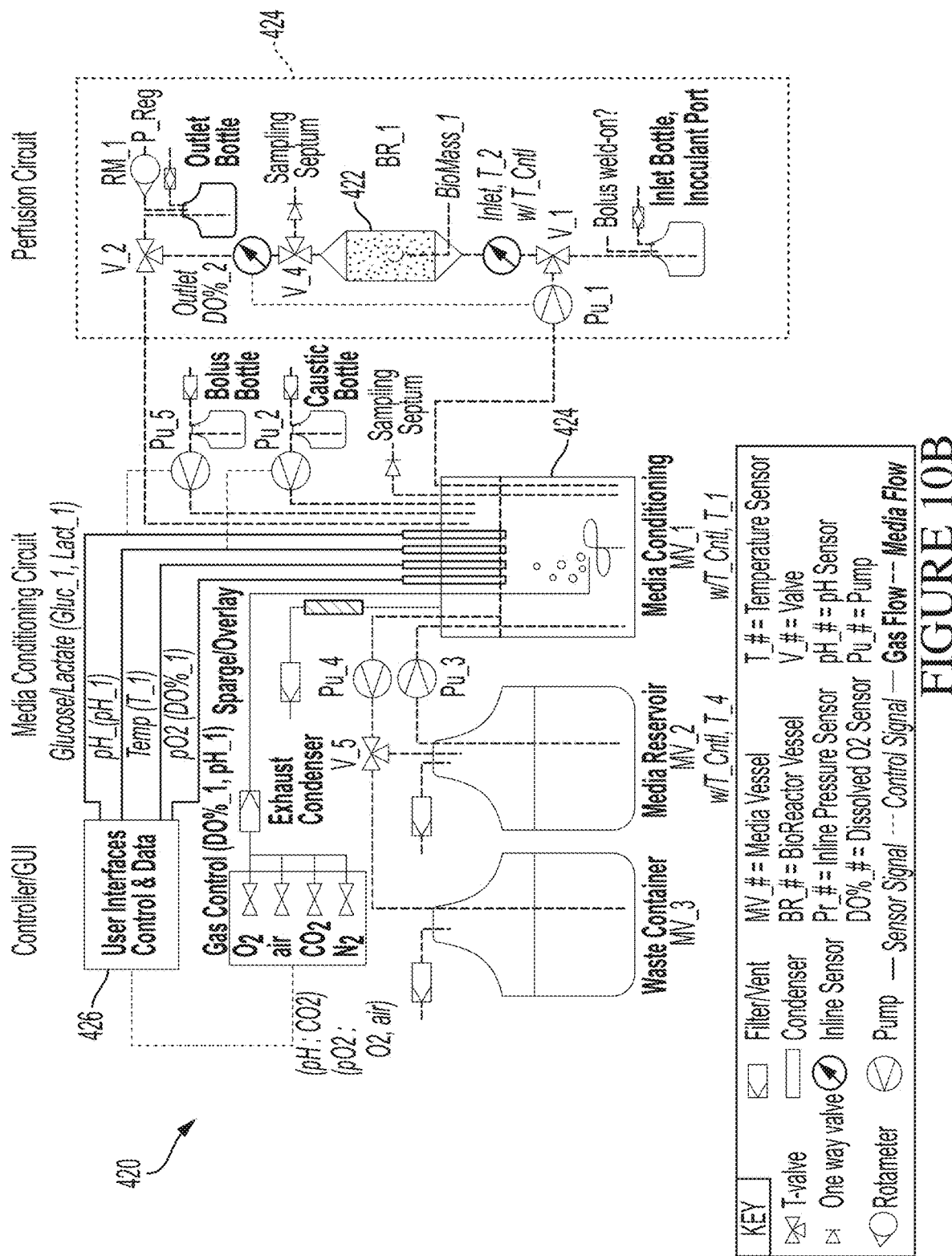
FIG. 10B is a detailed schematic of a cell culture system, according to one or more embodiments.

FIG. 10B shows a more detailed schematic of a cell culture system 420 according to one or more embodiments. The basic construction of the system 420 is similar to the system 400 in FIG. 10A, with a packed bed bioreactor 422 having a vessel containing a packed bed of cell culture material, such as a PET woven mesh, and a separate media conditioning vessel 424. In contrast to system 400, however, system 420 shows the details of the system, including sensors, user interface and controls, and various inlet and outlets for media and cells. According to some embodiments, the media conditioning vessel 424 is controlled by the controller 426 to provide the proper temperature, pH, $O_2$, and nutrients. While in some embodiments, the bioreactor 422 can also be controlled by the controller 426, in other embodiments the bioreactor 422 is provided in a separate perfusion circuit 428, where a pump is used to control the flow rate of media through the perfusion circuit 428 based on the detection of O2 at or near the outlet of the bioreactor 422.

Figure 11A:
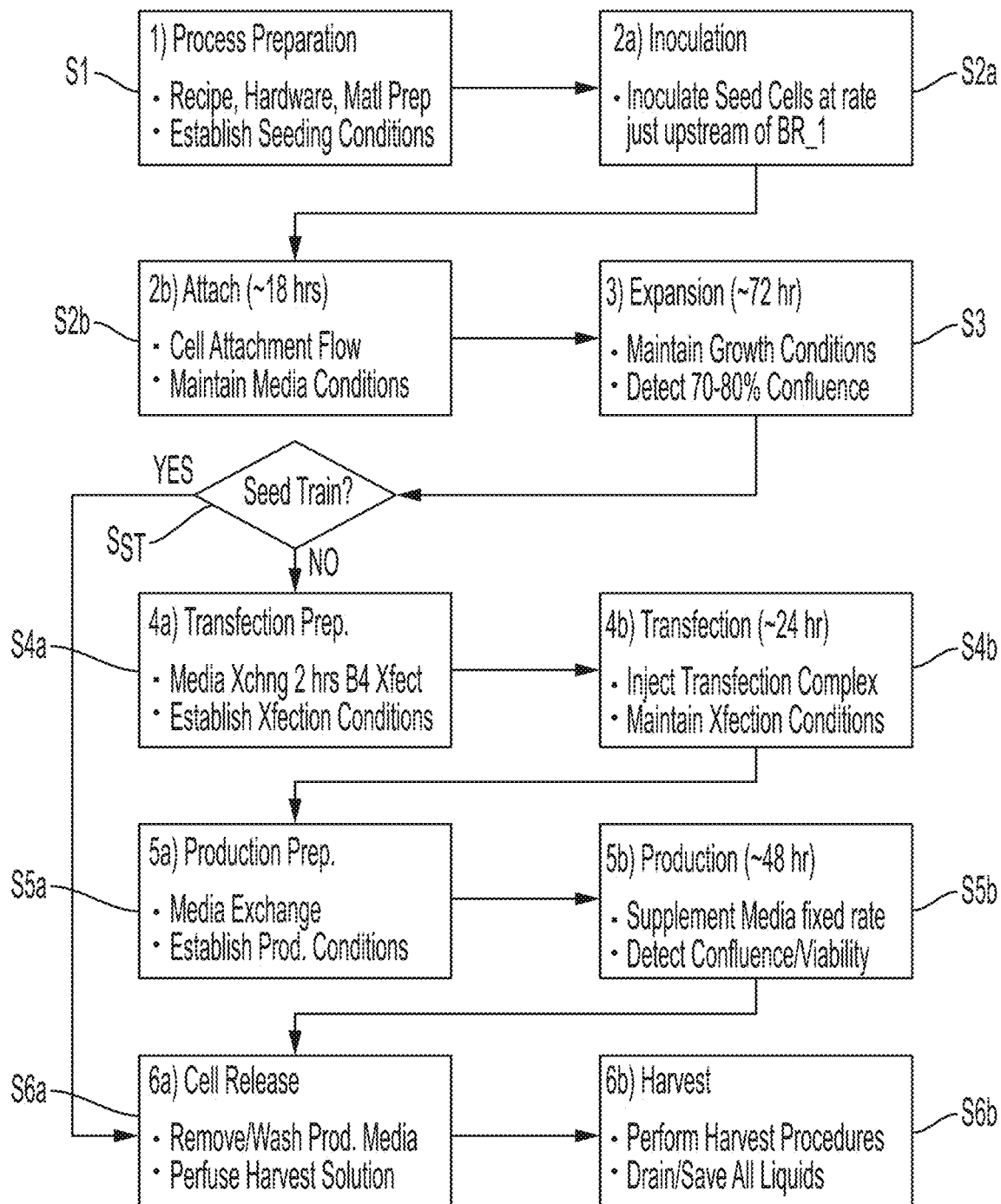
FIG. 11A shows a process flow chart for culturing cells on a cell culture system, according to one or more embodiments.

The systems of FIGS. 10A and 10B can be operated according to process steps according to one or more embodiments. As shown in FIG. 11A, these process steps can include process preparation (S1), seeding and attaching cells (S2a, S2b), cell expansion (S3), transfection (S4a, S4b), production of viral vector (S5a, S5b), and harvesting (S6a, S6b).

Figure 11B:
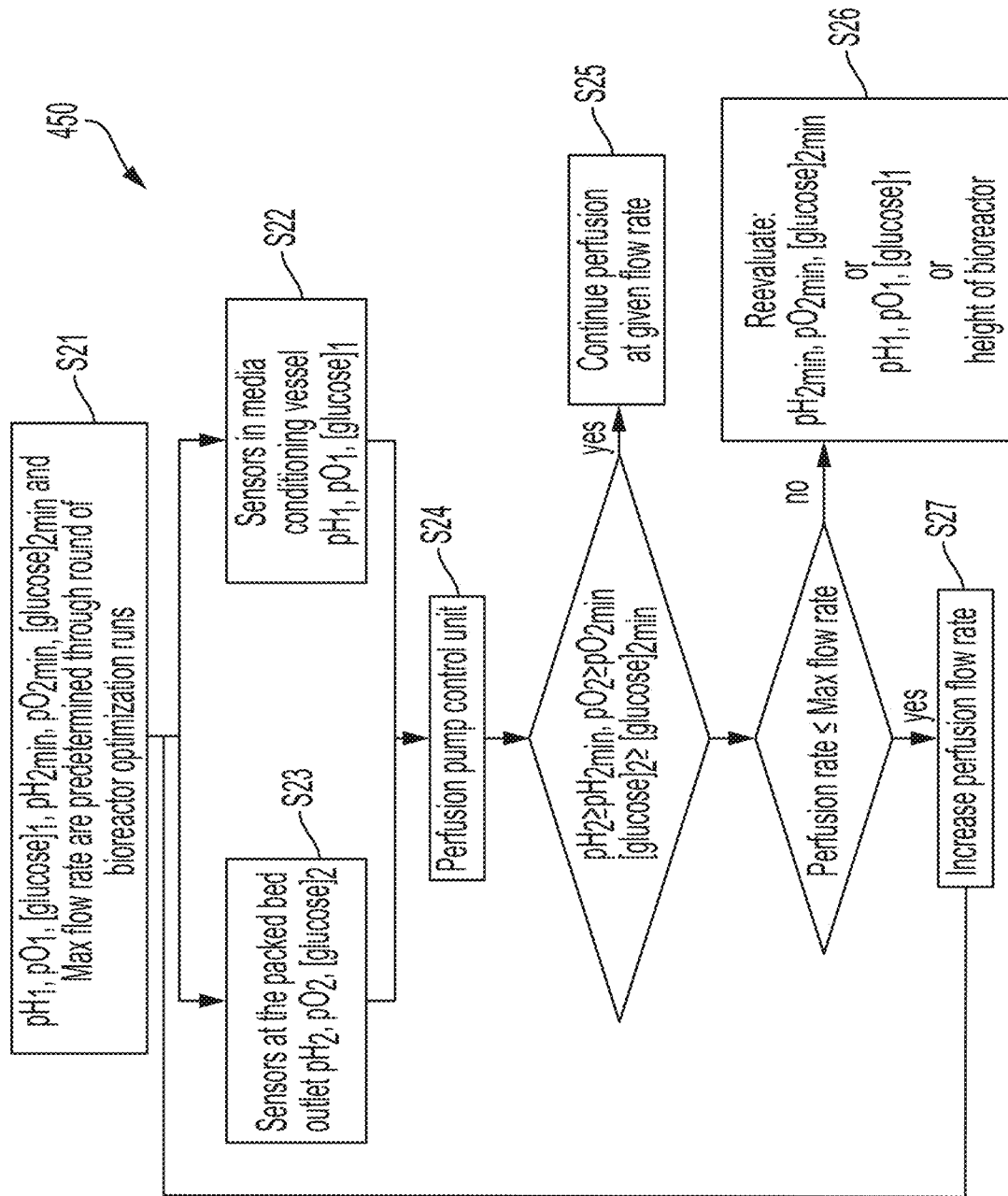
FIG. 11B shows an operation for controlling a perfusion flow rate of a cell culture system, according to one or more embodiments.

FIG. 11 shows an example of a method 450 for controlling the flow of a perfusion bioreactor system, such as the system 400 of FIG. 10A or 10B. According to the method 450, certain parameters of the system 400 are predetermined at step S21 through bioreactor optimization runs. From these optimization runs, the values of $pH_1$, $pO_1$, $[glucose]_1$, $pH_2$, $pO_2$, $[glucose]_2$, and maximum flow rate can be determined. The values for $pH_1$, $pO_1$, and $[glucose]_1$ are measured within the cell culture chamber of the bioreactor 402 at step S22, and $pH_2$, $pO_2$, and $[glucose]_2$ are measured by sensors 412 at the outlet of the bioreactor vessel 402 at step S23. Based on these values at S22 and S23, a perfusion pump control unit makes determinations at S24 to maintain or adjust the perfusion flow rate. For example, a perfusion flow rate of the cell culture media to the cell culture chamber may be continued at a present rate if at least one of $pH_2 \geq pH_{2min}$, $pO_2 \geq pO_{2min}$, and $[glucose]_2 \geq [glucose]_{2min}$ (S25). If the current flow rate is less than or equal to a predetermined max flow rate of the cell culture system, the perfusion flow rate is increased (S27). Further, if the current flow rate is not less than or equal to the predetermined max flow rate of the cell culture system, a controller of the cell culture system can reevaluate at least one of: (1) $pH_{2min}$, $pO_{2min}$, and $[glucose]_{2min}$; (2) $pH_1$, $pO_1$, and $[glucose]_1$; and (3) a height of the bioreactor vessel (S26).

The cell culture matrix can be arranged in multiple configurations within the culture chamber depending on the desired system. For example, in one or more embodiments, the system includes one or more layers of the substrate with a width extending across the width of a defined cell culture space in the culture chamber. Multiple layers of the substrate may be stacked in this way to a predetermined height. As discussed above, the substrate layers may be arranged such that the first and second sides of one or more layers are perpendicular to a bulk flow direction of culture media through the defined culture space within the culture chamber, or the first and second sides of one or more layers may be parallel to the bulk flow direction. In one or more embodiments, the cell culture matrix includes one or more substrate layers at a first orientation with respect to the bulk flow, and one or more other layers at a second orientation that is different from the first orientation. For example, various layers may have first and second sides that are parallel or perpendicular to the bulk flow direction, or at some angle in between.

In one or more embodiments, the cell culture system includes a plurality of discrete pieces of the cell culture substrate in a packed bed configuration, where the length and or width of the pieces of substrate are small relative to the culture chamber. As used herein, the pieces of substrate are considered to have a length and/or width that is small relative to the culture chamber when the length and/or width of the piece of substrate is about 50% or less of the length and/or width of the culture space. Thus, the cell culture system may include a plurality of pieces of substrate packed into the culture space in a desired arrangement. The arrangement of substrate pieces may be random or semi-random, or may have a predetermined order or alignment, such as the pieces being oriented in a substantially similar orientation (e.g., horizontal, vertical, or at an angle between 0° and 90° relative to the bulk flow direction).

The "defined culture space," as used herein, refers to a space within the culture chamber occupied by the cell culture matrix and in which cell seeding and/or culturing is to occur. The defined culture space can fill approximately the entirety of the culture chamber, or may occupy a portion of the space within the culture chamber. As used herein, the "bulk flow direction" is defined as a direction of bulk mass flow of fluid or culture media through or over the cell culture matrix during the culturing of cells, and/or during the inflow or outflow of culture media to the culture chamber.

In one or more embodiments, the cell culture matrix is secured within the culture chamber by a fixing mechanism. The fixing mechanism may secure a portion of the cell culture matrix to a wall of the culture chamber that surrounds the matrix, or to a chamber wall at one end of the culture chamber. In some embodiments, the fixing mechanism adheres a portion of the cell culture matrix to a member running through the culture chamber, such as member running parallel to the longitudinal axis of the culture chamber, or to a member running perpendicular to the longitudinal axis. However, in one or more other embodiments, the cell culture matrix may be contained within the culture chamber without being fixedly attached to the wall of the chamber or bioreactor vessel. For example, the matrix may be contained by the boundaries of the culture chamber or other structural members within the chamber such that the matrix is held within a predetermined area of the bioreactor vessel without the matrix being fixedly secured to those boundaries or structural members.

One aspect of some embodiments provides a bioreactor vessel in a roller bottle configuration. The culture chamber is capable of containing a cell culture matrix and substrate according to one or more of the embodiments described in this disclosure. In the roller bottle configuration, the bioreactor vessel may be operably attached to a means for moving the bioreactor vessel about a central longitudinal axis of the vessel. For example, the bioreactor vessel may be rotated about the central longitudinal axis. The rotation may be continuous (e.g., continuing in one direction) or discontinuous (e.g., an intermittent rotation in a single direction or alternating directions, or oscillating in back and forth rotational directions). In operation, the rotation of the bioreactor vessel causes movement of cells and/or fluid within the chamber. This movement can be considered relative with respect to the walls of the chamber. For example, as the bioreactor vessel rotates about its central longitudinal axis, gravity may cause the fluid, culture media, and/or unadhered cells to remain toward a lower portion of the chamber. However, in one or more embodiments, the cell culture matrix is essentially fixed with respect to the vessel, and thus rotates with the vessel. In one or more other embodiments, the cell culture matrix can be unattached and free to move to a desired degree relative to the vessel as the vessel rotates. The cells may adhere to the cell culture matrix, while the movement of the vessel allows the cells to receive exposure to both the cell culture media or liquid, and to oxygen or other gases within the culture chamber.

By using a cell culture matrix according to embodiments of this disclosure, such as a matrix including a woven or mesh substrate, the roller bottle vessel is provided with an increased surface area available for adherent cells to attach, proliferate, and function. In particular, using a substrate of a woven mesh of monofilament polymer material within the roller bottle, the surface area may increase by of about 2.4 to about 4.8 times, or to about 10 times that of a standard roller bottle. As discussed herein, each monofilament strand of the mesh substrate is capable of presenting itself as 2D surface for adherent cells to attach. In addition, multiple layers of mesh can we arranged in roller bottle, resulting in increases of total available surface area ranging from about 2 to 20 times that of a standard roller bottle. Thus, existing roller bottle facilities and processing, including cell seeding, media exchange, and cell harvesting, can be modified by the addition of the improved cell culture matrix disclosed herein, with minimal impact on existing operation infrastructure and processing steps.

The bioreactor vessel optionally includes one or more outlets capable of being attached to inlet and/or outlet means. Through the one or more outlets, liquid, media, or cells can be supplied to or removed from the chamber. A single port in the vessel may act as both the inlet and outlet, or multiple ports may be provided for dedicated inlets and outlets.

The packed bed cell culture matrix of one or more embodiments can consist of the woven cell culture mesh substrate without any other form of cell culture substrate disposed in or interspersed with the cell culture matrix. That is, the woven cell culture mesh substrate of embodiments of this disclosure are effective cell culture substrates without requiring the type of irregular, non-woven substrates used in existing solution. This enables cell culture systems of simplified design and construction, while providing a high-density cell culture substrate with the other advantages discussed herein related to flow uniformity, harvestability, etc.

As discussed herein, the cell culture substrates and bioreactor systems provided offer numerous advantages. For example, the embodiments of this disclosure can support the production of any of a number of viral vectors, such as AAV (all serotypes) and lentivirus, and can be applied toward in vivo and ex vivo gene therapy applications. The uniform cell seeding and distribution maximizes viral vector yield per vessel, and the designs enable harvesting of viable cells, which can be useful for seed trains consisting of multiple expansion periods using the same platform. In addition, the embodiments herein are scalable from process development scale to production scale, which ultimately saves development time and cost. The methods and systems disclosed herein also allow for automation and control of the cell culture process to maximize vector yield and improve reproducibility. Finally, the number of vessels needed to reach production-level scales of viral vectors (e.g., $10^{16}$ to $10^{18}$ AAV VG per batch) can be greatly reduced compared to other cell culture solutions.

Embodiments are not limited to the vessel rotation about a central longitudinal axis. For example, the vessel may rotate about an axis that is not centrally located with respect to the vessel. In addition, the axis of rotation may be a horizontal or vertical axis.

EXAMPLES

To demonstrate the efficacy of the cell culture matrix, cell culture systems, and related methods of this disclosure, studies were conducted on the seeding and culturing of cells, according to the following examples.

Example 1

Figure 13B:
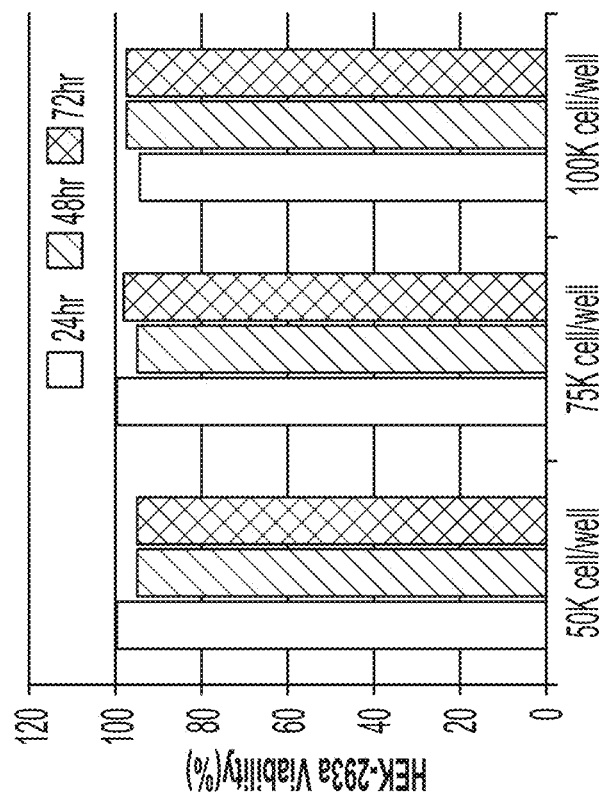
FIG. 13B is a bar graph showing the viability of the cells from FIGS. 12 and 13A.
Figure 13A:
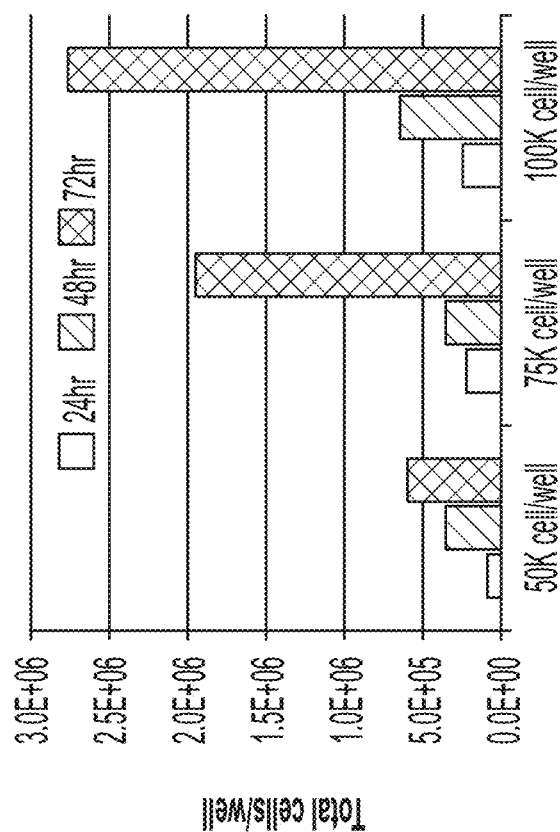
FIG. 13A is a graph showing the cell growth and expansion data of HEK293T cells on the substrates of FIGS. 12A-12C.

In Example 1, a cell culture matrix having a polyethylene terephthalate (PET) woven mesh substrate (see FIG. 12) was tested in static cell culture conditions. The PET mesh was washed in ethanol and plasma treated in oxygen RF plasma. Gelatin was adsorbed on the surface of the mesh filaments to promote cell adhesion. Disc-shaped pieces of the mesh were placed into Corning® ultra-low attachment (ULA) 6-well plates. HEK293T cells were seeded onto the mesh disks at different seeding densities (50K per $cm^2$, 75K per $cm^2$, 100K per $cm^2$) and cell culturing was performed for three days. Cells on the filament surfaces were stained with fluorescent Green Cell tracker dye. FIG. 12 shows the results of this visualization of cells on the filament surfaces. The size of the mesh filaments relative to the size of the cells allows for the monofilament fibers to effectively act as a two-dimensional surface for cell attachment and proliferation. Cell proliferation was measured by harvesting cells from the mesh and counting on a Vi-Cell® cell counter from Beckman Coulter. The results showed good cell attachment and proliferation on the cell culture matrix under static cell culture conditions. For example, FIG. 13A shows the total cells per well for each seeded mesh after 24, 48, and 72 hours. In addition to the number of cells, the viability of the cells is shown in FIG. 13B, which demonstrates very high viability across seeding densities.

Example 2

Figure 14B:
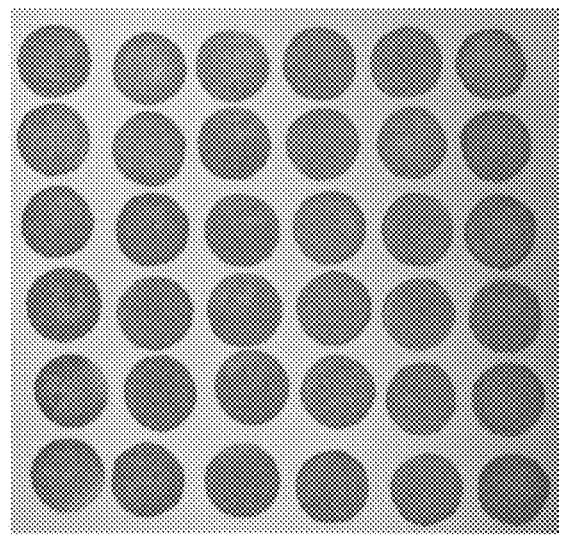
FIG. 14B is a photograph of layers of the cell culture substrate with stained HEK293T cells from a bioreactor seeded by a cell tumbling method.
Figure 14A:
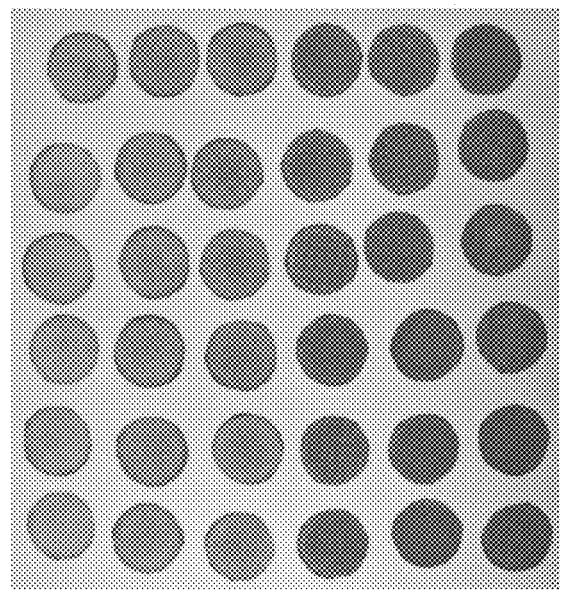
FIG. 14A is a photograph of layers of the cell culture substrate with stained HEK293T cells from a bioreactor seeded in static conditions.

In Example 2, cells were cultured in a packed bed bioreactor system, such as the one shown in FIG. 6, according to an example of an embodiment of this disclosure. The packed bed has a cylindrical shape and is made of a stack of cell culture substrates, each of a circular or disk shape. Specifically, in Example 2, the packed bed had a height of about 25 mm, and included one hundred disks of PET woven mesh substrate, each having a diameter of about 20 mm. The mesh used corresponds to Mesh C in Table 1. It is estimated that the total two-dimensional surface area available for cell attachment was about 760 $cm^2$. To inoculate the bioreactor, 8 ml of an HEK293T cell suspension (2 million cells/ml) was injected directly into packed bed. Media perfusion started immediately after introduction of the cell suspension, with a perfusion flow rate set to 3 ml/min. Perfusion at this flow rate continued for 24 hours and then the flow rate was reduced to 1 ml/min. After this, the perfusion flow rate was adjusted to maintain $pO_2 \geq 50\%$ saturation, and $pH \geq 7$ at the outlet of the bioreactor. After two to three days, cells were stained with crystal violet and the bioreactor was disassembled to verify uniformity of cells attachment within the matrix. FIGS. 14A and 14B show every third disk of the packed bed matrix with attached HEK293T cells stained with a crystal violet stain. FIG. 14A shows the results from a bioreactor seeded in static conditions. Based on the variance in the staining, it was seen that there was non-uniform cell attachment after a 3-day culture. Specifically, there was a higher concentration of cells at the bottom of packed bed (corresponding to disks at the bottom of the image in FIG. 14A) and fewer cells at the top part of the packed bed (corresponding to disks at the top of the image in FIG. 14A). FIG. 14B shows the results from a bioreactor seeded with a seeding method according to a preferred embodiment, in which cells were continuously tumbled inside the packed bed during the initial attachment stage. As a result, uniform cell distribution is observed in all parts of packed bed after two days of cell culture, as evidenced by the consistent staining of cells in the disks from the top to bottom of the reactor (and top to bottom of the image in FIG. 14B). This indicates uniform cell distribution was achieved when the bioreactor was continuously perfused at the cell seeding stage.

Example 3

In Example 3, cells were cultured in a packed bed bioreactor system, and transfection of HEK293 T cells was performed for adeno-associated virus (AAV) production in the bioreactor. The same bioreactor setup as Example 2 was used in Example 3 (see, e.g., FIG. 6). The packed bed contained 100 disks of PET mesh (Mesh C of Table 1). A diameter of each disk was about 20 mm, and the bed height was about 25 mm, with a total of about 760 $cm^2$ of two-dimensional surface area available for cell attachment and proliferation. To inoculate the bioreactor, 8 ml of an HEK293T cell suspension (2 million cells/ml) was injected directly into packed bed. A media storage vessel containing about 50 ml of media was fluidly connected to the bioreactor vessel. For 72 hours, cells were cultured in Dulbecco's Modified Eagle's Medium (DMEM) ATCC® media, with +10% FBS and +6 mM L-Glutamine. Media was replaced with a fresh media supply when the pH of the media in a storage vessel dropped below 7. Perfusion flow rate was adjusted accordingly to maintain pO$_2$≥50% saturation, and pH≥7 at the outlet of the bioreactor. After 72 hours, culture medium was changed with 50 ml of Corning® DMEM (15-018) with +10% FBS, +6 mM L-Glutamine, and transfection reagents were added to a final concentration of 2 ug/ml of AAV2 and PEIpro at a 1:2 ratio. During the next 72 hours, culture medium was changed to a fresh supply if pH in a storage bottle dropped below 7. Perfusion flow rate was adjusted accordingly to maintain pO$_2$≥50% saturation and pH≥7 at the outlet of the bioreactor. Cells were harvested by using 5× TrypLE. Transfection efficiency was analyzed by fluorescent flow cytometer, viral particle and viral genome titer were analyzed by ELISA and PCR assays. Cell culture results are presented in Table 2, where "VP" stands for viral protein, and "GC" stands for genome copies.

TABLE 2

Transfection of HEK 293T cells and AAV production in packed bed bioreactor results.

| Sample No. | Total harvested cell/cm$^2$ (viability %) | Transfection efficiency (%) | VP/cell | VP/cm$^2$ | GC/cell | GC/cm$^2$ |
|---|---|---|---|---|---|---|
| 1 | 188913 (92%) | 90.5 | 2.1e4 | 4.03e9 | 1.6e4 | 3e9 |
| 2 | 331104 (95%) | 88.2 | 2.3e4 | 7.6e9 | 1.5e4 | 4.8e9 |

Example 4

In Example 4, an embodiment of a roller bottle cell culture system was tested. A Corning® roller bottle #430195 was used with a surface area of 490 cm$^2$. To prevent the cells from attaching to the tissue culture treated surface, the roller bottles were treated with a 0.5% solution of BSA for a minimum of 16 hours and washed with water prior to each experiment. Cells were grown on a standard 2D surface (T-Flasks) and harvested using a standard protocol using a Trypsin/EDTA solution to release the cells from the surface and the subsequent deactivation of the Trypsin/EDTA solution by the addition of complete media containing Fetal Bovine Serum (FBS). The cells were then counted using a cell counter and cells were seeded into the roller bottle with and without a cell culture mesh at a concentration of about 5×10$^4$ cells per cm$^2$ in a total volume of 200 mL. As shown in FIGS. 15 and 16, for the roller bottle 500 with a cell culture mesh 502, the mesh was rolled into a tight cylindrical roll 503 so that it could be inserted through the mouth 501 of the bottle and, once inserted into the interior of the bottle, the cell culture mesh partially unwound and expanded (as indicated by arrows 504) toward the wall of the roller bottle. The length of the cell culture mesh was long enough that, after expanding within the roller bottle, a double layer of cell culture mesh was provided around the inner circumference of the roller bottle, as shown in FIGS. 15 and 16. Cells were allowed to attach to the surface at various rotation speeds (0.5 to 4 rpm) in a 37° C. incubator with 5% CO$_2$ and 95% relative humidity for 16+ hours. After cell attachment, the speed was decreased to about 1 rpm for standard growth of the cells in a roller bottle. Measurement of media was done periodically to determine when media exchanges were necessary. Visualization of the cells attached to the mesh surface was done using a crystal violet in solution containing methanol and paraformaldehyde inside the roller bottle. After cell staining, the mesh was removed from the roller bottle and imaged.

Figure 17A:
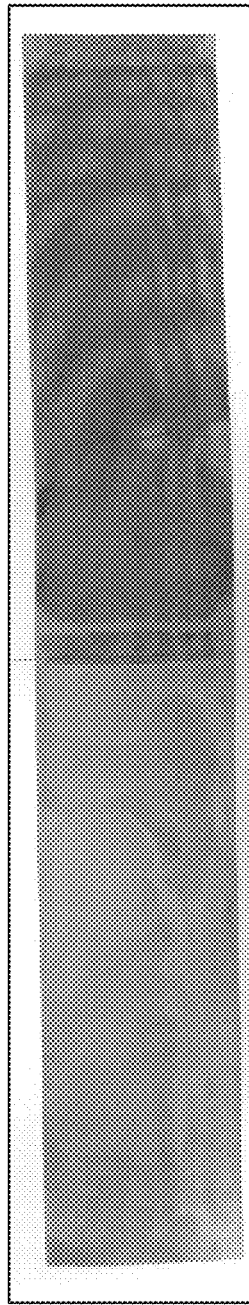
FIG. 17A is a photograph of a cell culture substrate with stained cells following seeding in a roller-bottle style cell culture system using a slow revolution speed during cell seeding, according to one or more embodiments.
Figure 17B:
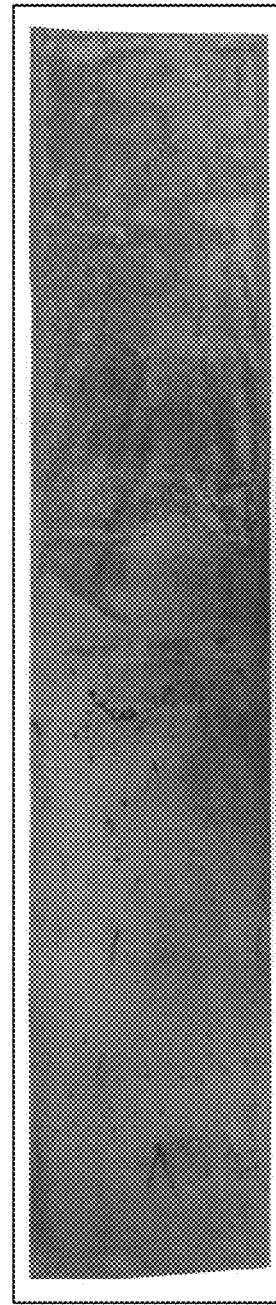
FIG. 17B is a photograph of a cell culture substrate with stained cells following seeding in a roller-bottle style cell culture system using a faster revolution speed during cell seeding, according to one or more embodiments.

FIGS. 17A and 17B show the mesh that was removed from the roller bottles in Example 4, and demonstrate the presence of stained HEK293 cells that adhered to double layered meshes inside the roller bottle. Total available surface area for adherent cells to attach was 2450 cm$^2$ in the roller bottle according to an embodiment of this disclosure, versus 490 cm$^2$ in regular roller bottle without the mesh substrate. In FIG. 17A, the crystal violet stain of cells attached to a PET mesh (corresponding to Mesh C of Table 1) that was self-aligned in a two-layer structure inside the roller bottle. Cells were seeded at 0.5 rpm roller bottle speed. Note that outside layer of the mesh that faces the bottle wall was predominantly seeded with the cells. FIG. 17B shows the crystal violet stain of cells attached to a PET mesh (corresponding to Mesh C of Table 1) that was self-aligned in two-layer structure inside the roller bottle. Cells were seeded at 4 rpm roller bottle speed. Note uniform cells seeding of two mesh layers. As can be seen from FIGS. 17A and 17B, the uniformity of cell seeding depended on rotation speed of the roller bottle during the seeding step. Contrary to the regular roller bottle seeding protocol, fast rotation speed was required to seed cells uniformly on the available adherent surface of the mesh.

The embodiments disclosed herein have advantages over the existing platforms for cell culture and viral vector production. It is noted that the embodiments of this disclosure can be used for the production of a number of types of cells and cell byproducts, including, for example, adherent or semi-adherent cells, Human embryonic kidney (HEK) cells (such as HEK23), including transfected cells, viral vectors, such as Lentivirus (stem cells, CAR-T) and Adeno-associated virus (AAV). These are examples of some common applications for a bioreactor or cell culture substrate as disclosed herein, but are not intended to be limiting on the use or applications of the disclosed embodiments, as a person of ordinary skill in the art would understand the applicability of the embodiments to other uses.

Example 5

Figure 18A:
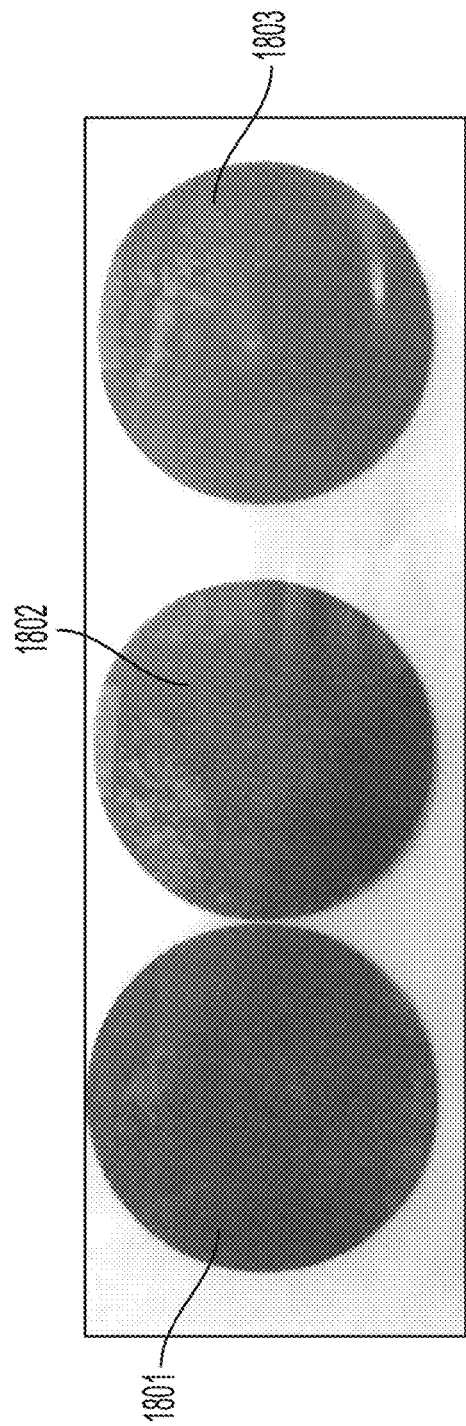
FIG. 18A is a photograph of disks from a cell culture matrix with stained cells after seeding and growth but before cell harvesting, according to one or more embodiments.

As discussed above, one advantage of embodiments of this disclosure is the flow uniformity through the cell culture substrate. Without wishing to be bound by theory, it is believed that the regular or uniform structure of the cell culture substrate provides a consistent and uniform body through which media can flow. In contrast, existing platform predominately rely on irregular or random substrates, such as felt-like or non-woven fibrous materials. The uniform properties of the substrate of this disclosure can be illustrated by examining the uniform and consistent cell seeding that is achieved on the substrate. FIG. 18A, for example, shows three disks (1801, 1802, 1803) of substrate material from Example 5, according to some embodiments of this disclosure. The disks in FIG. 18A are a woven PET mesh material as described herein, and each have a diameter of about 60 mm. The surface area for a bioreactor packed with 10 to 300 layers of similar disks would be about 678 to 20,300 cm$^2$. In this example, cell culture was performed using a stack of 100 disks. The first disk 1801 was the top disk in a stack of such disks within a bioreactor, the second disk 1802 was the middle disk of the stack, and the third disk 1803 was the bottom disk of the stack. Despite being located at different positions within the stack, the staining in FIG. 18A shows remarkably consistent cell attachment.

Figure 18B:
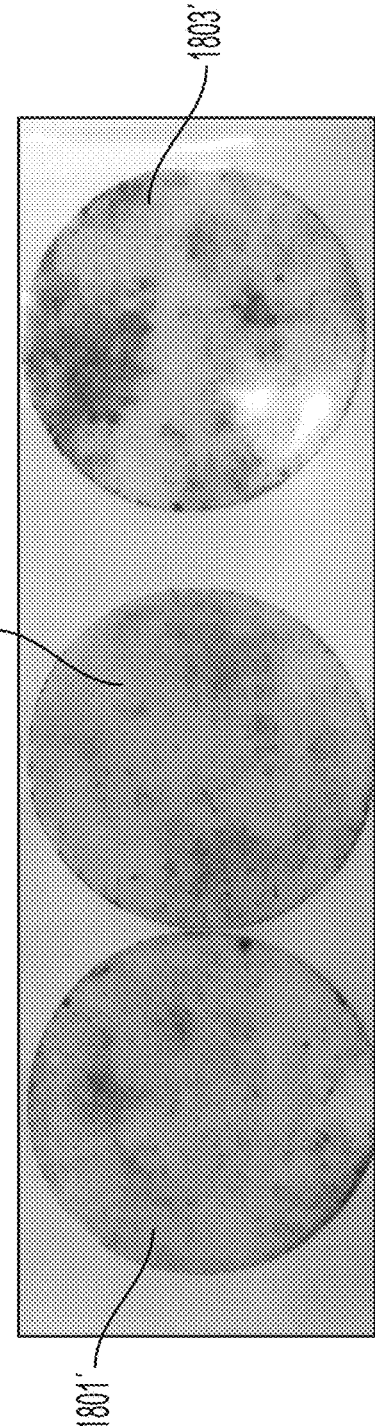
FIG. 18B is a photograph of disks from FIG. 18A after cell harvest, according to one or more embodiments.

In the experiment that produced the images in FIGS. 18A and 18B, the bioreactor was prefilled with cell culture media and system was preconditioned overnight to achieve a steady state of pH 7.2, D.O. 100%, and 37° C. 400 ml of ATCC DMEM media+10% FBS+6 mM L-Glutamine was used to fill the entire bioreactor system. 30 ml of HEK293T cells in suspension (5 million cells/mL) was injected directly into the packed bed though 3-way port to form inoculation. The bioreactor was perfused with preconditioned media at rate of 30 mL/min for the first 48 hours to allow uniform cell distribution, attachment and initial growth in the packed bed. After 48 hours of culture, 200 ml of fresh complete ATCC DMEM media was added into the system to maintain glucose level above 1 g/L. Perfusion flow rate was adjusted automatically to maintain DOexternal≥45% of media saturation at the bioreactor outlet. 72 hours post inoculation, the culture medium was exchanged with 500 ml of Corning DMEM (15-018)+10% FBS+6 mM L-Glutamine and allowed to perfuse for 2 hours. A transfection mix (complexes of plasmid DNA and PEI at 1:2 ratio; 0.8 ug of total DNA/million cells) was added to a final concentration of 2 μg total DNA/ml of medium 24 hours post-transfection, and culture medium was exchanged with 500 ml of fresh complete Corning DMEM (15-018) medium to replenish spent nutrients. The perfusion flow rate was adjusted automatically to maintain $DO_{external} \geq 45\%$ saturation at the outlet of the bioreactor. Glucose level was monitored during subsequent 48 hours of culture and supplemented through media addition or exchange as needed to maintain levels above 0.3 g/L. At 72 hours post-transfection, cells were washed with DPBS and harvested by using 1× Accutase solution. Transfection efficiency was analyzed by fluorescent flow cytometry, and viral particle and viral genome titer were analyzed by ELISA and qPCR assays.

Crystal violet staining was used to highlight the uniform growth of cells over the entire surface of the disks in FIG. 18A. Despite the first disk 1801, second disk 1802, and third disk 1803 being spread throughout the stack of the cell culture matrix, the cell growth is consistent across all three disks. The image in FIG. 18A was taken after a 72-hour culture and before the cells were harvested from the substrate. FIG. 18B shows the same three disks after the cells have been harvested (1801', 1802', and 1803'). As shown by the relative absence of crystal staining in FIG. 18B, the cells have been harvested uniformly across the surface of each disk and across the three disks of the cell culture matrix stack. Based on analysis, more than 95% of cells were recovered from the bioreactor. The cell culture results of the AAV production in these 60 mm diameter substrate stacks/vessels with a total surface area of 6780 cm² are shown below in Table 3, which shows the transfected cell yield, transfection efficiency, and viral genome per cm² yield. Again, the uniform structure of the substrate and the uniform flow characteristics are believed to contribute to this efficient and uniform growth and harvest capability.

TABLE 3

Transfected cell yield, transfection efficiency, and viral genome per cm² yield from 60 mm bioreactor.

|  | Cells/cm² at harvest | % GFP+ cells | Bulk AAV VG/cm² |
| --- | --- | --- | --- |
| Reactor 1 | 432,153 | 94 | 3.19 × 10¹⁰ |
| Reactor 2 | 479,351 | 87 | 2.98 × 10¹⁰ |
| Reactor 3 | 395,062 | 88.5 | TBD |

Table 4 below shows the above results in the context of multiple experiments including bioreactor vessels of different diameters (29 mm and 60 mm). The data shows good scalability between smaller (e.g., 29 mm diameter, 1600 cm² surface area) and larger (e.g., 60 mm diameter, 6780 cm² surface area) vessels and/or packed bed matrices.

TABLE 4

Consistent results across bioreactor size.

| Vessel diameter (SA in cm²) | Cells/cm² at harvest | % GFP+ cells | Bulk AAV VG/cm² |
| --- | --- | --- | --- |
| 29 mm (1600 cm²) | 407,500 | 89.9 | 1.74E+10 |
| 29 mm (1600 cm²) | 373,125 | 93.4 | 3.00E+10 |
| 29 mm (1600 cm²) | 376,250 | 89.3 | 2.16E+10 |
| 60 mm (5425 cm²) | 405,529 | 87.8 | 1.97E+10 |
| 60 mm (6780 cm²) | 357,832 | 92.3 | N/A |
| 60 mm (6780 cm²) | 432,153 | 94 | 3.19E+10 |
|  | 479,351 | 87 | 2.98E+10 |
| 60 mm (6780 cm²) | 395,062 | 88.5 | TBD |

Figure 19A:
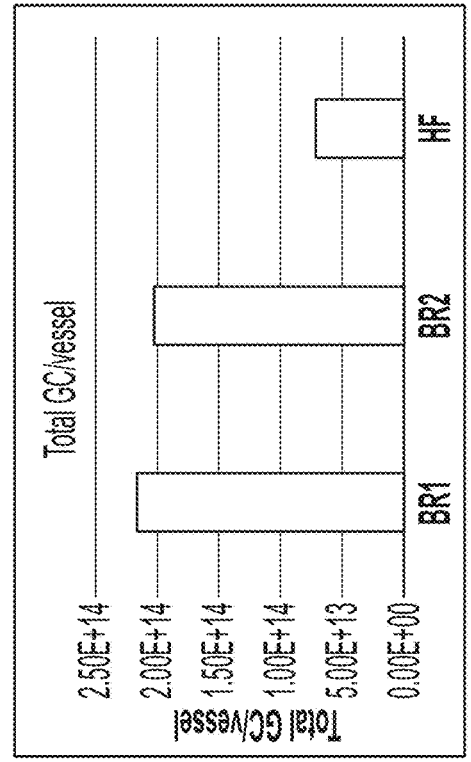
FIG. 19A shows experimental results of total cells harvested for two examples according to embodiments of this disclosure, as compared to a HYPERflask.
Figure 19B:
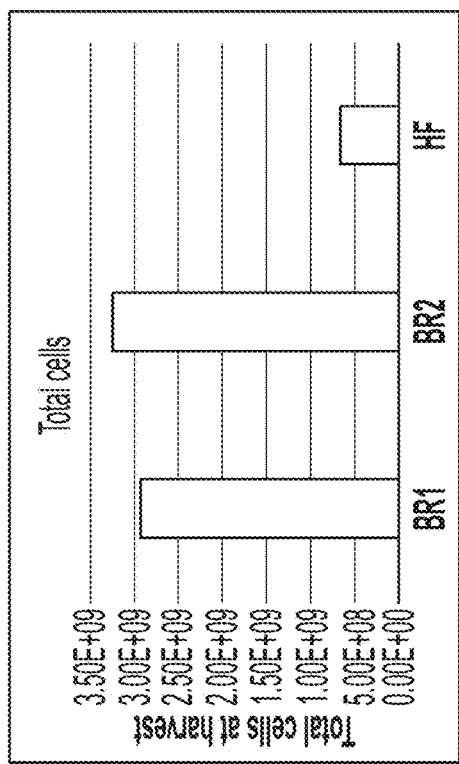
FIG. 19B shows experimental results of total genome copies per vessel for two examples according to embodiments of this disclosure, as compared to a HYPERflask.
Figure 19C:
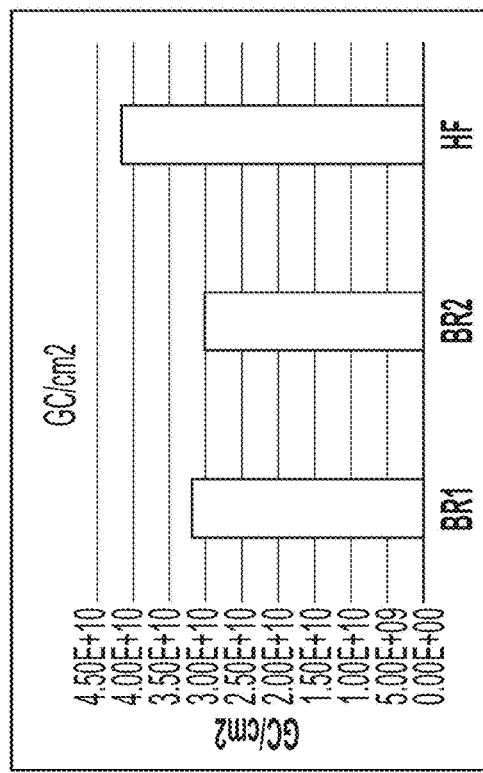
FIG. 19C shows experimental results of genome copies per surface area for two examples according to embodiments of this disclosure, as compared to a HYPERflask.

As discussed above, embodiments of this disclosure can provide a packed bed cell culture matrix and/or bioreactor capable of culturing a high density of cells in a relatively small and practical footprint. For example, the 60 mm cell culture matrix in the examples in Tables 3 and 4 above has a surface area of about 6870 cm². For reference, the Corning HYPERflask® has a surface area of about 1720 cm². The 60-mm diameter cell culture matrix of Tables 3 and 4 can be housed in a bioreactor that is smaller than the HYPERflask, but can nonetheless results in a higher cell count at harvest, higher number of total genome copies (GC, or viral genomes (VG) per vessel. FIG. 19 shows these numbers of two bioreactor vessels with 60-mm diameter substrates from Tables 3 and 4 compared to the HYPERflask, as well as showing the GC per cm², which, though lower than the HYPERflask, makes up for it with a higher surface area.

Example 6

Figure 20B:
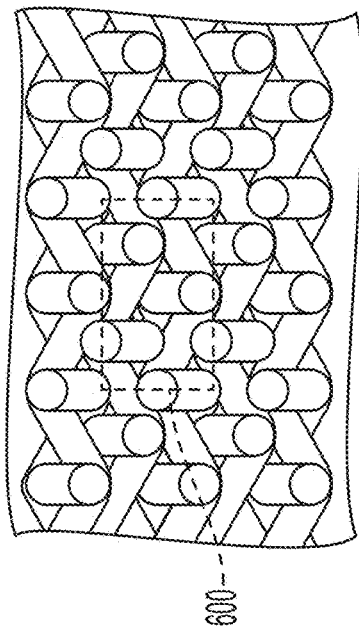
FIG. 20B shows a side cross-section view of the multi-layer woven mesh cell culture substrate of FIG. 20A, according to one or more embodiments of this disclosure.
Figure 21B:
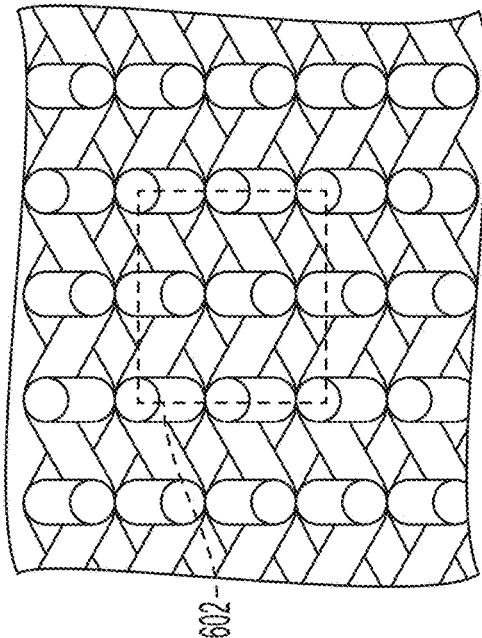
FIG. 21B shows a side cross-section view of the multi-layer woven mesh cell culture substrate of FIG. 21A, according to one or more embodiments of this disclosure.
Figure 20A:
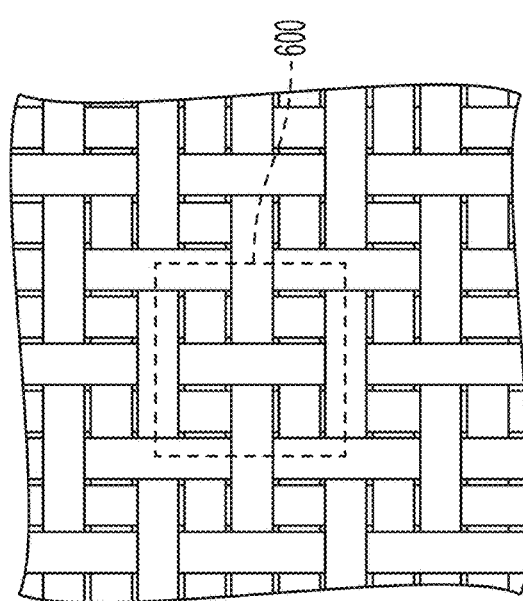
FIG. 20A shows a plan view of a modeled multi-layer woven mesh cell culture substrate in a tightly packed arrangement, according to one or more embodiments of this disclosure.
Figure 21A:
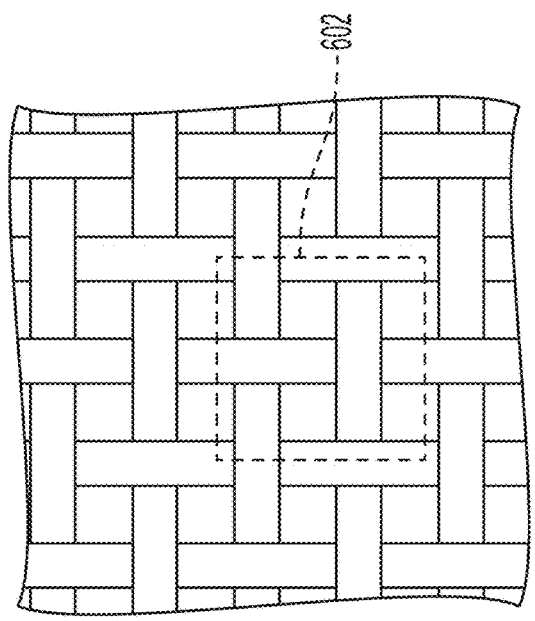
FIG. 21A shows a plan view of a modeled multi-layer woven mesh cell culture substrate in a loosely packed arrangement, according to one or more embodiments of this disclosure.
Figure 22:
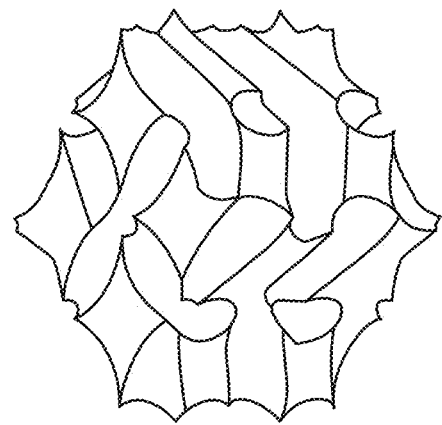
FIG. 22A shows the modeled empty space in the dotted-line volume shown in FIGS. 20A and 20B.
FIG. 22B shows the modeled empty space in the dotted-line volume shown in FIGS. 21A and 21B.
Figure 22:
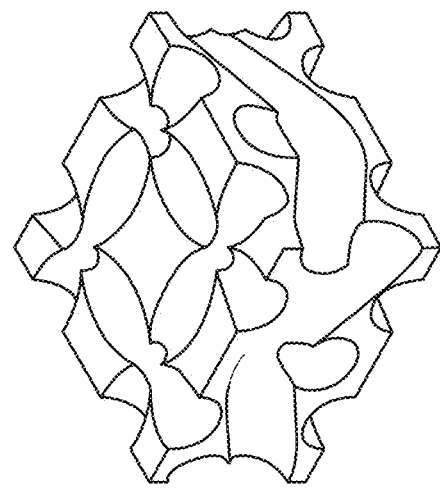
Figure 23C:
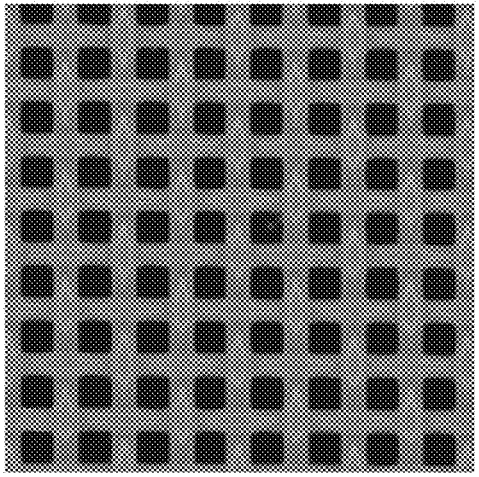
FIG. 23C is a photograph of a mesh sample in accordance with mesh sample C from Table 5, according to one or more embodiments of this disclosure.
Figure 23F:
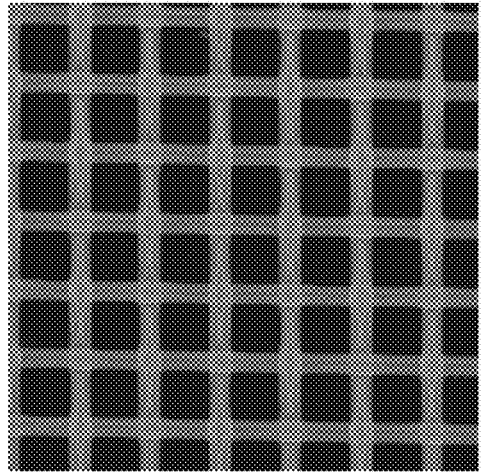
FIG. 23F is a photograph of a mesh sample in accordance with mesh sample F from Table 5, according to one or more embodiments of this disclosure.
Figure 23B:
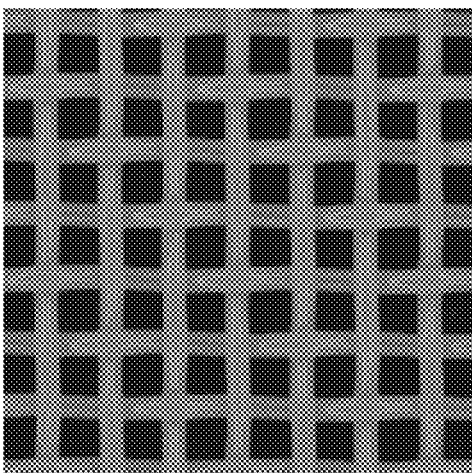
FIG. 23B is a photograph of a mesh sample in accordance with mesh sample B from Table 5, according to one or more embodiments of this disclosure.
Figure 23E:
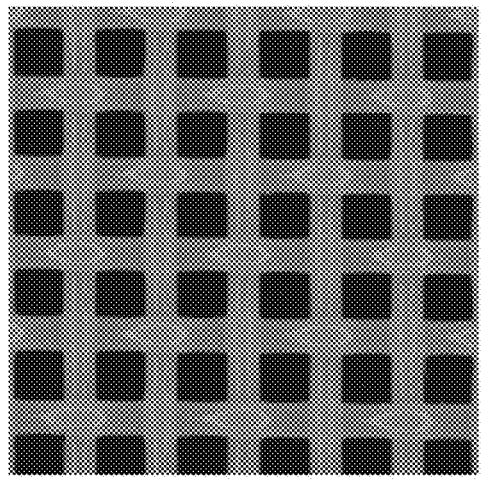
FIG. 23E is a photograph of a mesh sample in accordance with mesh sample E from Table 5, according to one or more embodiments of this disclosure.
Figure 23A:
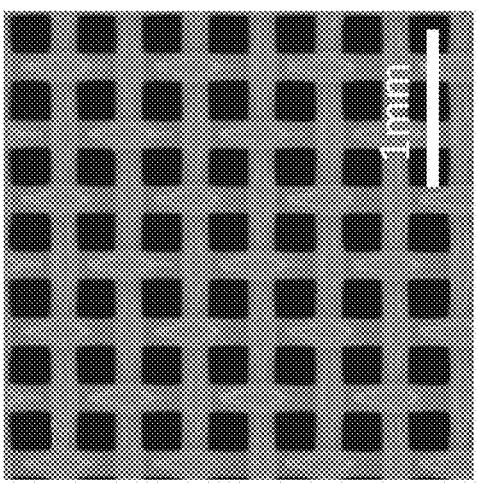
FIG. 23A is a photograph of a mesh sample in accordance with mesh sample A from Table 5, according to one or more embodiments of this disclosure.
Figure 23D:
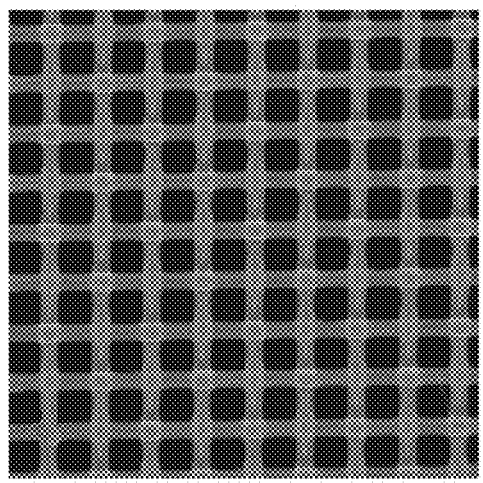
FIG. 23D is a photograph of a mesh sample in accordance with mesh sample D from Table 5, according to one or more embodiments of this disclosure.

To further examine the flow uniformity or permeability of the substrates of this disclosure, modeling was used to understand the porosity of the three-dimensional cell culture matrix. Sheets of woven PET mesh substrate were modeled in a tight-packed configuration and a loose-packed configuration, which represent upper and lower boundaries of the packing density of a substrate stack for the particular mesh sheet that was modeling. In particular, FIG. 20A shows a plan view of the tight-packed configuration, and FIG. 20B shows a cross-section side view of the same stack. FIGS. 21A and 21B show plan and cross-section views, respectively, of the loose-packed configuration. For each modeled configuration, a sample cell 600, 602 was defined that encloses the same volume of mesh material to analyze the porosity per unit volume of the sample cell 600, 602. The modeled volume of open space within each cell is shown in FIGS. 22A (for tight-packed stack) and 22B (for loose-packed stack). The porosity in terms of percentage of open space was about 40.8% for the loose-packed cell, and 61.4% for the tight-packed cell. Because the modeled stacks in FIGS. 20A-21B represent the tightest- and loosest-packed configurations for the given mesh material, the porosities of 40.8% and 61.4% are the upper and lower bounds of porosity for this particular mesh material. Depending on the alignment and real-world packing density when using this mesh material, the porosity may fall in between these extremes. However, embodiments of this disclosure are not limited to this porosity range, as variations in the mesh dimensions and arrangement of the substrate within the cell culture vessel can lead to a different range of porosities.

In addition to the modeled porosity range, porosity was measured using real packed beds of PET woven mesh substrate. The measurements were made using one hundred disks, each with a diameter of 22.4 mm, stacked with random alignment. The total weight of the 100-disk stack was 5.65±0.2 g. Volume of the PET material of the stack was calculated, assuming a PET density of 1.38 g/cm³, using the following formula:

$$V_{PET} = \text{(total weight of stack)} / \text{(density of PET)} \quad \text{Equation 2}$$

Thus, the PET volume $V_{PET}$ of 5.65 g of PET (for 100 disks of 22.4 mm diameter) was calculated to be 4.1 ml. The total volume $V_{total}$ of the stack, including the PET volume $V_{PET}$ and the volume of the open space within the stack, was then calculated using the following formula:

$$V_{total} = \pi \times (0.5 \times \text{disk diameter}) \times \text{(stacked bed height)} \quad \text{Equation 3}$$

The 100-disk stack had a stack height of 25±1 mm. Thus, with a disk diameter of 22.4 mm, $V_{total}$ was found to be 9.85 ml. Accordingly, porosity of the stacked bed can be calculated using the following:

$$\text{Porosity} = (V_{total} - V_{PET})/V_{total} \quad \text{Equation 4}$$

Using Equation 4 and the above values, the porosity was calculated to be 58.4%, which is within the range predicted by the model.

Example 7

Figure 26:
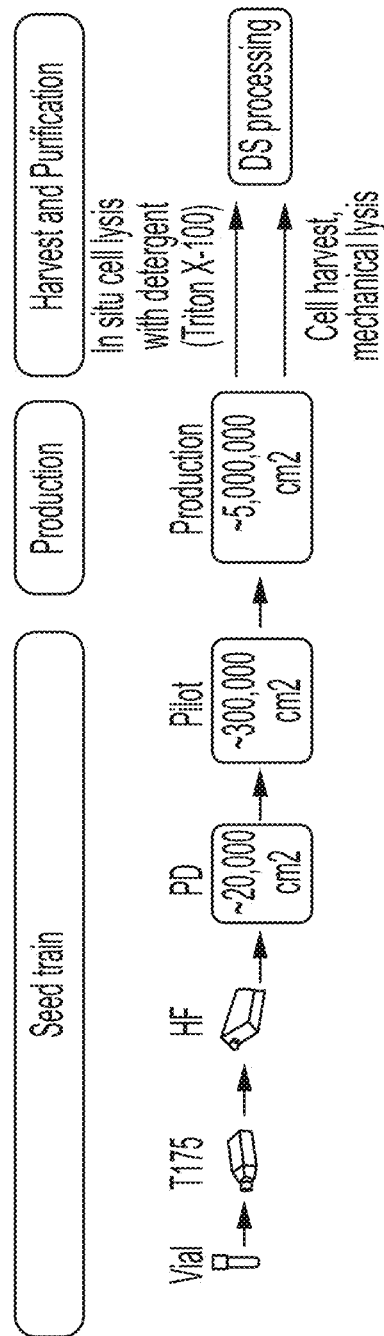
FIG. 26 is a schematic of a seed train process, according to one or more embodiments of this disclosure.

In Example 7, the permeabilities of various PET woven mesh substrate materials were compared. Table 5 shows the PET mesh samples used in this comparison.

actor system technology to be part of a seed train. Instead, cell populations are usually scaled up on various cell culture substrates. This can negatively impact the cell population, as it is believed that cells become acclimated to certain surfaces and being transferred to a different type of surface can lead to inefficiencies. Thus, it would be desirable to minimize such transitions between cell culture substrates or technologies. By using the same cell culture substrate across the seed train, as enabled by embodiments of this disclosure, efficiency of scaling up a cell population is increased. FIG. 26 shows an example of one or more embodiments where the woven cell culture substrate of the present application is used as part of a seed train to allow for a smaller bioreactor to seed a larger bioreactor. Specifically, as shown in FIG. 26, the seed train can begin with a vial of starter cells which are seeded into a first vessel (such as a T175 flask from Corning), then into a second vessel (such as a HyperFlask® from Corning), then into a process-development scale bioreactor system according to embodiments of this invention (effective surface area of substrate of about 20,000 cm²), and then into a larger bioreactor pilot system according to embodiments of this invention (effective surface area of substrate is about 300,000 cm²). At the end of this seed train, the cells can be seeded into a production-scale bioreactor vessel according to embodiments of this disclosure, with a surface area o about 5,000,000 cm², for example. Harvest and purification steps can then be performed when the cell culture is complete. As shown in FIG. 26, harvest can be accomplished via in situ cell lysis with a detergent (such as Triton X-100), or via mechanical lysis; and further downstream processing can be performed, as needed.

TABLE 5

Mesh substrates for permeability comparison.

| Mesh Sample | Weave Pattern | Opening Diameter (μm) | Fiber Diameter (μm) | Open area | Packing Thickness (μm) | Surface Area of 60 mm disc (cm²) | Normalized Surface to Volume ratio |
|---|---|---|---|---|---|---|---|
| A | Plain | 250 | 160 | 37% | 280 | 74.9 | 1.00 |
| B | Twill | 250 | 152 | 39% | 280 | 74.2 | 0.99 |
| C | Plain | 210 | 147 | 35% | 230 | 80.9 | 1.16 |
| D | Plain | 200 | 112 | 41% | 130 | 68.1 | 1.30 |
| E | Plain | 300 | 195 | 37% | 370 | 68.1 | 0.83 |
| F | Plain | 319 | 128 | 51%* | 200 | 53.0 | 0.99 |

Figure 24:
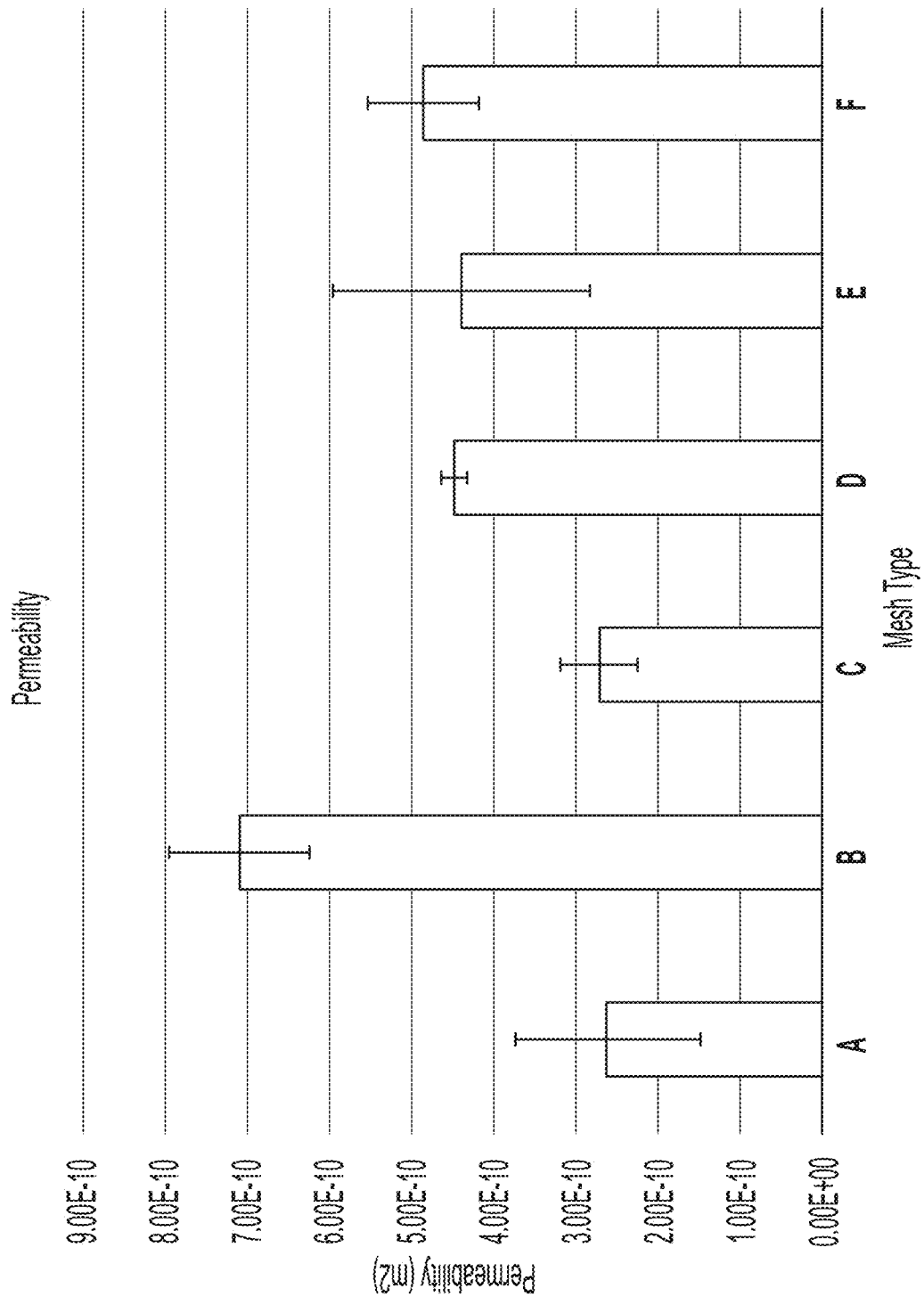
FIG. 24 is a bar graph of the permeability of woven mesh samples A-F from FIG. 23.
Figure 25:
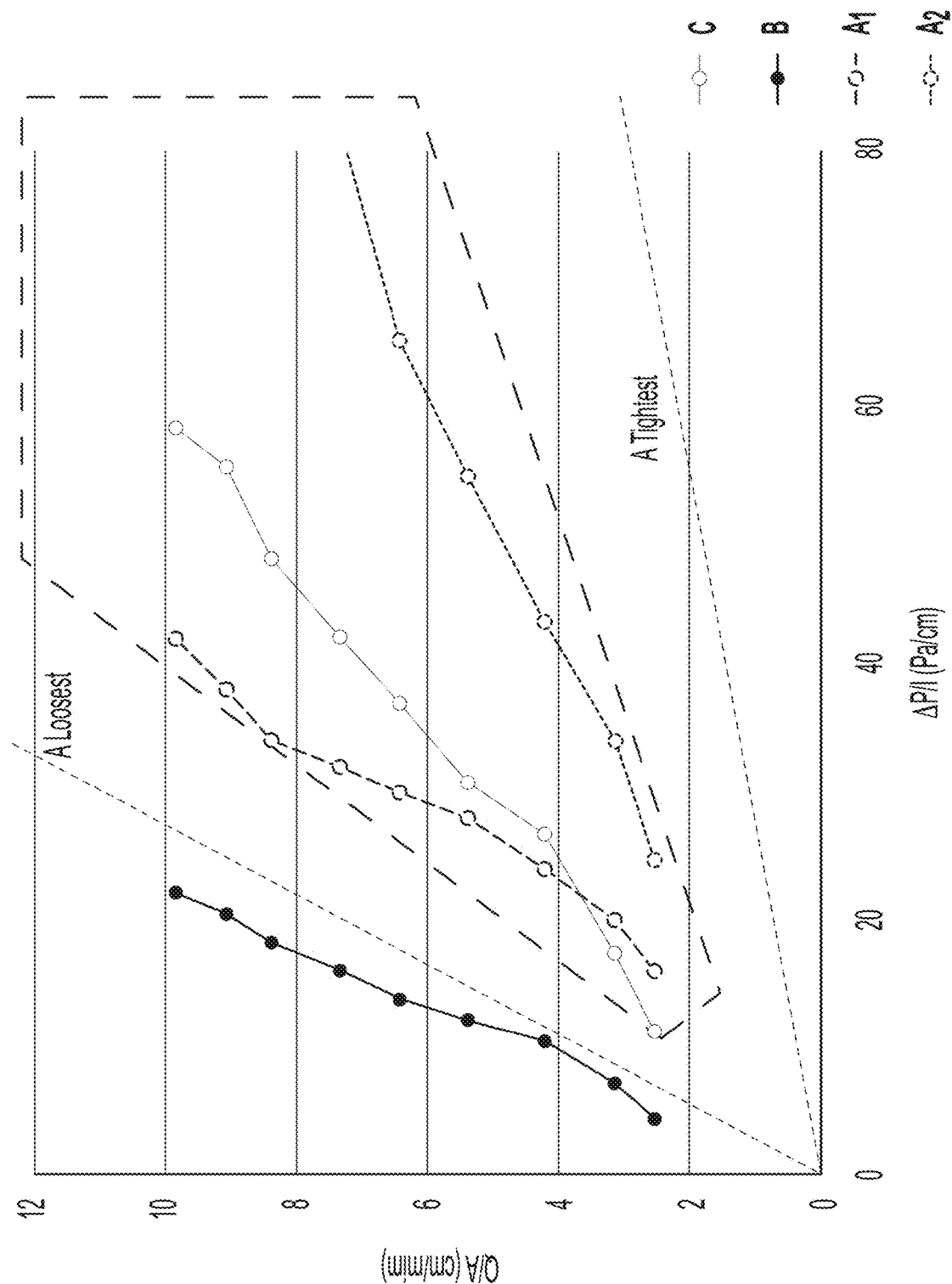
FIG. 25 shows the results of a pressure drop test using samples A-C from FIG. 23.

Photographs of the mesh samples A through F are shown in FIG. 23. The results of the permeability of each mesh sample A-F is shown in FIG. 24. FIG. 25 shows the results of a pressure drop test for samples A-C, where a pressure drop test was conducted for sample A in stacks with different arrangements and packing densities. The dotted lines represent the tightest and loosest packing densities for mesh sample A, with sample $A_1$ being a more loosely packed stack than sample $A_2$. The pressure drop in terms of change in pressure (Pa) per centimeter is plotted against Q/A.

Example 8

As discussed herein, the embodiments of this disclosure provide cell culture substrates, bioreactor systems, and methods of culturing cells or cell by-products that are scalable and can be used to provide a cell seed train to gradually increase a cell population. One problem in existing cell culture solutions is the inability for a given biore- The benefits of using the same cell culture substrate within the seed train (e.g., from process development level to pilot level, or even to production level) include efficiencies gained from the cells being accustomed to the same surface during the seed train and production stages; a reduced number of manual, open manipulations during seed train phases; more efficient use of the packed bed due to uniform cell distribution and fluid flow, as described herein; and the flexibility of using mechanical or chemical lysis during viral vector harvest.

Example 9

To understand the potential increased viral production yield of substrates of the present disclosure, the performance of a PET woven mesh substrate was compared to that the substrate used in the iCellis®. Table 6 summarizes the total viral particles produces using these substrates in a simplified bioreactor.

TABLE 6

Viral particles produced using PET woven mesh substrate material and substrate material from the iCellis.

| Test No. | PET Woven Mesh | iCellis Substrate |
|---|---|---|
| 1 | 6.99E13 | 7.18E12 |
| 2 | 3.65E13 | e |
| 3 | 7.72E13 | 1.01E13 |
| 4 | 4.63E13 | n/a |
| Average | 6.01E13 | 1.01E13 |

From the results in Table 6, it is possible to calculate the volume of substrate material needed to produce a certain number of viral particles. For example, if the goal for production-scale viral vector production is 3.00E+18 viral particles, as shown in Table 7, the volume of PET woven mesh needed is about one-seventh the amount of iCellis substrate needed.

TABLE 7

Comparison of PET woven mesh substrate and iCellis ® substrate

| Substrate | Total VP/reactor | Reactor bed volume | Crude VP needed | ml of substrate needed to produce crude 3E18 VP | M3 of substrate material needed to produce crude 3E18 VP |
|---|---|---|---|---|---|
| PET mesh | 6.01E+13 | 15 | 3.00E+18 | 7.49E+05 | 0.7 |
| iCellis ® | 1.01E+13 | 15 | 3.00E+18 | 4.46E+06 | 4.5 |

Example 10

Figure 27B:
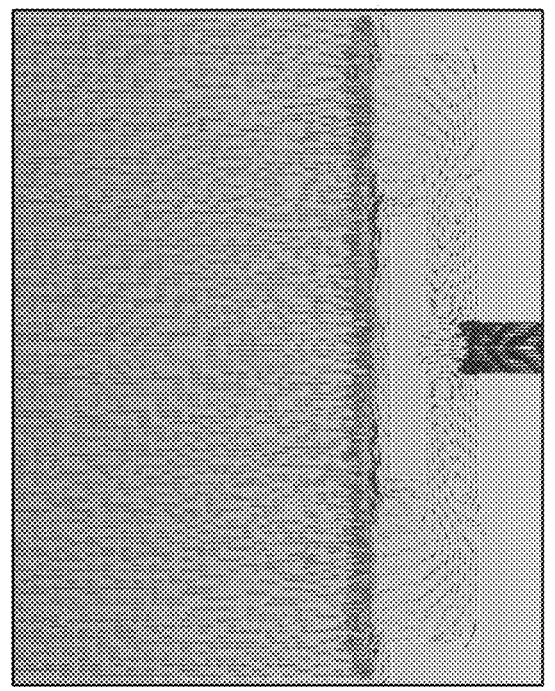
FIG. 27B is a close up view of the flow uniformity model of FIG. 27A.
Figure 27A:
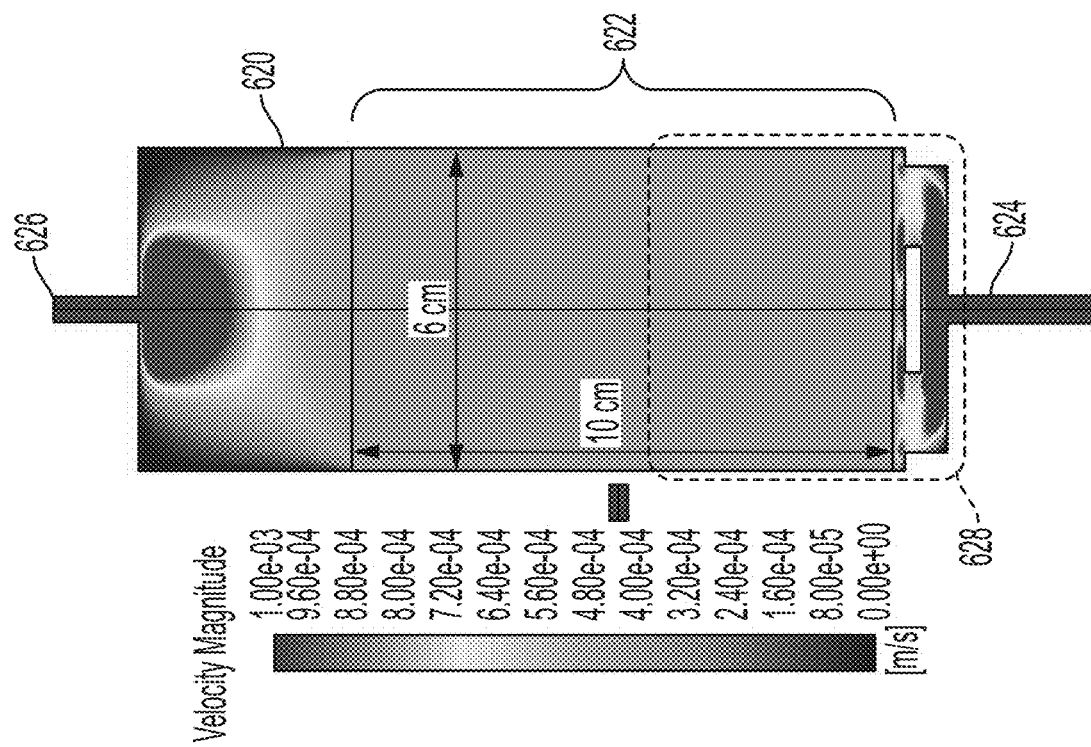
FIG. 27A shows a flow uniformity model of a bioreactor with a woven mesh substrate according to one or more embodiments of this disclosure.

To demonstrate the uniform flow through the open mesh substrates of this disclosure, fluid flow velocity through a packed bed bioreactor was modeled. FIG. 27A shows the modeling results for a vessel 620 having a packed bed region 622 of PET woven mesh disks with diameters of 6 cm, and a bed height of 10 cm and consisting of 357 disks of PET woven mesh substrate. Fluid velocity magnitude is depicted according to the scale shown. While the flow velocity is high near the inlet 624 and outlet 626, the velocity is constant throughout the packed bed region 622, including along the height and across the width of the packed bed. The region denoted by the dotted line 628 is shown in close-up in FIG. 27B, which shows that once the fluid enters the uniform, open structure of the cell culture matrix, velocity is relatively constant. The packed bed in this example equates to a total surface of about 24,214 cm$^2$. Given the uniform flow shown in the model, the percentage of this surface area exposed to non-uniform flow (defined as >2.5% deviation from the mean velocity) was 0%.

To demonstrate the extent to which this uniform flow persists as the vessel is scaled up in size, additional modeling was conducted similar to that of FIG. 27A, but using progressively wider vessels with wider packed beds. The percentage of non-uniform flow for these larger vessel is shown in Table 8. As shown, even when the reactor is scaled up to a diameter of 60 cm, the amount of non-uniform flow remains about one-half of one percent or less of the surface area of the substrate. This shows that the uniform, open woven mesh structure described herein is capable of uniform flow throughout the entirety of the packed bed, unlike existing cell culture substrates.

TABLE 8

Modeled flow uniformity for bioreactors having packed beds of various diameters.

| Packed bed diameter (cm) | Total SA (cm$^2$) | % of SA with non uniform flow* |
|---|---|---|
| 6 (100 disks) | 6,780 | 0.00 |
| 6 (357 disks) | 24,214 | 0.00 |
| 20 | 269,047 | 0.00 |
| 30 | 605,357 | 0.17 |
| 40 | 1,076,190 | 0.52 |
| 60 | 2,421,428 | 0.45 |

Example 11

To better understand the difference in permeability between the woven mesh substrate of the present disclosure and the non-woven, irregular substrates on the existing market, experiments were conducted to measure the permeability of these materials. In particular, a PET woven mesh was compared to the non-woven substrate material used in the iCellis® and to a similar non-woven, disordered substrate that was commercially available. Permeability measurements were made for flow perpendicular to the woven mesh substrate layers of a packed bed of stacked disks, and through a randomly packed bed of non-woven substrate, as well as through a fixed sheet of non-woven substrate material. The non-woven mesh had a fiber diameter of about 20 µm, a thickness of about 0.18 mm, and a porosity o 91%. The woven mesh substrate had a diameter of about 160 µm and an opening diameter of 250 µm.

To mesh permeability, water was used for the test to simulate cell culture medium. The flow rate was controlled to be between 15-50 ml/cm$^2$/min using a priestaltic pump to simulate flow conditions that substrates typically experience in a bioreactor. Due to low pressure drop the samples experienced under the test condition, a monometer was used to measure the pressure difference across the samples. Because of the different substrate types and packing methods, the substrates where held in slightly difference ways.

To measure flow across the non-woven mesh, the sample was cut into 12 mm diameter discs and 10 level of the mesh was held between two open cylindrical chambers sealed by an O-ring. Monometers were connected directly to the open chamber to measure the pressure drop.

To measure flow through randomly packed non-woven mesh, the mesh was cut into 5 mm×25 mm strips and packed into a 29 mm diameter cylindrical chamber. A total of 3 g of mesh strips were packed into 30 ml and for about 45 mm in bed height. At each side of the packed strips, two discs of open woven mesh was used to confine packed bed. There was about 3 mm thick open space at each size of the bed then two pieces of porous materials with thickness of 10 mm were used to redistribute the flow at inlet and outlet.

To measure flow through open woven mesh, the mesh was cut 29 mm discs to fit into the cylindrical chamber. A total of 170 discs were packed layer-by-layer into a 45 mm bed height. The orientation of fibers in each level of mesh was not aligned to each other. The flow was across the mesh discs (i.e., perpendicular to the disk surfaces). There was about a 3 mm thick open space at each size of the bed then two pieces of porous materials with thickness of 10 mm were used to redistribute the flow at inlet and outlet.

The permeability was calculated using Equation (5):

$$Q = -\frac{KA}{\mu}\frac{dP}{dL} \quad \text{Equation (5)}$$

Where: Q=flow rate; K=permeability; A=across area of the sample or packed bed; dP=pressure drop across the test sample or packed bed; µ=water viscosity; and dL=total sample thickness or packed bed height.

Figure 28:
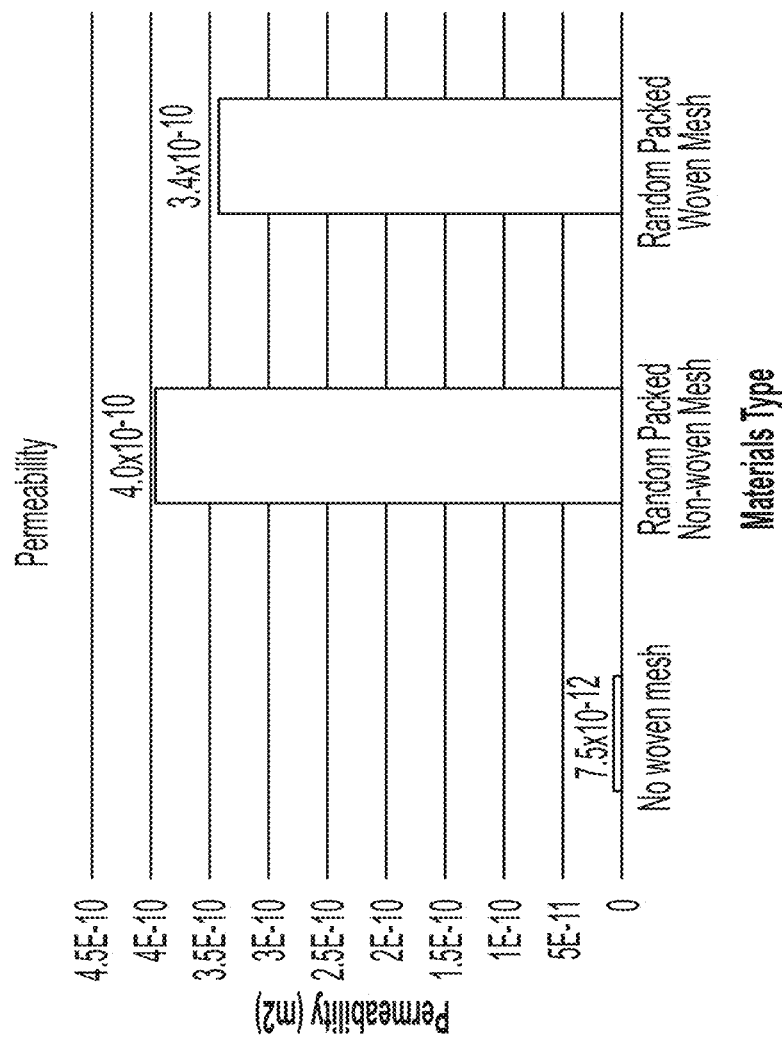
FIG. 28 is a bar graph of the permeability measurements of woven and non-woven cell culture substrates.

The final calculated permeabilities are summarized in FIG. 28. The results show that non-woven mesh had much lower permeability was of about $7.5 \times 10^{-12}$ m², which was about 1/50 of the permeability across the open woven mesh. When the non-woven mesh was cut into small strips and packed randomly, their permeability increased enormously and became similar as open woven mesh. This increased permeability is believed to be the result of the flow mostly bypassing around the mesh strips due to the channeling effect discussed above.

Figures 29A, 29B:
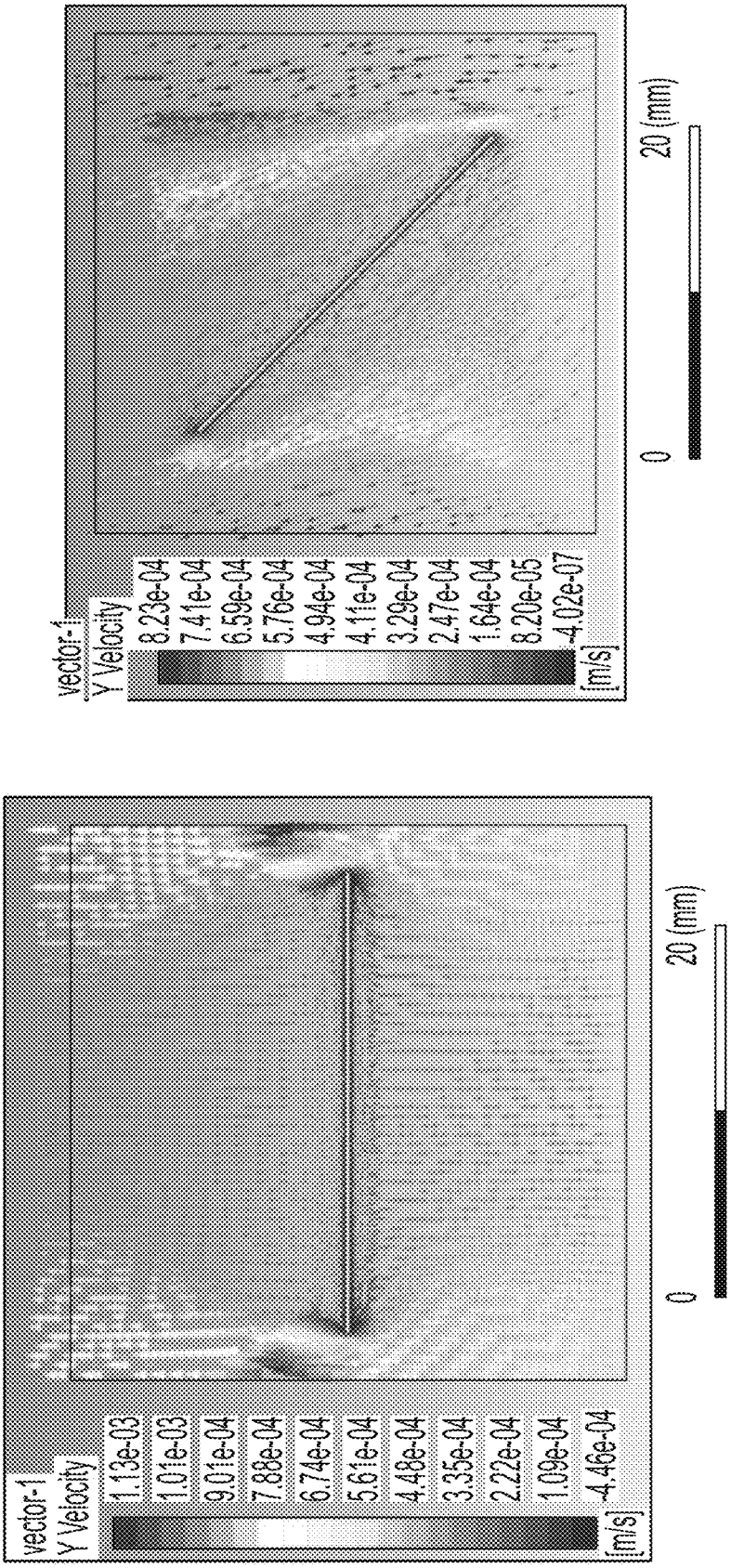
FIG. 29A shows simulated flow velocities around a non-woven mesh substrate piece aligned 90° with respect to the flow direction.
FIG. 29B shows simulated flow velocities around a non-woven mesh substrate piece aligned 45° with respect to the flow direction.

Based on the measured permeabilities, the flow was simulated through and around the non-woven mesh and the open woven mesh. The simulation was done using ANSYS Fluent v19.2 software package. For illustration purpose, two scenarios were studied: with the surface of the substrate material surface aligned (i) 90° and (ii) 45° with respect to the flow direction, as shown in FIGS. 29A and 29B. In both cases, the flow was mostly around the mesh and only about 0.02-0.005% of the flow went through the mesh, when the spacing between neighboring mesh on the same level is 5 mm. This will create a significant dead zone behind the mesh and cause the non-uniform flow through the packed bed. The non-uniformity becomes more severe when the non-woven mesh piece is not perfectly aligned normal to the flow direction.

Figure 30A:
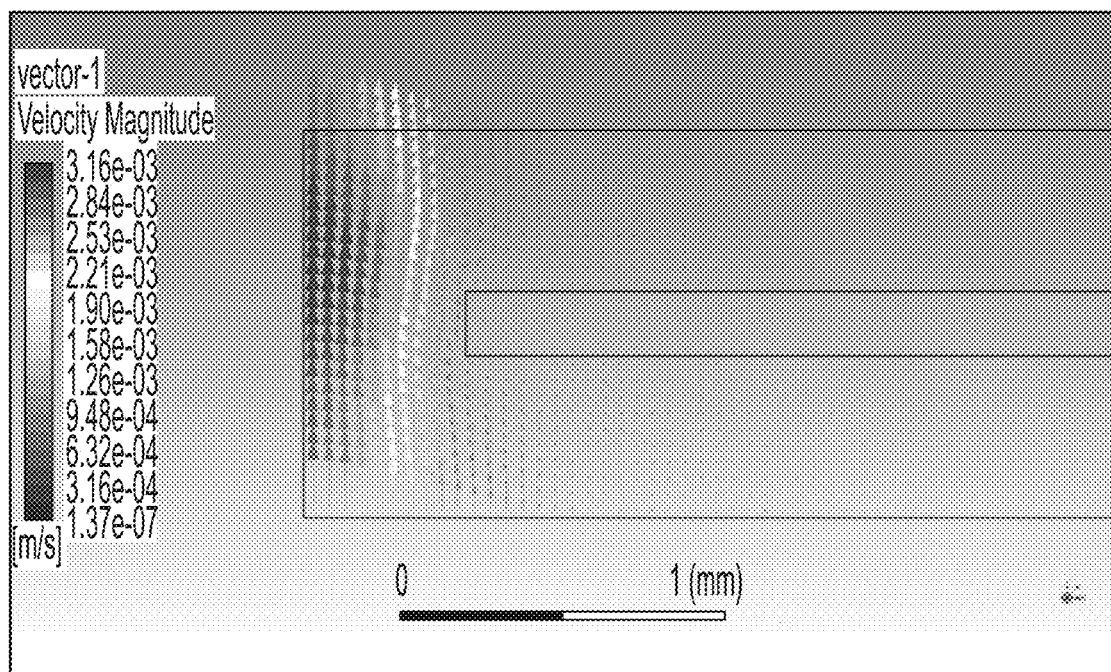
FIG. 30A shows simulated flow velocities around a non-woven mesh substrate piece with 1 mm gap between all neighbors.
Figure 30B:
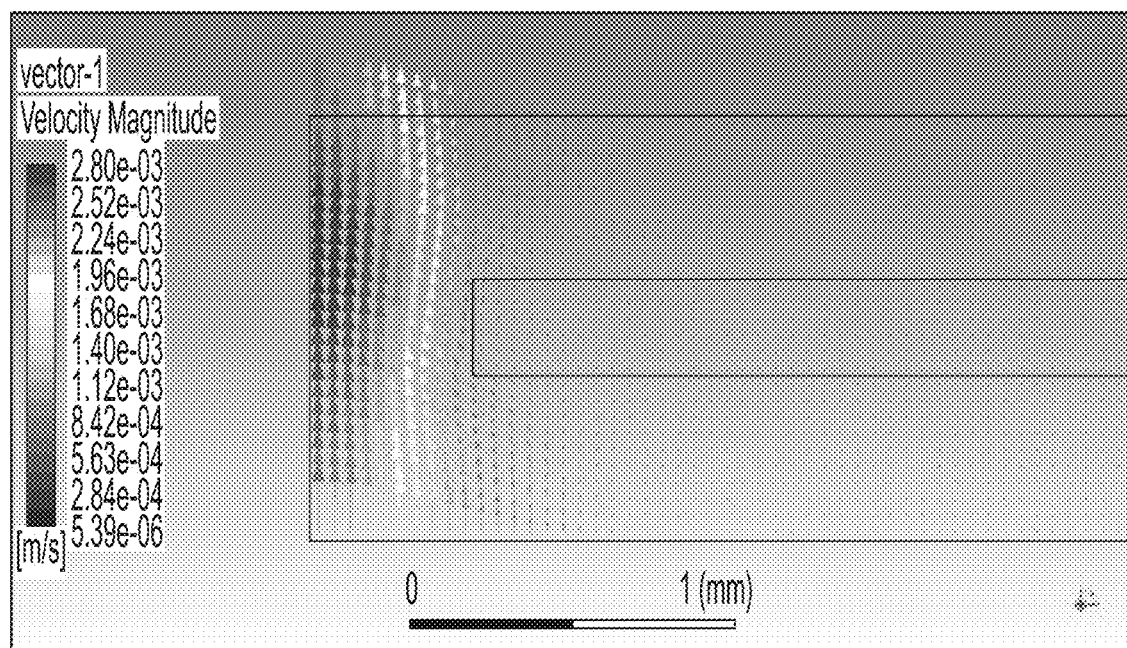
FIG. 30B shows simulated flow velocities around an open woven mesh with 1 mm gap between all neighbors.
Figure 31:
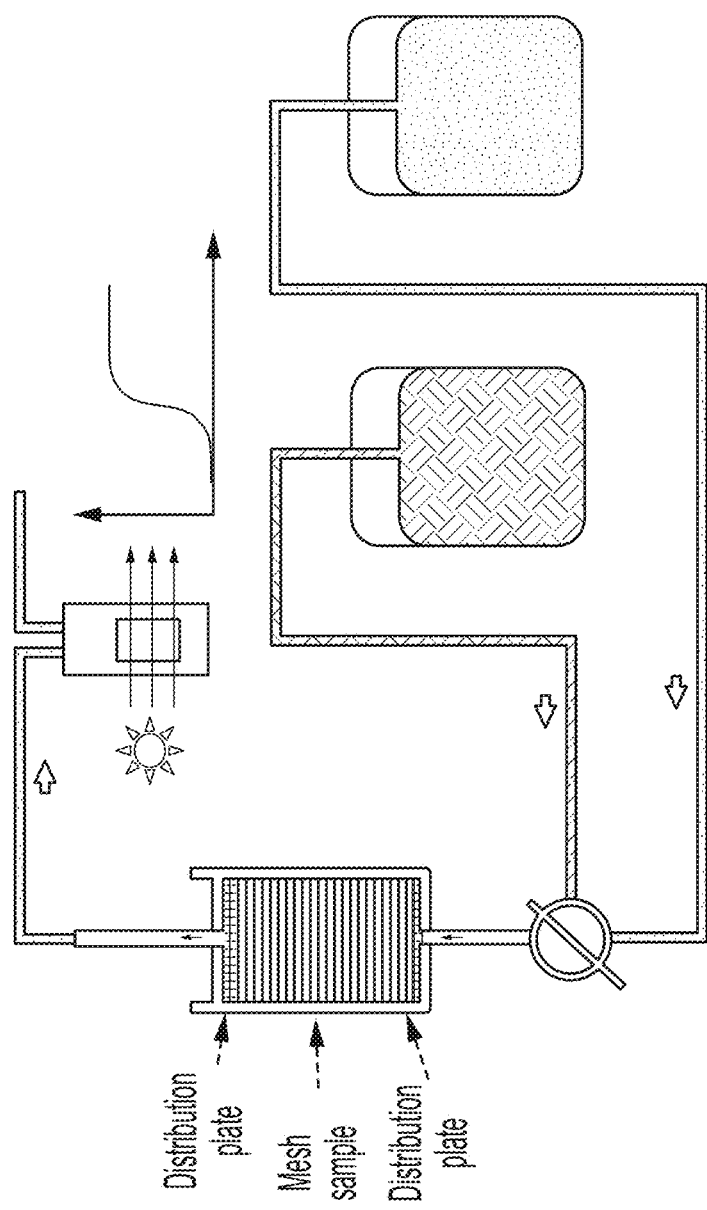
FIG. 31 is a schematic drawing of an experimental setup for measuring residence time distribution of different cell culture substrate samples.

In the case of open woven mesh, the open structure made allowed flow easily through the mesh and did not create a dead zone behind the open mesh layer. It is believed that the regular structure of the woven mesh also contributed to the uniform flow distribution through the each level. This, in turn, enables more uniform flow in through the entire packed bed. The comparison is clearly shown in FIGS. 30A (non-woven mesh piece) and 30B (open woven mesh substrate), which show a close-up view of flow near the edge of the substrate materials. In the case of FIGS. 30A and 30B, the gap between neighboring mesh pieces in all six directions is shortened to 1 mm, and only the periodic domain of one such mesh piece is simulated. FIG. 3 OA shows that with non-woven mesh has very low permeability, as the flow is mostly bypassing around the substrate, and there is very little flow through the substrate itself. Only 0.17% of the total mass flow goes through the non-woven mesh. In contrast, open woven mesh has a much higher permeability, so that there is more flow through it as shown in FIG. 30B. The shortcut flow through the gap becomes weaker when comparing the colorbars in the two cases. For the open woven mesh, there is as high as 10.7% of the total mass flow rate going through the substrate, which demonstrates that open woven mesh has superior permeability even if it is packed with gaps.

As discussed herein, it is possible for multiple woven mesh disks to be randomly packed with countless variations in alignment between the disks. However, the range of possible alignments can be reduced to two theoretical limits based the packing density (i.e. the tightest and the loosest packing). These two ideal or boundary conditions allow for simplifying a large packed bed to a small periodic domain. Using this model, it was found that permeability through the substrate differs by roughly 10 times from the tightest to the loosest packing limit. The experimentally measured permeability data from above lies well within this range, which served as a good validation point. The model also showed that permeability in the flow direction is similar to that in the traverse direction, in both packing conditions. This suggests that the woven mesh of this disclosure will less likely change the flow direction as we found in non-woven substrates and make the flow more uniform, regardless of substrate orientation. The improved flow uniformity of substrates of this disclosure was further demonstrated by the residence time distribution (RTD) measurements in the following example.

Example 12

Figure 32:
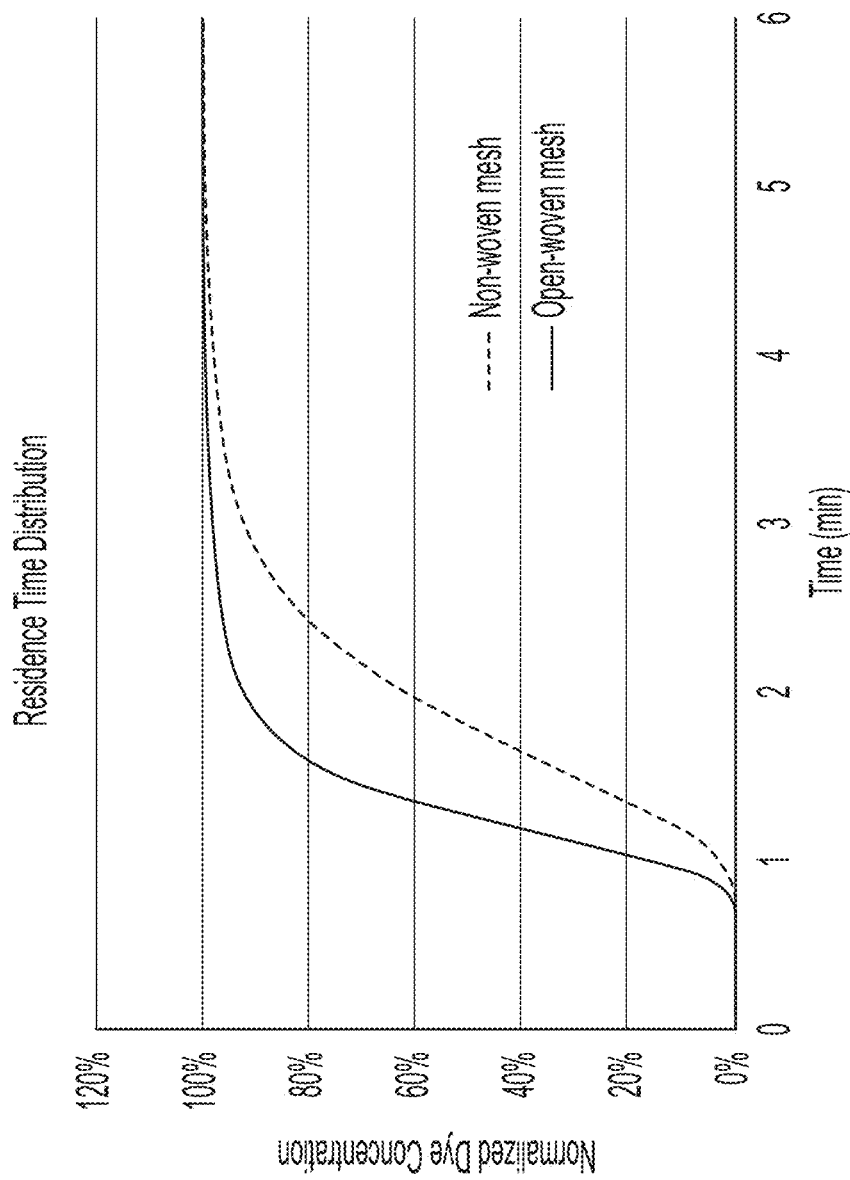
FIG. 32 is a graph showing the change in dye concentration vs. time during residence time distribution measurement for a woven and non-woven cell culture substrate.

Residence time distribution (RTD) is a useful tool to study the flow in a vessel. Its theory, measurement, and analysis can be found in the textbook: Levenspiel, O. Chemical Reaction Engineering. 3ed. 1999. Wiley. New York. FIG. 5. is the schematic drawing of the setup to measure RTD. The chamber is cylindrical shape with diameter of 29 mm and total 36 ml packed bed volume with 3.6 g of non-woven mesh or 200 layers of open woven mesh was filled into the vessel chamber. 1:2000 diluted McCormick Green Food Color was used as a tracer for the measurement. A UV-vis with a Flowcell was used to monitor the change of tracer concentration. A flow rate of 22.5 ml/ml was used for all experiment. The chamber was first filled with water. After switched to green dye, the change of the OD was recorded. The results are shown in FIG. 32.

The following equations were used to calculate mean residence time t (Equation (6)) and variance σ (Equation (7)):

$$\bar{t} = \int_0^\infty (1-F)dt \quad \text{Equation (6)}$$

$$\sigma^2 = 2\int_0^\infty t(1-F)dt - \bar{t}^2 \quad \text{Equation (7)}$$

where F is normalized concentration in a step tracer response. Table 9 summarizes the calculated mean residence time and variance from the measurement. The open woven mesh shows shorter mean residence time, which was likely caused by the lower porosity and decreased dead zones. In a packed bed of open woven mesh, the porosity was about 60% while the porosity of the non-woven mesh has higher porosity which was about 93%. The much higher normalized variance detected in packed bed of non-woven mesh suggests that the flow in non-woven mesh was less uniform or ideal.

TABLE 9

Means residence time and variance of non-woven
and open woven mesh from measurement.

|  | Woven mesh | Non-woven mesh |
| --- | --- | --- |
| Mean residence time (min) | 1.37 | 1.97 |
| Variance (min$^2$) | 0.21 | 0.84 |
| Normalized variance | 0.11 | 0.22 |

From the above permeability and residence time experiments, it is shown that the type of non-woven, irregular cell culture substrate used in current bioreactors has lower permeability than the substrate of the present disclosure. These non-woven substrates also have different permeability or flow rates depending on the direction of flow relative to the non-woven substrate, whereas the substrates of the present disclosure exhibits essentially isotropic flow behavior. Due to the non-uniform flow and lower residence time of the non-woven substrates, nutrients and transfection reagents can take longer to reach to the cells on the substrate surface or the other side of a substrate layer, as compared to the uniform, woven mesh substrate of the present disclosure. Adding to this is the higher permeability of the randomly packed non-woven substrate, which suggest a strong channeling effect and thus non-uniform delivery of cells or nutrients.

Illustrative Implementations

The following is a description of various aspects of implementations of the disclosed subject matter. Each aspect may include one or more of the various features, characteristics, or advantages of the disclosed subject matter. The implementations are intended to illustrate a few aspects of the disclosed subject matter and should not be considered a comprehensive or exhaustive description of all possible implementations.

Aspect 1 is direct to a cell culture matrix comprising: a substrate comprising a first side, a second side opposite the first side, a thickness separating the first side and the second side, and a plurality of openings formed in the substrate and passing through the thickness of the substrate, wherein the plurality of openings is configured to allow flow of at least one of cell culture media, cells, or cell products through the thickness of the substrate.

Aspect 2 is directed to the cell culture matrix of Aspect 1, wherein the substrate comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 3 is directed to the cell culture matrix of Aspect 1 or Aspect 2, wherein the substrate comprises at least one of a molded polymer lattice sheet, a 3D-printed lattice sheet, and a woven mesh sheet.

Aspect 4 is directed to the cell culture matrix of Aspect 3, wherein the substrate comprises the woven mesh comprising one or more fibers.

Aspect 5 is directed to the cell culture matrix of Aspect 4, wherein the one or more fibers comprise a cross-section shape that is at least one of flat, round, rectangular, or polygonal.

Aspect 6 is directed to the cell culture matrix of Aspect 4 or Aspect 5, wherein the one or more fibers comprises at least one of a monofilament fiber and a multifilament fiber.

Aspect 7 is directed to the cell culture matrix of any one of Aspects 4-6, wherein the one or more fibers comprises a first fiber with a first fiber diameter from about 50 µm to about 1000 µm, from about 50 µm to about 600 µm, from about 50 µm to about 400 µm, from about 100 µm to about 325 µm, or from about 150 µm to about 275 µm.

Aspect 8 is directed to the cell culture matrix of Aspect 7, wherein the one or more fibers further comprises a second fiber with a second fiber diameter from about 50 µm to about 1000 µm, from about 50 µm to about 600 µm, from about 50 µm to about 400 µm, from about 100 µm to about 325 µm, or from about 150 µm to about 275 µm.

Aspect 9 is directed to the cell culture matrix of Aspect 8, wherein the second fiber diameter is different than the first fiber diameter.

Aspect 10 is directed to the cell culture matrix of any one of Aspects 1-9, wherein the plurality of openings comprises an opening diameter of from about 100 µm to about 1000 µm, from about 200 µm to about 900 µm, or from about 225 µm to about 800 µm.

Aspect 11 is directed to the cell culture matrix of Aspect 10, wherein the fiber diameter is from about 250 µm to about 300 µm, and the opening diameter is from about 750 µm to about 800 µm, or wherein the fiber diameter is from about 270 µm to about 276 µm, and the opening diameter is from about 785 µm to about 795 µm.

Aspect 12 is directed to the cell culture matrix of Aspect 10, wherein the fiber diameter is from about 200 µm to about 230 µm, and the opening diameter is from about 500 µm to about 550 µm, or wherein the fiber diameter is from about 215 µm to about 225 µm, and the opening diameter is from about 515 µm to about 530 µm.

Aspect 13 is directed to the cell culture matrix of Aspect 10, wherein the fiber diameter is from about 125 µm to about 175 µm, and the opening diameter is from about 225 µm to about 275 µm, or wherein the fiber diameter is from about 150 µm to about 165 µm, and the opening diameter is from about 235 µm to about 255 µm.

Aspect 14 is directed to the cell culture matrix of any one of Aspects 10-13, wherein a ratio of the opening diameter to the fiber diameter is from about 1.0 to about 3.5, from about 1.25 to about 3.25, from about 1.4 to about 3.0, from about 1.5 to about 2.9, from about 1.5 to about 2.4, or from about 2.4 to about 2.9.

Aspect 15 is directed to the cell culture matrix of any one of Aspects 1-14, wherein the plurality of openings comprises openings with a shape that is square, rectangular, rhombus, rhomboid, circular, or oval.

Aspect 16 is directed to the cell culture matrix of any one of Aspects 1-15, wherein the plurality of openings is arrayed in a regular pattern.

Aspect 17 is directed to the cell culture matrix of any one Aspects 1-16, wherein the cell culture matrix comprises a monolayer substrate.

Aspect 18 is directed to the cell culture matrix of any one of Aspects 1-17, wherein the cell culture matrix comprises a multilayer substrate comprising at least a first substrate layer and a second substrate layer, wherein the first substrate layer comprises a first side and a second side opposite to the first side, and the second substrate layer comprises a third side and a fourth side opposite to the third side, the second side facing the third side.

Aspect 19 is directed to the cell culture matrix of Aspect 18, wherein the multilayer substrate is configured so that the first substrate layer has a predetermined alignment with respect to the second substrate layer.

Aspect 20 is directed to the cell culture matrix of 19, wherein the multilayer substrate is configured so that an intersection of fibers on the first substrate layer faces an opening in the second substrate layer.

Aspect 21 is directed to the cell culture matrix of Aspect 19 or Aspect 20, wherein openings in the first substrate layer are at least partially overlapping with the openings in the second substrate layer.

Aspect 22 is directed to the cell culture matrix of Aspect 21, wherein the openings in the first and second substrate layers are aligned.

Aspect 23 is directed to the cell culture matrix of Aspect 28, wherein the multilayer substrate is configured so that the first substrate layer has a random alignment with respect to the second substrate layer.

Aspect 24 is directed to the cell culture matrix of any one of Aspects 1-23, wherein the cell culture matrix comprises a plurality of substrates, each of the plurality of substrates in a random orientation with respect to others of the plurality of substrates.

Aspect 25 is directed to the cell culture matrix of any one of Aspects 1-23, wherein the cell culture matrix comprises a plurality of substrates in a stacked arrangement.

Aspect 26 is directed to the cell culture matrix of Aspect 25, wherein the first and second sides of one of the plurality of substrates is substantially parallel to the first and second sides of other substrates in the stacked arrangement.

Aspect 27 is directed to the cell culture matrix of any one of Aspects 1-23, wherein the substrate is in a cylindrical roll configuration.

Aspect 28 is directed to the cell culture matrix of Aspect 27, wherein the cylindrical roll is configured to expand to a shape of a culture chamber within the bioreactor vessel via a partial unraveling of the cylindrical roll when disposed within the culture chamber.

Aspect 29 is directed to the cell culture matrix of Aspect 28, wherein the cylindrical roll is configured to be inserted into the culture space while the cylindrical role is in a contracted state and to expand within the culture space when disposed within the culture space.

Aspect 30 is directed to the cell culture matrix of any one of Aspects 1-29, wherein the cell culture matrix comprises a plurality of substrates that comprises woven meshes of differing geometries, wherein the differing geometries are different in at least one of fiber diameter, opening diameter, or opening geometry.

Aspect 31 is directed to the cell culture matrix of Aspect 30, wherein the woven meshes of differing geometries are ordered in a predetermined arrangement based on desired flow characteristics within the bioreactor vessel.

Aspect 32 is directed to the cell culture matrix of Aspect 31, wherein the desired flow characteristics comprise at least one of uniform perfusion of liquid media across the cell culture matrix, and distribution of cell growth across the cell culture matrix.

Aspect 33 is directed to the cell culture matrix of 31 or Aspect 32, wherein the woven meshes of differing geometries comprises a first mesh with a first geometry and a second mesh with a second geometry, and wherein the predetermined arrangement comprises the first mesh being upstream of the second mesh with respect to a desired bulk flow direction of cell culture media through the cell culture matrix.

Aspect 34 is directed to the cell culture matrix of Aspect 33, wherein the predetermined arrangement comprises a stack of the first mesh disposed upstream of a stack of the second mesh.

Aspect 35 is directed to the cell culture matrix of Aspect 33 or Aspect 34, wherein the predetermined arrangement comprises stacks of the first mesh and stacks of the second mesh in an alternating arrangement along the bulk flow direction.

Aspect 36 is directed to the cell culture matrix of any one of Aspects 1-35, wherein the cell culture matrix is configured for culturing and/or harvesting at least one of cells, proteins, antibodies, viruses, viral vectors, virus-like particles (VLPs), microvesicles, exosomes, and polysaccharides.

Aspect 37 is directed to the cell culture matrix of any one of Aspects 1-36, wherein the substrate comprises a functionalized surface, the functionalized surface being physically or chemically modified for improved adhesion of the adherent cells to the polymer mesh material.

Aspect 38 is directed to the cell culture matrix of any one of Aspects 1-37, wherein the cell culture matrix comprises a surface configured for adsorption or absorption of components in the culture media onto the surface of the mesh.

Aspect 39 is directed to the cell culture matrix of any one of Aspects 1-38, wherein the cell culture matrix comprises a coating on a surface of the polymer mesh material, the coating being configured to promote adherence of the adherent cells.

Aspect 40 is directed to the cell culture matrix of Aspect 39, wherein the cells adhere to the coating.

Aspect 41 is directed to the cell culture matrix of Aspect 39 or Aspect 40, wherein the coating is a biological or synthetic bioactive molecule configured to promote cell attachment to the cell culture matrix.

Aspect 42 is directed to the cell culture matrix of any one of Aspects 39-41, wherein the coating is at least one of a hydrogel, collagen, Matrigel®, a bioactive molecule or peptide, and a biological protein.

Aspect 43 is directed to the cell culture matrix of any one of Aspects 39-42, wherein the functionalized surface is plasma treated.

Aspect 44 is directed to the cell culture matrix of any one of Aspects 1-43, wherein the cells comprise at least one of adherent cells, suspension cells, and loosely adherent cells that adhere to the woven mesh.

Aspect 45 is directed to a bioreactor system comprising: a cell culture vessel comprising at least one reservoir; and a cell culture matrix disposed in the at least one reservoir, the cell culture matrix comprising a woven substrate having a plurality of interwoven fibers with surfaces configured for adhering cells thereto.

Aspect 46 is directed to the system of Aspect 45, wherein the woven substrate comprises a uniform arrangement of the plurality of interwoven fibers.

Aspect 47 is directed to the system of Aspect 45 or Aspect 46, wherein the woven substrate comprises a plurality of openings disposed between the plurality of fibers.

Aspect 48 is directed to the system of any one of Aspects 45-47, wherein the plurality of fibers comprises polymer fibers.

Aspect 49 is directed to the system of Aspect 48, wherein the polymer fibers comprise at least one of polystyrene, polyethylene terephthalate, polycarbonate, polyvinylpyrrolidone, polybutadiene, polyvinylchloride, polyethylene oxide, polypyrroles, and polypropylene oxide.

Aspect 50 is directed to the system of any one of Aspects 45-49, wherein the cell culture matrix comprises a plurality of woven substrates.

Aspect 51 is directed to the system of Aspect 50, wherein each substrate of the plurality of substrates comprises a first side, a second side opposite the first side, a thickness separating the first and second sides, wherein the plurality of openings pass through the thickness of the substrate.

Aspect 52 is directed to the system of Aspect 50 or Aspect 51, wherein the substrates of the plurality of substrates are arranged adjacent to each other such that one of the first and second side of a substrate is adjacent to other of the first or second side of an adjacent substrate.

Aspect 53 is directed to the system of any one of Aspects 50-52, wherein at least a portion of the plurality of substrates are not separated by a spacer material or barrier.

Aspect 54 is directed to the system of any one of Aspects 50-53, wherein at least a portion of the plurality of substrates are in physical contact with each other.

Aspect 55 is directed to the system of any one of Aspects 45-54, wherein the cell culture vessel comprises at least one port configured for supplying material to or removing material from the at least one reservoir through the at least one port.

Aspect 56 is directed to the system of Aspect 55, wherein the at least one port comprises at least one inlet for supplying material to the at least one reservoir, and at least one outlet for removing material from the at least one reservoir.

Aspect 57 is directed to the system of Aspect 56, wherein the material comprises at least one of media, cells, or cell products.

Aspect 58 is directed to a cell culture system comprising: a bioreactor vessel; and a cell culture matrix disposed in the bioreactor vessel and configured to culture cells; wherein the cell culture matrix comprises a substrate comprising a first side, a second side opposite the first side, a thickness separating the first and second sides, and a plurality of openings formed in the substrate and passing through the thickness of the substrate, and wherein the plurality of openings is configured to allow flow of at least one of cell culture media, cells, or cell products through the thickness of the substrate.

Aspect 59 is directed to the cell culture system of Aspect 58, wherein the substrate comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 60 is directed to the cell culture system of Aspect 58 or Aspect 59, wherein the substrate comprises at least one of a molded polymer lattice sheet, a 3D-printed lattice sheet, and a woven mesh sheet.

Aspect 61 is directed to the cell culture system of Aspect 60, wherein the substrate comprises the woven mesh comprising one or more fibers.

Aspect 62 is directed to the cell culture system of Aspect 61, wherein the one or more fibers comprise a cross-section shape that is at least one of flat, round, rectangular, or polygonal.

Aspect 63 is directed to the cell culture system of Aspect 62 or Aspect 62, wherein the one or more fibers comprises at least one of a monofilament fiber and a multifilament fiber.

Aspect 64 is directed to the cell culture system of any one of Aspects 61-63, wherein the one or more fibers comprises a first fiber with a first fiber diameter from about 50 µm to about 1000 µm, from about 50 µm to about 600 µm, from about 50 µm to about 400 µm, from about 100 µm to about 325 µm, or from about 150 µm to about 275 µm.

Aspect 65 is directed to the cell culture system of Aspect 64, wherein the one or more fiber further comprises a second fiber with a second fiber diameter from about 50 µm to about 1000 µm, from about 50 µm to about 600 µm, from about 50 µm to about 400 µm, from about 100 µm to about 325 µm, or from about 150 µm to about 275 µm.

Aspect 66 is directed to the cell culture system of Aspect 65, wherein the second fiber diameter is different than the first fiber diameter.

Aspect 67 is directed to the cell culture system of any one of Aspects 58-64, wherein the plurality of openings comprises an opening diameter of from about 100 µm to about 1000 µm, from about 200 µm to about 900 µm, or from about 225 µm to about 800 µm.

Aspect 68 is directed to the cell culture system of Aspect 67, wherein the fiber diameter is from about 250 µm to about 300 µm, and the opening diameter is from about 750 µm to about 800 µm, or wherein the fiber diameter is from about 270 µm to about 276 µm, and the opening diameter is from about 785 µm to about 795 µm.

Aspect 69 is directed to the cell culture system of Aspect 67, wherein the fiber diameter is from about 200 µm to about 230 µm, and the opening diameter is from about 500 µm to about 550 µm, or wherein the fiber diameter is from about 215 µm to about 225 µm, and the opening diameter is from about 515 µm to about 530 µm.

Aspect 70 is directed to the cell culture system of Aspect 67, wherein the fiber diameter is from about 125 µm to about 175 µm, and the opening diameter is from about 225 µm to about 275 µm, or wherein the fiber diameter is from about 150 µm to about 165 µm, and the opening diameter is from about 235 µm to about 255 µm.

Aspect 71 is directed to the cell culture system of any one of Aspects 67-70, wherein a ratio of the opening diameter to the fiber diameter is from about 1.0 to about 3.5, from about 1.25 to about 3.25, from about 1.4 to about 3.0, from about 1.5 to about 2.9, from about 1.5 to about 2.4, or from about 2.4 to about 2.9.

Aspect 72 is directed to the cell culture system of any one of Aspects 58-71, wherein the plurality of openings comprises openings with a shape that is square, rectangular, rhombus, rhomboid, circular, or oval.

Aspect 73 is directed to the cell culture system of any one of Aspects 58-72, wherein the plurality of openings is arrayed in a regular pattern.

Aspect 74 is directed to the cell culture system of any one Aspects 58-73, wherein the cell culture matrix comprises a monolayer substrate.

Aspect 75 is directed to the cell culture system of any one of Aspects 58-74, wherein the cell culture matrix comprises a multilayer substrate, the multilayer substrate comprising at least a first substrate layer and a second substrate layer, wherein the first substrate layer comprises a first side and a second side opposite to the first side, and the second substrate layer comprises a third side and a fourth side opposite to the third side, the second side facing the third side.

Aspect 76 is directed to the cell culture system of Aspect 75, wherein the multilayer substrate is configured so that the first substrate layer has a predetermined alignment with respect to the second substrate layer.

Aspect 77 is directed to the cell culture system of 76, wherein the multilayer substrate is configured so that an intersection of fibers on the first substrate layer faces an opening in the second substrate layer.

Aspect 78 is directed to the cell culture system of Aspect 76 or Aspect 77, wherein openings in the first substrate layer are at least partially overlapping with the openings in the second substrate layer.

Aspect 79 is directed to the cell culture system of Aspect 78, wherein the openings in the first and second substrate layers are aligned.

Aspect 80 is directed to the cell culture system of Aspect 75, wherein the multilayer substrate is configured so that the first substrate layer has a random alignment with respect to the second substrate layer.

Aspect 81 is directed to the cell culture system of any one of Aspects 58-80, wherein the cell culture matrix is disposed in the bioreactor vessel such that a bulk flow direction of media through the bioreactor vessel is parallel or perpendicular to the first and second sides.

Aspect 82 is directed to the cell culture system of any one of Aspects 58-81, wherein the cell culture matrix comprises a plurality of substrates randomly packed into the bioreactor vessel.

Aspect 83 is directed to the cell culture system of any one of Aspects 58-82, wherein the bioreactor vessel is a packed bed bioreactor.

Aspect 84 is directed to the cell culture system of any one of Aspects 58-83, wherein the bioreactor vessel comprises: a culture space disposed within the bioreactor vessel and containing the cell culture matrix, one or more openings configured to provide fluid to or remove fluid from the culture space.

Aspect 85 is directed to the cell culture system of Aspect 84, wherein the one or more openings comprise an inlet configured to provide fluid to an interior of the culture space, and an outlet configured to allow fluid to be removed from the culture space of the bioreactor vessel.

Aspect 86 is directed to the cell culture system of Aspect 85, wherein the bioreactor vessel comprises a first end comprising the inlet, a second end opposite the first end and comprising the outlet, the culture space being disposed between the first end and the second end.

Aspect 87 is directed to the cell culture system of Aspect 86, wherein the cell culture matrix has a shape corresponding to a shape of the culture space.

Aspect 88 is directed to the cell culture system of any one of Aspects 58-87, wherein the cell culture matrix comprises the polymer mesh material in a cylindrical roll configuration.

Aspect 89 is directed to the cell culture system of Aspect 88, wherein a central longitudinal axis of the cylindrical roll is parallel to a flow direction of the media.

Aspect 90 is directed to the cell culture system of Aspect 88 or Aspect 89, wherein the cylindrical roll is configured to expand to a shape of the culture space in the bioreactor vessel via an unraveling of the cylindrical roll.

Aspect 91 is directed to the cell culture system of any one of Aspects 88-90, wherein the cylindrical roll is configured to be inserted into the culture space while the cylindrical role is in a contracted state and to expand within the culture space when disposed within the culture space.

Aspect 92 is directed to the cell culture system of any one of Aspects 88-91, wherein the cylindrical roll and the culture space are configured such that frictional forces between the polymer mesh material and a wall of the culture space hold the polymer mesh material in place within the culture space.

Aspect 93 is directed to the cell culture system of Aspect 91, wherein the cylindrical roll is configured to be inserted into the culture space through an opening in the bioreactor vessel.

Aspect 94 is directed to the cell culture system of Aspect 93, wherein the opening is one of the inlet and the outlet of the bioreactor vessel.

Aspect 95 is directed to the cell culture system of any one of Aspects 88-94, wherein the bioreactor vessel comprises a substrate support within the culture space, the substrate support being configured to guide, align, or secure the cell culture matrix within the culture space.

Aspect 96 is directed to the cell culture system of Aspect 95, wherein the substrate support comprises a support member extending from one of the first or second end towards the other of the first or second end, wherein the cylindrical roll is configured to surround the support member such that the support member is parallel to the central longitudinal axis of the cylindrical roll.

Aspect 97 is directed to the cell culture system of any one of Aspects 58-96, wherein the bioreactor vessel is configured to rotate about a central longitudinal axis of the bioreactor vessel during cell culture.

Aspect 98 is directed to the cell culture system of Aspect 97, wherein the central longitudinal axis is perpendicular to the direction of gravity during cell culture.

Aspect 99 is directed to the cell culture system of Aspect 97 or Aspect 98, wherein the cell culture system is configured such that the substrate is moved through the cell culture fluid during the rotation of the bioreactor vessel.

Aspect 100 is directed to the cell culture system of any one of Aspects 97-99, wherein the cell culture system further comprises a rotation means operably coupled to the bioreactor vessel and configured to rotate the bioreactor vessel about the central longitudinal axis.

Aspect 101 is directed to the cell culture system of anyone of Aspects 58-100, wherein the cell culture matrix comprises a plurality of substrates that comprises woven meshes of differing geometries, wherein the differing geometries are different in at least one of fiber diameter, opening diameter, or opening geometry.

Aspect 102 is directed to the cell culture system of Aspect 101, wherein the woven meshes of differing geometries are disposed in the bioreactor vessel in a predetermined arrangement based on desired flow characteristics within the bioreactor vessel.

Aspect 103 is directed to the cell culture system of Aspect 102, wherein the desired flow characteristics comprise at least one of uniform perfusion of liquid media across the cell culture matrix, and distribution of cell growth across the cell culture matrix.

Aspect 104 is directed to the cell culture system of 102 or Aspect 103, wherein the woven meshes of differing geometries comprises a first mesh with a first geometry and a second mesh with a second geometry, and wherein the predetermined arrangement comprises the first mesh being upstream of the second mesh with respect to the bulk flow direction.

Aspect 105 is directed to the cell culture system of Aspect 104, wherein the predetermined arrangement comprises a stack of the first mesh disposed upstream of a stack of the second mesh.

Aspect 106 is directed to the cell culture system of Aspect 104 or Aspect 105, wherein the predetermined arrangement comprises stacks of the first mesh and stacks of the second mesh in an alternating arrangement along the bulk flow direction.

Aspect 107 is directed to the cell culture system of anyone of Aspects 58-106, further comprising means for harvesting the adherent cells or cell byproducts.

Aspect 108 is directed to the cell culture system of Aspect 107, wherein the cell byproducts comprise at least one of proteins, antibodies, viruses, viral vectors, virus-like particles (VLPs), microvesicles, exosomes, and polysaccharides.

Aspect 109 is directed to the cell culture system of any one of Aspects 58-108, wherein the substrate comprises a functionalized surface, the functionalized surface being physically or chemically modified for improved adhesion of the adherent cells to the polymer mesh material.

Aspect 110 is directed to the cell culture system of any one of Aspects 58-109, wherein the cell culture matrix comprises a surface configured for adsorption or absorption of components in the culture media onto the surface of the mesh.

Aspect 111 is directed to the cell culture system of any one of Aspects 58-110, wherein the cell culture matrix comprises a coating on a surface of the polymer mesh material, the coating being configured to promote adherence of the adherent cells.

Aspect 112 is directed to the cell culture system of Aspect 111, wherein the cells adhere to the coating.

Aspect 113 is directed to the cell culture system of Aspect 111 or Aspect 112, wherein the coating is a biological or synthetic bioactive molecule configured to promote cell attachment to the cell culture matrix.

Aspect 114 is directed to the cell culture system of any one of Aspects 111-113, wherein the coating is at least one of a hydrogel, collagen, Matrigel®, a bioactive molecule or peptide, and a biological protein.

Aspect 115 is directed to the cell culture system of any one of Aspects 110-113, wherein the functionalized surface is plasma treated.

Aspect 116 is directed to the cell culture system of any one of Aspects 58-115, wherein the cells comprise at least one of adherent cells, suspension cells, and loosely adherent cells that adhere to the woven mesh.

Aspect 117 is directed to the cell culture system of any one of Aspects 58-116, further comprising a media conditioning vessel configured to supply media to the inlet of the bioreactor vessel.

Aspect 118 is directed to a bioreactor system comprising: a cell culture vessel comprising a first end, a second end, and at least one reservoir between the first and second ends; and a cell culture matrix disposed in the at least one reservoir, the cell culture matrix comprising a plurality of woven substrates each comprising a plurality of interwoven fibers with surfaces configured for adhering cells thereto, wherein the bioreactor system is configured to flow material through the at least one reservoir in a flow direction from the first end to the second end, wherein the substrates of the plurality of woven substrates are stacked such that each woven substrate is substantially parallel to each of the other woven substrates and is substantially perpendicular to the flow direction.

Aspect 119 is directed to the system of Aspect 118, wherein each of the substrates comprises a first side, a second side opposite the first side, a thickness separating the first and second sides, and a plurality of openings pass through the thickness of the substrate.

Aspect 120 is directed to the system of Aspect 118 or Aspect 119, wherein the substrate comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 121 is directed to the system of any one of Aspects 118-120, wherein the plurality of interwoven fibers comprises a first fiber with a first fiber diameter from about 50 µm to about 1000 µm, from about 50 µm to about 600 µm, from about 50 µm to about 400 µm, from about 100 µm to about 325 µm, or from about 150 µm to about 275 µm.

Aspect 122 is directed to the system of Aspect 121, wherein the plurality of interwoven fibers further comprises a second fiber with a second fiber diameter from about 50 µm to about 1000 µm, from about 50 µm to about 600 µm, from about 50 µm to about 400 µm, from about 100 µm to about 325 µm, or from about 150 µm to about 275 µm.

Aspect 123 is directed to the system of Aspect 122, wherein the second fiber diameter is equal to or less than the first fiber diameter.

Aspect 124 is directed to the system of any one of Aspects 119-123, wherein the plurality of openings comprises an opening diameter of from about 100 µm to about 1000 µm, from about 200 µm to about 900 µm, or from about 225 µm to about 800 µm.

Aspect 125 is directed to the system of any one of Aspects 119-124, wherein a ratio of the opening diameter to the fiber diameter is from about 1.0 to about 3.5, from about 1.25 to about 3.25, from about 1.4 to about 3.0, from about 1.5 to about 2.9, from about 1.5 to about 2.4, or from about 2.4 to about 2.9.

Aspect 126 is directed to the system of any one of Aspects 119-125, wherein the plurality of openings is arrayed in a regular pattern.

Aspect 127 is directed to the system of any one of Aspects 118-126, wherein the cell culture matrix comprises a plurality of substrates that comprises woven meshes of differing geometries, wherein the differing geometries are different in at least one of fiber diameter, opening diameter, or opening geometry.

Aspect 128 is directed to the system of Aspect 127, wherein the woven meshes of differing geometries are ordered in a predetermined arrangement based on desired flow characteristics within the bioreactor vessel.

Aspect 129 is directed to the system of any one of Aspects 118-128, wherein the cell culture matrix is configured for culturing and/or harvesting at least one of cells, proteins, antibodies, viruses, viral vectors, virus-like particles (VLPs), microvesicles, exosomes, and polysaccharides.

Aspect 130 is directed to the system of any one of Aspects 118-129, wherein the substrate comprises a functionalized surface, the functionalized surface being physically or chemically modified for improved adhesion of the adherent cells to the polymer mesh material.

Aspect 131 is directed to the system of any one of Aspects 118-130, wherein the plurality of interwoven fibers are arranged in an ordered, non-random arrangement with respect to each other interwoven fiber of the plurality of interwoven fibers.

Aspect 132 is directed to the system of any one of Aspects 118-131, wherein at least a portion of the plurality of substrates are not separated by a spacer material or barrier.

Aspect 133 is directed to the system of any one of Aspects 118-132, wherein at least a portion of the plurality of substrates are in physical contact with each other.

Aspect 134 is directed to a method of culturing cells in a bioreactor system according to any one of Aspects 118-133, the method comprising: seeding cells on the cell culture matrix; culturing the cells on the cell culture matrix; and harvesting a product of the culturing of the cells, wherein the plurality of openings in the substrate is configured to allow flow of at least one of cell culture media, cells, or cell products through the thickness of the substrate.

Aspect 135 is directed to the method of Aspect 134, wherein the seeding comprises attaching the cells to the substrate.

Aspect 136 is directed to the method of Aspect 135, wherein the seeding comprises injecting a cell inoculum directly into the cell culture matrix.

Aspect 137 is directed to the method of any one of Aspects 134-136, further comprising perfusing cell media through the culture chamber after injecting the cell inoculum.

Aspect 138 is directed to the method of any one of Aspects 134-137, further comprising providing a media conditioning vessel fluidly connected to the bioreactor vessel and supplying the cell culture media from the media conditioning vessel to the bioreactor vessel.

Aspect 139 is directed to the method of Aspect 138, wherein, during or after culturing, at least a portion of the media is recovered from the bioreactor vessel and returned to the media conditioning vessel.

Aspect 140 is directed to the method of any one of Aspects 134-139, further comprising controlling the flow of cell culture media to the cell culture chamber, wherein the cell culture media comprises at least one of cells, cell culture nutrients, or oxygen.

Aspect 141 is directed to a bioreactor system comprising: a cell culture vessel comprising a first end, a second end, and at least one reservoir between the first and second ends; and a cell culture matrix disposed in the at least one reservoir, the cell culture matrix comprising a plurality of woven substrates each comprising a plurality of interwoven fibers with surfaces configured for adhering cells thereto, wherein the bioreactor system is configured to flow material through the at least one reservoir in a flow direction from the first end to the second end, wherein the substrates of the plurality of woven substrates are stacked such that each woven substrate is substantially parallel to each of the other woven substrates and is substantially parallel to the flow direction.

Aspect 142 is directed to the system of Aspect 141, wherein each of the substrates comprises a first side, a second side opposite the first side, a thickness separating the first and second sides, and a plurality of openings pass through the thickness of the substrate.

Aspect 143 is directed to the system of Aspect 141 or Aspect 119, wherein the substrate comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 144 is directed to the system of any one of Aspects 141-143, wherein the plurality of interwoven fibers comprises a first fiber with a first fiber diameter from about 50 µm to about 1000 µm, from about 50 µm to about 600 µm, from about 50 µm to about 400 µm, from about 100 µm to about 325 µm, or from about 150 µm to about 275 µm.

Aspect 145 is directed to the system of Aspect 144, wherein the plurality of interwoven fibers further comprises a second fiber with a second fiber diameter from about 50 µm to about 1000 µm, from about 50 µm to about 600 µm, from about 50 µm to about 400 µm, from about 100 µm to about 325 µm, or from about 150 µm to about 275 µm.

Aspect 146 is directed to the system of Aspect 145, wherein the second fiber diameter is equal to or less than the first fiber diameter.

Aspect 147 is directed to the system of any one of Aspects 142-146, wherein the plurality of openings comprises an opening diameter of from about 100 µm to about 1000 µm, from about 200 µm to about 900 µm, or from about 225 µm to about 800 µm.

Aspect 148 is directed to the system of any one of Aspects 142-147, wherein a ratio of the opening diameter to the fiber diameter is from about 1.0 to about 3.5, from about 1.25 to about 3.25, from about 1.4 to about 3.0, from about 1.5 to about 2.9, from about 1.5 to about 2.4, or from about 2.4 to about 2.9.

Aspect 149 is directed to the system of any one of Aspects 142-148, wherein the plurality of openings is arrayed in a regular pattern.

Aspect 150 is directed to the system of any one of Aspects 141-149, wherein the cell culture matrix comprises a plurality of substrates that comprises woven meshes of differing geometries, wherein the differing geometries are different in at least one of fiber diameter, opening diameter, or opening geometry.

Aspect 151 is directed to the system of Aspect 150, wherein the woven meshes of differing geometries are ordered in a predetermined arrangement based on desired flow characteristics within the bioreactor vessel.

Aspect 152 is directed to the system of any one of Aspects 141-151, wherein the cell culture matrix is configured for culturing and/or harvesting at least one of cells, proteins, antibodies, viruses, viral vectors, virus-like particles (VLPs), microvesicles, exosomes, and polysaccharides.

Aspect 153 is directed to the system of any one of Aspects 141-152, wherein the substrate comprises a functionalized surface, the functionalized surface being physically or chemically modified for improved adhesion of the adherent cells to the polymer mesh material.

Aspect 154 is directed to the system of any one of Aspects 141-153, wherein the plurality of interwoven fibers are arranged in an ordered, non-random arrangement with respect to each other interwoven fiber of the plurality of interwoven fibers.

Aspect 155 is directed to the system of any one of Aspects 141-154, wherein at least a portion of the plurality of substrates are not separated by a spacer material or barrier.

Aspect 156 is directed to the system of any one of Aspects 141-155, wherein at least a portion of the plurality of substrates are in physical contact with each other.

Aspect 157 is directed to a method of culturing cells in a bioreactor system according to any one of Aspects 141-156, the method comprising: seeding cells on the cell culture matrix; culturing the cells on the cell culture matrix; and harvesting a product of the culturing of the cells, wherein the plurality of openings in the substrate is configured to allow flow of at least one of cell culture media, cells, or cell products through the thickness of the substrate.

Aspect 158 is directed to the method of Aspect 157, wherein the seeding comprises attaching the cells to the substrate.

Aspect 159 is directed to the method of Aspect 158, wherein the seeding comprises injecting a cell inoculum directly into the cell culture matrix.

Aspect 160 is directed to the method of any one of Aspects 157-159, further comprising perfusing cell media through the culture chamber after injecting the cell inoculum.

Aspect 161 is directed to the method of any one of Aspects 157-160, further comprising providing a media conditioning vessel fluidly connected to the bioreactor vessel and supplying the cell culture media from the media conditioning vessel to the bioreactor vessel.

Aspect 162 is directed to the method of Aspect 161, wherein, during or after culturing, at least a portion of the media is recovered from the bioreactor vessel and returned to the media conditioning vessel.

Aspect 163 is directed to the method of any one of Aspects 157-162, further comprising controlling the flow of cell culture media to the cell culture chamber, wherein the cell culture media comprises at least one of cells, cell culture nutrients, or oxygen.

Aspect 164 is directed to a bioreactor system comprising: a cell culture vessel comprising a first end, a second end, and at least one reservoir between the first and second ends; and a cell culture matrix disposed in the at least one reservoir, the cell culture matrix comprising a woven substrate comprising a plurality of interwoven fibers with surfaces configured for adhering cells thereto, and wherein the woven substrate is disposed within the at least one reservoir in a wound configuration to provide a cylindrical cell culture matrix with a surface of the woven substrate being parallel to a longitudinal axis of the cylindrical cell culture matrix.

Aspect 165 is directed to the system of Aspect 164, wherein the woven substrate is disposed within the at least one reservoir as a cylindrical substrate at least partially surrounding the central longitudinal axis of the bioreactor vessel.

Aspect 166 is directed to the system of Aspect 164 or Aspect 265, wherein the bioreactor system is configured to flow material through the at least one reservoir in a flow direction from the first end to the second end.

Aspect 167 is directed to the system of Aspect 166, wherein a central longitudinal axis of the cylindrical substrate is parallel to a flow direction of the media.

Aspect 168 is directed to the system of any one of Aspects 164-167, wherein the cylindrical substrate comprises a rolled woven substrate that is configured to expand to be in contact with a wall of the at least one reservoir via an un-rolling of the rolled woven substrate.

Aspect 169 is directed to the system of any one of Aspects 164-168, wherein the rolled woven substrate is configured to expand to a shape of the interior of the at least one reservoir in the cell culture vessel.

Aspect 170 is directed to the system of Aspect 169, wherein the rolled woven substrate is configured to be inserted into the culture space while the rolled woven substrate is in a contracted rolled state and to expand within the reservoir when disposed within the reservoir.

Aspect 171 is directed to the system of Aspect 169 or Aspect 170, wherein the rolled woven substrate and the reservoir are configured such that frictional forces between the woven substrate and the wall of the reservoir hold the woven substrate substantially in place within the reservoir.

Aspect 172 is directed to the system of any one of Aspects 169-171, wherein the rolled woven substrate is configured to be inserted into the reservoir through an opening in the cell culture vessel.

Aspect 173 is directed to the system of Aspect 172, wherein the opening is one of the inlet and the outlet of the cell culture vessel.

Aspect 174 is directed to the system of any one of Aspects 164-173, wherein the cell culture vessel comprises a substrate support within the reservoir, the substrate support being configured to guide, align, or secure the woven substrate within the culture space.

Aspect 175 is directed to the system of Aspect 174, wherein the substrate support comprises a support member extending from one of the first or second end towards the other of the first or second end, wherein the rolled woven substrate is configured to surround at least a portion of a circumference of the support member such that the support member is parallel to the central longitudinal axis of the rolled woven substrate.

Aspect 176 is directed to the system of any one of Aspects 164-175, wherein the central longitudinal axis is perpendicular to the direction of gravity during cell culture.

Aspect 177 is directed to the system of any one of Aspects 164-175, wherein at least one of the reservoir and the cell culture matrix is configured to rotate about a central longitudinal axis of the bioreactor vessel during cell culture.

Aspect 178 is directed to the system of Aspect 177, wherein the bioreactor system is configured such that the substrate is moved through the cell culture fluid during the rotation of the cell culture vessel.

Aspect 179 is directed to the system of Aspect 177 or Aspect 178, wherein the bioreactor system further comprises a rotation means operably coupled to the cell culture vessel and configured to rotate the cell culture vessel about the central longitudinal axis.

Aspect 180 is directed to the system of any one of Aspects 164-179, wherein the cylindrical cell culture matrix comprises the woven cell culture substrate without any other solid material between adjacent surfaces of the cell culture substrate.

Aspect 181 is directed to a method of culturing cells in a bioreactor, the method comprising: providing a bioreactor vessel, the bioreactor vessel comprising: a cell culture chamber within the bioreactor vessel, and a cell culture matrix disposed in the cell culture chamber and configured to culture cells thereon, the cell culture matrix comprising a substrate comprising a first side, a second side opposite the first side, a thickness separating the first side and the second side, and a plurality of openings formed in the substrate and passing through the thickness of the substrate; seeding cells on the cell culture matrix; culturing the cells on the cell culture matrix; and harvesting a product of the culturing of the cells, wherein the plurality of openings in the substrate is configured to allow flow of at least one of cell culture media, cells, or cell products through the thickness of the substrate.

Aspect 182 is directed to the method of Aspect 181, wherein the substrate comprises at least one of a molded polymer lattice sheet, a 3D-printed lattice sheet, and a woven mesh sheet.

Aspect 183 is directed to the method of Aspect 181 or Aspect 182, wherein the substrate comprises a polymer material.

Aspect 184 is directed to the method of Aspect 183, wherein the polymer material is at least one of polystyrene, polyethylene terephthalate, polycarbonate, polyvinylpyrrolidone, polybutadiene, polyvinylchloride, polyethylene oxide, polypyrroles, and polypropylene oxide.

Aspect 185 is directed to the method of any one of Aspects 181-184, wherein the seeding comprises attaching the cells to the substrate.

Aspect 186 is directed to the method of any one of Aspects 181-185, wherein the seeding comprises injecting a cell inoculum directly into the cell culture matrix.

Aspect 187 is directed to the method of Aspect 186, wherein the cell inoculum is injected through a cell inoculum injection port in the bioreactor vessel.

Aspect 188 is directed to the method of Aspect 186 or Aspect 187, wherein a volume of the cell inoculum is about equal to a void volume of the cell culture chamber.

Aspect 189 is directed to the method of any one of Aspects 186-188, further comprising perfusing cell media through the culture chamber after injecting the cell inoculum.

Aspect 190 is directed to the method of any one of Aspects 181-189, further comprising supplying at least one of cell culture media and oxygen to the cells during culturing.

Aspect 191 is directed to the method of Aspect 190, wherein the supplying of the cell culture media comprises flowing the cell culture media through the cell culture chamber and across the substrate.

Aspect 192 is directed to the method of Aspect 190 or Aspect 191, wherein the supplying the cell culture media comprises providing a media conditioning vessel fluidly connected to the bioreactor vessel and supplying the cell culture media from the media conditioning vessel to the bioreactor vessel.

Aspect 193 is directed to the method of Aspect 192, wherein, during or after culturing, at least a portion of the media is recovered from the bioreactor vessel and returned to the media conditioning vessel.

Aspect 194 is directed to the method of any one of Aspects 181-193, further comprising controlling the flow of cell culture media to the cell culture chamber, wherein the cell culture media comprises at least one of cells, cell culture nutrients, or oxygen.

Aspect 195 is directed to the method of any one of Aspects 181-194, further comprising analyzing the cell culture media, the cells, and/or the cell products within the bioreactor vessel or output from the bioreactor vessel.

Aspect 196 is directed to the method of Aspect 195, wherein the analyzing comprises measuring at least one of $pH_1$, $pO_1$, $[glucose]_1$, $pH_2$, $pO_2$, $[glucose]_2$, and flow rate, wherein $pH_1$, $pO_1$, and $[glucose]_1$ are measured within the cell culture chamber, and wherein $pH_2$, $pO_2$, and $[glucose]_2$ are measured at an outlet of the cell culture chamber or the bioreactor vessel.

Aspect 197 is directed to the method of Aspect 195 or Aspect 196, wherein the flow of cell culture media to the cell culture chamber is controlled based on at least in part the results of the analyzing the cell culture media, the cells, and/or the cell products.

Aspect 198 is directed to the method of any one of Aspects 196-197, wherein a perfusion flow rate of the cell culture media to the cell culture chamber is continued at a present rate if at least one of $pH_2 \geq pH_{2min}$, $pO_2 \geq pO_{2min}$, and $[glucose]_2 \geq [glucose]_{2min}$, wherein $pH_{2min}$, and $[glucose]_{2min}$, are predetermined based on the cell culture system design.

Aspect 199 is directed to the method of any one of Aspects 196-198, wherein if the current flow rate is less than or equal to a predetermined max flow rate of the cell culture system, the perfusion flow rate is increased.

Aspect 200 is directed to the method of any one of Aspects 196-199, wherein if the current flow rate is not less than or equal to the predetermined max flow rate of the cell culture system, a controller of the cell culture system reevaluates at least one of: $pH_{2min}$, $pO_{2min}$, and $[glucose]_{2min}$; $pH_1$, $pO_1$, and $[glucose]_1$; and a height of the bioreactor vessel.

Aspect 201 is directed to the method of any one of Aspect 181-200, wherein the cells have a viability of over about 90% or over about 95% after culturing for at least about 24 hours, at least about 48 hours, or at least about 72 hours.

Aspect 202 is directed to the method of any one of Aspects 181-201, wherein the cells comprise at least one of adherent cells, suspension cells, and loosely adherent cells that adhere to the cell culture matrix.

Aspect 203 is directed to the method of any one of Aspects 181-202, wherein the product of the culturing of the cells comprises at least one of cells, proteins, antibodies, viruses, viral vectors, virus-like particles (VLPs), microvesicles, exosomes, and polysaccharides.

Aspect 204 is directed to the method of Aspect 203, wherein the product of the culturing of the cells comprises cells that are at least 80% viable, at least 85% viable, at least 90% viable, at least 91% viable, at least 92% viable, at least 93% viable, at least 94% viable, at least 95% viable, at least 96% viable, at least 97% viable, at least 98% viable, or at least 99% viable.

Aspect 205 is directed to a cell culture matrix comprising: a woven substrate comprising a plurality of fibers that are interwoven and a plurality of openings disposed between the plurality of fibers, wherein the fibers each comprise a surface configured for adhering cells thereto.

Aspect 206 is directed to the matrix of Aspect 205, wherein the surface of the fibers is configured for releasably adhering cells thereto.

Aspect 207 is directed to the matrix of Aspect 205 or Aspect 206, wherein the plurality of fibers comprises polymer fibers.

Aspect 208 is directed to the matrix of Aspect 207, wherein the polymer fibers comprise at least one of polystyrene, polyethylene terephthalate, polycarbonate, polyvinylpyrrolidone, polybutadiene, polyvinylchloride, polyethylene oxide, polypyrroles, and polypropylene oxide.

Aspect 209 is directed to the matrix of any one of Aspects 205-208, the cell culture matrix further comprising a plurality of woven substrates.

Aspect 210 is directed to the matrix of Aspect 209, wherein each substrate of the plurality of substrates comprises a first side, a second side opposite the first side, a thickness separating the first and second sides, wherein the plurality of openings pass through the thickness of the substrate.

Aspect 211 is directed to the matrix of Aspect 209 or Aspect 210, wherein the substrates of the plurality of substrates are arranged adjacent to each other such that one of the first and second side of a substrate is adjacent to other of the first or second side of an adjacent substrate.

Aspect 212 is directed to the matrix of any one of Aspects 209-211, wherein at least a portion of the plurality of substrates are not separated by a spacer material or barrier.

Aspect 213 is directed to the matrix of any one of Aspects 205-212, wherein at least a portion of the plurality of substrates are in physical contact with each other.

Definitions

"Wholly synthetic" or "fully synthetic" refers to a cell culture article, such as a microcarrier or surface of a culture vessel, that is composed entirely of synthetic source materials and is devoid of any animal derived or animal sourced materials. The disclosed wholly synthetic cell culture article eliminates the risk of xenogeneic contamination.

"Include," "includes," or like terms means encompassing but not limited to, that is, inclusive and not exclusive.

"Users" refers to those who use the systems, methods, articles, or kits disclosed herein, and include those who are culturing cells for harvesting of cells or cell products, or those who are using cells or cell products cultured and/or harvested according to embodiments herein.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, and like aspects, and ranges thereof, are for illustration only; they do not exclude other defined values or other values within defined ranges. The systems, kits, and methods of the disclosure can include any value or any combination of the values, specific values, more specific values, and preferred values described herein, including explicit or implicit intermediate values and ranges.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred.

It will be apparent to those skilled in the art that various modifications and variations can be made without departing from the spirit or scope of the disclosed embodiments. Since modifications, combinations, sub-combinations and variations of the disclosed embodiments incorporating the spirit and substance of the embodiments may occur to persons skilled in the art, the disclosed embodiments should be construed to include everything within the scope of the appended claims and their equivalents.

What is claimed:

1. A packed-bed bioreactor system comprising:
   a cell culture vessel comprising a first end, a second end, and at least one reservoir between the first and second ends; and
   a cell culture matrix disposed in the at least one reservoir, the cell culture matrix comprising a structurally defined substrate comprising a plurality of interwoven fibers with surfaces configured for adhering cells thereto, the plurality of interwoven fibers defining a plurality of pores,
   wherein the substrate is disposed within the at least one reservoir in a wound configuration creating a plurality of layers of substrate in the wound configuration, and
   wherein none of the plurality of layers of substrate are separated by a spacer material from a subsequent layer of the plurality of layers.

2. The packed-bed bioreactor system of claim 1, wherein the substrate is disposed within the at least one reservoir as a cylindrical substrate at least partially surrounding a central longitudinal axis of the bioreactor vessel.

3. The packed-bed bioreactor system of claim 1, the cell culture vessel further comprising an inlet at the first end and an outlet at the second end, wherein the bioreactor system is configured to flow material into the at least one reservoir via the inlet, through the at least one reservoir in a flow direction from the first end to the second end, and out of the at least one reservoir via the outlet.

4. The packed-bed bioreactor system of claim 3, wherein the at least one reservoir defines a unitary bulk flow path for material to flow in the flow direction from the first end to the second end.

5. The packed-bed bioreactor system of claim 3, wherein a central longitudinal axis of the cylindrical substrate is parallel to the flow direction.

6. The packed-bed bioreactor system of claim 1, wherein the wound substrate is configured to expand to be in contact with a wall of the at least one reservoir via a partial un-rolling of the wound substrate.

7. The packed-bed bioreactor system of claim 1, wherein the wound substrate is configured to be inserted into the culture space while the wound substrate is in a contracted rolled state and to expand within the reservoir when disposed within the reservoir.

8. The packed-bed bioreactor system of claim 1, wherein the wound substrate and the reservoir are configured such that frictional forces between the wound substrate and the wall of the reservoir hold the wound substrate substantially in place within the reservoir.

9. The packed-bed bioreactor system of claim 1, wherein the wound substrate is configured to be inserted into the reservoir through an opening in the cell culture vessel, wherein the opening is one of the inlet and the outlet of the cell culture vessel.

10. The packed-bed bioreactor system of claim 1, wherein the cell culture vessel comprises a substrate support within the reservoir, the substrate support being configured to guide, align, or secure the substrate within the culture space.

11. The packed-bed bioreactor system of claim 10, wherein the substrate support comprises a support member extending from one of the first or second end towards the other of the first or second end, wherein the wound substrate is configured to surround at least a portion of a circumference of the substrate support member such that the substrate support member is parallel to the central longitudinal axis of the wound substrate.

12. The packed-bed bioreactor system of claim 1, wherein the cell culture matrix consists of a single sheet of the substrate wound around itself.

13. The packed-bed bioreactor system of claim 1, wherein the plurality of pores is in an ordered array that is substantially regular and uniform.

14. The packed-bed bioreactor system of claim 1, wherein the substrate comprises a physical structure and a porosity that are in an ordered array that is substantially regular and uniform.

15. The packed-bed bioreactor system of claim 1, wherein the substrate comprises a rigid monofilament fiber configured to maintain shape under fluid flow.

16. The packed-bed bioreactor system of claim 1, wherein the cell culture matrix is configured for uniform fluid flow therethrough.

17. The packed-bed bioreactor system of claim 1, further comprising means for harvesting the adherent cells or cell by-products from the reservoir.

18. The packed-bed bioreactor system of claim 17, wherein the cell by-products comprise at least one of proteins, antibodies, viruses, viral vectors, virus-like particles (VLPs), microvesicles, exosomes, and polysaccharides.

19. The packed-bed bioreactor system of claim 1, wherein the cell culture matrix comprises a plurality of substrates that comprises woven meshes of differing geometries, wherein the differing geometries are different in at least one of fiber diameter, opening diameter, or opening geometry.

20. The packed-bed bioreactor system of claim 1, wherein the substrate comprises a functionalized surface, the functionalized surface being physically or chemically modified for improved adhesion of the adherent cells to the polymer mesh material.

21. The cell culture system of claim 1, wherein the cell culture matrix comprises a coating on a surface of the substrate, the coating being configured to promote adherence of the adherent cells.

22. A packed-bed bioreactor system comprising:
a cell culture vessel comprising a first end, a second end, and at least one reservoir between the first and second ends; and
a cell culture matrix disposed in the at least one reservoir, the cell culture matrix comprising a structurally defined substrate comprising a plurality of interwoven fibers with surfaces configured for adhering cells thereto,
wherein the substrate is disposed within the at least one reservoir in a wound configuration creating a plurality of layers of substrate in the wound configuration, and
wherein the cell culture matrix comprises the woven cell culture substrate without any other solid material between adjacent surfaces of the cell culture substrate.

23. The packed-bed bioreactor system of claim 22, the cell culture vessel further comprising an inlet at the first end and an outlet at the second end, wherein the bioreactor system is configured to flow material into the at least one reservoir via the inlet, through the at least one reservoir in a flow direction from the first end to the second end, and out of the at least one reservoir via the outlet.

24. The packed-bed bioreactor system of claim 23, wherein the at least one reservoir defines a single flow path for material to flow in the flow direction from the first end to the second end.

* * * * *